United States Patent
Kasdan et al.

(10) Patent No.: US 7,319,907 B2
(45) Date of Patent: Jan. 15, 2008

(54) MULTI-LEVEL CONTROLLER SYSTEM

(75) Inventors: Harvey Kasdan, Sherman Oaks, CA (US); Kenneth S. Gold, Bell Canyon, CA (US); Jon Frank Tindel, Valencia, CA (US); Ken A. Atterholt, Thousand Oaks, CA (US); David Alan Fridge, Pasadena, CA (US)

(73) Assignee: International Remote Imaging Systems, Inc., Chatsworth, CA (US)

( * ) Notice: Subject to any disclaimer, the term of this patent is extended or adjusted under 35 U.S.C. 154(b) by 527 days.

(21) Appl. No.: 10/716,842

(22) Filed: Nov. 18, 2003

(65) Prior Publication Data

US 2005/0033455 A1    Feb. 10, 2005

Related U.S. Application Data

(60) Provisional application No. 60/427,445, filed on Nov. 18, 2002, provisional application No. 60/427,527, filed on Nov. 18, 2002.

(51) Int. Cl.
*G06F 19/00* (2006.01)
*A61B 5/00* (2006.01)
*G05B 11/01* (2006.01)
*B65D 81/00* (2006.01)

(52) U.S. Cl. .................. 700/20; 702/20; 600/322; 600/573

(58) Field of Classification Search .......... 700/90, 700/20; 600/573, 322; 702/20, 187
See application file for complete search history.

(56) References Cited

U.S. PATENT DOCUMENTS

| | | | |
|---|---|---|---|
| 4,338,024 A | | 7/1982 | Bolz et al. |
| 4,393,466 A | | 7/1983 | Deindoerfer et al. |
| 5,279,294 A | * | 1/1994 | Anderson et al. ............ 600/322 |
| 5,513,122 A | * | 4/1996 | Cheng et al. .................. 716/5 |
| 5,555,213 A | | 9/1996 | Delong et al. |
| 5,593,390 A | * | 1/1997 | Castellano et al. ......... 604/187 |
| 5,812,394 A | | 9/1998 | Lewis et al. |
| 5,812,419 A | * | 9/1998 | Chupp et al. ................ 702/20 |
| 5,825,664 A | | 10/1998 | Warrior et al. |
| 5,909,369 A | | 6/1999 | Gopinath et al. |
| 5,950,006 A | | 9/1999 | Crater et al. |
| 6,093,156 A | * | 7/2000 | Cunningham et al. ...... 600/573 |
| 6,108,425 A | | 8/2000 | Smith, Sr. et al. |
| 6,217,744 B1 | * | 4/2001 | Crosby ........................ 205/775 |
| 6,316,903 B1 | | 11/2001 | Shamoto |
| 7,019,834 B2 | * | 3/2006 | Sebok et al. ................ 356/335 |

* cited by examiner

*Primary Examiner*—Anthony Knight
*Assistant Examiner*—Sunray Chang
(74) *Attorney, Agent, or Firm*—DLA Piper US LLP

(57) ABSTRACT

The invention is a state machine having a host controller that controls a level-i controller, wherein the level-1 controller controls the level-2 controller. The level-2 controller controls system component controllers, which in turn control system components to execute a process segment. For example, the machine includes a host controller that selects a set of states to be executed, a level-1 controller that activates the set of states in a predetermined order, wherein each state includes commands, and a level-2 controller that controls system components according to the commands. A method of executing a process includes identifying a set of states to be executed, issuing state commands that need to be issued to execute the current state in the set of states, and activating a next state only after all expected status reports have been received for the current state.

24 Claims, 40 Drawing Sheets

|    | 600 | 602 | 604 | 606 |
|----|----|----|----|----|
| L1 | L2 | BEGIN | END | COMMENT |
| R  | H  | 1   | 14  | RESET THIRD LEVEL CONTROLLERS |
| 1  | 6  | 15  | 99  | RESUME RUNNING RACKS |
| G  | O  | 18  | 99  | RUN RACKS UNDER HOST CONTROL |
| S  | S  | 395 | 434 | SERVICE SPECIMEN (RUN TUBES W/O HOST PC) |
| O  | E  | 100 | 103 | CLEAR RACK |
| R  | Q  | 104 | 148 | RUN QC CONTROL |
| 1  | 7  | 149 | 336 | RUN AUTOFOCUS CONTROL |
| W  | 8  | 335 | 349 | WAIT FOR COMMAND, BUTTON, RACK OR TIMEOUT |
| Z  | Z  | 393 | 394 | SLEEP |
| P  | I  | 350 | 366 | IRISOLVE CLEAN |
| W  | S  | 435 | 439 | SHORT WAKEUP |
| W  | M  | 440 | 444 | MEDIUM WAKEUP |
| W  | L  | 445 | 449 | LONG WAKEUP |
| S  | D  | 450 | 453 | SHUTDOWN |
| W  | A  | 350 | 392 | WASH WITH BLEACH |
| D  | L  | 454 | 481 | RUN DILUENT |
| K  | L  | 482 | 485 | KILL (WAIT FOR POWER OFF) |
| B  | X  | 486 | 487 | BACKGROUND EXIT ERROR |

FIG. 6

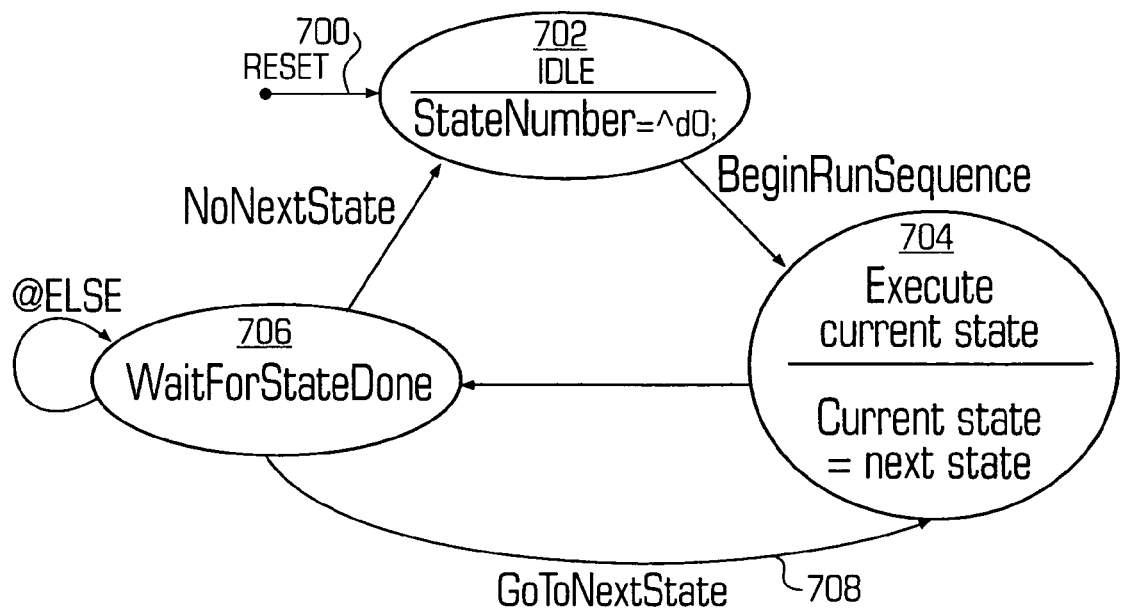

| STATE INDEX | STATE DESCRIPTION | SPACMD | FBACMD | STMCMD | OBACMD | SPASTAT | FBASTAT | STMSTAT | OBASTAT |
|---|---|---|---|---|---|---|---|---|---|
| 0 | | 0X0000 | 0X0000 | 0X0000 | 0X0000 | 0X00 | 0X00 | 0X00 | 0X00 |
| 1 | RESET HIGH | RE | RE | RE | RE | 0XFF | 0XFF | 0XFF | 0XFF |
| 2 | START SHEATH BOTTLE FILL | S1 | 0X0000 | 0X0000 | 0X0000 | 0X32 | 0X00 | 0X00 | 0X00 |
| 3 | WAIT FOR S1 IDLE AND SHEATH BOTTLE FULL, OR TIMEOUT | 0X0000 | 0X0000 | 0X0000 | 0X0000 | 0XFF | 0X00 | 0X00 | 0X00 |
| 4 | TURN OFF SHEATH PUMP | S0 | 0X0000 | 0X0000 | 0X0000 | 0X33 | 0X00 | 0X00 | 0X00 |
| 5 | WAIT FOR S0 IDLE | 0X0000 | 0X0000 | 0X0000 | 0X0000 | 0XFF | 0X00 | 0X00 | 0X00 |
| 6 | TEST SHEATH LOW SENSE CONDITION | 0X0000 | 0X0000 | 0X0000 | 0X0000 | 0X00 | 0X00 | 0X00 | 0X00 |
| 7 | SHEATH SENSE IS OK, SEND MESSAGE TOSM | 0X0000 | 0X0000 | 0X0000 | 0X0000 | 0X00 | 0X00 | 0x00 | 0x00 |
| 8 | TEST SHEATH EMPTY SENSE CONDITION | 0X0000 | 0X0000 | 0X0000 | 0X0000 | 0X00 | 0X00 | 0X00 | 0X00 |
| 9 | SHEATH SENSE IS LOW, SEND MESSAGE TOSM | 0X0000 | 0X0000 | 0X0000 | 0X0000 | 0X00 | 0X00 | 0x00 | 0x00 |
| 10 | SHEATH SENSE IS EMPTY, SEND MESSAGE TOSM, BRANCH TO "CLEAR RACK" | 0X0000 | 0X0000 | 0X0000 | 0X0000 | 0X00 | 0X00 | 0x00 | 0x00 |
| 11 | START 3 FUNCS: PH, CR,HS | PH | HS | CR | 0X0000 | 0X00 | 0X21 | 0X00 | 0x00 |
| 12 | WAIT FOR SPA | 0X0000 | 0X0000 | 0X0000 | 0X0000 | 0XFF | 0X00 | 0X00 | 0X00 |
| 13 | WAIT FOR STM | 0X0000 | 0X0000 | 0X0000 | 0X0000 | 0X00 | 0X00 | 0xFF | 0X00 |
| 14 | END RH | 0X0000 | 0X0000 | 0X0000 | 0X0000 | 0X00 | 0X00 | 0X00 | 0X00 |
| 15 | BEGINNING OF GO RESUME (16); SET FRONT PANEL LIGHTS (BUTTON GREEN, LED BLUE) | 0X0000 | 0X0000 | 0X0000 | 0X0000 | 0X00 | 0X00 | 0X00 | 0X00 |
| 16 | RE-READ THE BARCODE | 0X0000 | 0X0000 | BC | 0X0000 | 0X00 | 0X00 | 0x44 | 0X00 |
| 17 | BRANCH TO "RETRIEVE TUBE NUMBER" | 0X0000 | 0X0000 | 0X0000 | 0X0000 | 0X00 | 0X00 | 0X00 | 0X00 |
| 18 | BEGINNING OF GO COMMAND: ASK SM IF WE CAN START | 0X0000 | 0X0000 | 0X0000 | 0X0000 | 0X00 | 0X00 | 0X00 | 0X00 |
| 19 | WAIT FOR SM REPLY, WHOSE ARGUMENT INDICATES WHETHER TO PROCEED | 0X0000 | 0X0000 | 0X0000 | 0X0000 | 0X00 | 0X00 | 0X00 | 0X00 |
| 20 | IF SM REPLIES '00' BRANCH TO CANNOT_GO; ELSE FALL THROUGH | 0X0000 | 0X0000 | 0X0000 | 0X0000 | 0X00 | 0X00 | 0X00 | 0X00 |
| 21 | RESET HI,CS | RE | RE | RE | RE | 0XFF | 0XFF | 0XFF | 0XFF |
| 22 | MAKE SURE OUTPUT IS CLEAR (STM:IC RETURNS 'T' OR 'F') | 0X0000 | 0X0000 | IC | 0X0000 | 0X00 | 0X00 | 0x00 | 0X00 |
| 23 | GOT 'T'? IF SO, BRANCH TO SETFRONTPANELLIGHTS1 | 0X0000 | 0X0000 | 0X0000 | 0X0000 | 0X00 | 0X00 | 0x54 | 0X00 |
| 24 | GOT 'F'? IF SO, BRANCH TO CANNOT_GO | 0X0000 | 0X0000 | 0X0000 | 0X0000 | 0X00 | 0X00 | 0x46 | 0X00 |
| 25 | LOOP BACK TO LOOKINGFORT1 | 0X0000 | 0X0000 | 0X0000 | 0X0000 | 0X00 | 0X00 | 0X00 | 0X00 |
| 26 | SET FRONT PANEL LIGHTS (BUTTON GREEN, LED BLUE) | 0X0000 | 0X0000 | 0X0000 | 0X0000 | 0X00 | 0X00 | 0XFF | 0X00 |
| 27 | START SHEATH BOTTLE FILL | S1 | 0X0000 | 0X0000 | 0X0000 | 0X32 | 0X00 | 0X00 | 0X00 |
| 28 | WAIT FOR S1 IDLE AND SHEATH BOTTLE FULL, OR TIMEOUT | 0X0000 | 0X0000 | 0X0000 | 0X0000 | 0XFF | 0X00 | 0X00 | 0X00 |
| 29 | TURN OFF SHEATH PUMP | S0 | 0X0000 | 0X0000 | 0X0000 | 0X33 | 0X00 | 0X00 | 0X00 |
| 30 | WAIT FOR S0 IDLE | 0X0000 | 0X0000 | 0X0000 | 0X0000 | 0XFF | 0X00 | 0X00 | 0X00 |
| 31 | TEST SHEATH LOW SENSE CONDITION | 0X0000 | 0X0000 | 0X0000 | 0X0000 | 0X00 | 0X00 | 0X00 | 0X00 |
| 32 | SHEATH SENSE IS OK, SEND MESSAGE TOSM | 0X0000 | 0X0000 | 0X0000 | 0X0000 | 0X00 | 0X00 | 0x00 | 0x00 |
| 33 | TEST SHEATH EMPTY SENSE CONDITION | 0X0000 | 0X0000 | 0X0000 | 0X0000 | 0X00 | 0X00 | 0X00 | 0X00 |
| 34 | SHEATH SENSE IS LOW, SEND MESSAGE TOSM | 0X0000 | 0X0000 | 0X0000 | 0X0000 | 0X00 | 0X00 | 0x00 | 0x00 |
| 35 | SHEATH SENSE IS EMPTY, SEND MESSAGE TOSM, BRANCH TO "CLEAR RACK" | 0X0000 | 0X0000 | 0X0000 | 0X0000 | 0X00 | 0X00 | 0x00 | 0x00 |
| 36 | TELL STM TO FIND RACK, HC TO SET CP AND SP AT STARTING POSITION | PH | HC | M1 | 0X0000 | 0X00 | 0X00 | 0X00 | 0X00 |
| 37 | IF 31 FROM STM GOTO WAITUNTILSTMATIDLE1 | 0X0000 | 0X0000 | 0X0000 | 0X0000 | 0X00 | 0X00 | 0X31 | 0X00 |
| 38 | NO RACK -- ENDGOBRANCH | 0X0000 | 0X0000 | 0X0000 | 0X0000 | 0X00 | 0X00 | 0X39 | 0X00 |
| 39 | LOOP BACK | 0X0000 | 0X0000 | 0X0000 | 0X0000 | 0X00 | 0X00 | 0X00 | 0X00 |
| 40 | WAITUNTILSTMATIDLE1 (WAIT FOR SPA IDLE AS WELL) | 0X0000 | 0X0000 | 0X0000 | 0X0000 | 0XFF | 0XFF | 0XFF | 0X00 |
| 41 | MOVE TO NEXT TUBE POSITION (FIRST TUBE ASPIRATE POSITION) | 0X0000 | 0X0000 | MN | 0X0000 | 0X00 | 0X00 | 0X32 | 0X00 |
| 42 | RETRIEVE TUBE NUMBER, TELL HOST WE'RE ALIVE; BRANCH TO END RACK IF 11 (0X0B),TERM OTHERWISE | 0X0000 | 0X0000 | 0X0708 | 0X0000 | 0X00 | 0X00 | 0x0B | 0X00 |
| 43 | RETRIEVE STORED TUBE DETECT VALUE; BRANCH TO "MOVE TO NEXT TUBE..." IF 0 | 0X0000 | 0X0000 | 0X070A | 0X0000 | 0X00 | 0X00 | 0x00 | 0X00 |
| 44 | RETRIEVE RACK ID; BRANCH TO "RQ" IF 29 | 0X0000 | 0X0000 | 0X0709 | 0X0000 | 0X00 | 0X00 | 0x1D | 0X00 |
| 45 | RETRIEVE TUBE ID (BAR CODE) | 0X0000 | 0X0000 | 0X0707 | 0X0000 | 0X00 | 0X00 | 0X00 | 0X00 |
| 46 | GET SAMPLE INFO FROM HOST | 0X0000 | 0X0000 | 0X0000 | 0X0000 | 0X00 | 0X00 | 0X00 | 0X00 |
| 47 | IF SM REPLIES '00', BRANCH TO "MOVE TO NEXT TUBE..." | 0X0000 | 0X0000 | 0X0000 | 0X0000 | 0X00 | 0X00 | 0X00 | 0X00 |

| | 310 | 312 | 314 | 316 | 318 | 320 | 322 | 324 | 326 | 328 | 330 |
|---|---|---|---|---|---|---|---|---|---|---|---|
| | SMTST | TOSM | TVALUE | TFUNC | SENS | STST | SMSK | END | BRAN | DEST | TRANSLATED PARAMETERS |
| | 0X0000 | 0 | 0X0007 | 0X43 | 0X0032 | 0X01 | 0X03 | 0X0000 | 0X0101 | 0X5738 | 0X01, 0X03, 0X0000, 0X0101, 0X5738}, |
| | 0X0000 | 0 | 0X0008 | 0X44 | 0X0000 | 0X00 | 0X00 | 0XCE4E | 0X0000 | 0X0000 | 0X00, 0X00, 0XCE4E, 0X0000, 0X0000}, |
| | 0X0000 | 0 | 0x0000 | 0x00 | 0x0000 | 0x00 | 0x00 | 0x0002 | 0x0000 | 0X0000 | 0x00, 0x00, 0x0002, 0x0000, 0x0000}, |
| | 0X0000 | 0 | 0x0005 | 0x42 | 0x0033 | 0x01 | 0x01 | 0X8303 | 0X0000 | 0X0000 | 0x01, 0x01, 0X8303, 0X0000, 0X0000}, |
| | 0X0000 | 0 | 0X0000 | 0x00 | 0X0000 | 0X00 | 0X00 | 0X0002 | 0X0000 | 0X0000 | 0X00, 0X00, 0X0002, 0X0000, 0X0000}, |
| | 0X0000 | 0 | 0X0000 | 0X00 | 0X0000 | 0X00 | 0X00 | 0x0002 | 0X0000 | 0X0000 | 0X00, 0X00, 0x0002, 0X0000, 0X0000}, |
| | 0X0000 | 0 | 0X0000 | 0X00 | 0X0032 | 0x00 | 0x80 | 0X8001 | 0X0001 | 8 | 0x00, 0x80, 0X8001, 0X0001, 8}, |
| | 0X0000 | 0x1F | 0x0000 | 0x00 | 0X0000 | 0x00 | 0x00 | 0x0000 | 0x0101 | 11 | 0x00, 0x00, 0x0000, 0x0101, 11}, |
| | 0X0000 | 0 | 0X0000 | 0X00 | 0X0032 | 0x00 | 0x40 | 0X8001 | 0X0001 | 10 | 0x00, 0x40, 0X8001, 0X0001, 10}, |
| | 0X0000 | 0x20 | 0x0000 | 0x00 | 0X0000 | 0x00 | 0x00 | 0x0000 | 0x0101 | 11 | 0x00, 0x00, 0x0000, 0x0101, 11}, |
| | 0X0000 | 0x21 | 0x0000 | 0x00 | 0X0000 | 0x00 | 0x00 | 0x0000 | 0x0101 | 0x3045 | 0x00, 0x00, 0x0000, 0x0101, 0x3045}, |
| | 0X0000 | 0 | 0x0009 | 0x44 | 0X0000 | 0X00 | 0X00 | 0X005F | 0X0000 | 0X0000 | 0X00, 0X00, 0X005F, 0X0000, 0X0000}, |
| | 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| | 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| | 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| | 0X0000 | 0 | 0X0000 | 0X00 | 0X6000 | 0X09 | 0X00 | 0x0101 | 0X0000 | 0X0000 | 0X09, 0X00, 0x0101, 0X0000, 0X0000}, |
| | 0X0000 | 0 | 0x000E | 0x44 | 0X0000 | 0X00 | 0X00 | 0X001F | 0X0000 | 0X0000 | 0X00, 0X00, 0X001F, 0X0000, 0X0000}, |
| | 0X0000 | 0 | 0X0000 | 0X00 | 0X0000 | 0X00 | 0X00 | 0X0000 | 0x0101 | 42 | 0X00, 0X00, 0X0000, 0x0101, 42}, |
| | 0X0000 | 0X82 | 0X0000 | 0X00 | 0x6001 | 0x11 | 0X00 | 0X0101 | 0X0000 | 0X0000 | 0x11, 0X00, 0X0101, 0X0000, 0X0000}, |
| | 0X3044 | 0 | 0x000F | 0x44 | 0x6001 | 0x11 | 0X00 | 0X001F | 0X0000 | 0X0000 | 0x11, 0X00, 0X001F, 0X0000, 0X0000}, |
| | 0X3030 | 0 | 0X0000 | 0X00 | 0X0000 | 0X00 | 0X00 | 0X0101 | 0X0020 | 98 | 0X00, 0X00, 0X0101, 0X0020, 98}, |
| | 0X0000 | 0 | 0X0010 | 0x44 | 0x6000 | 0x11 | 0X00 | 0XCA4A | 0X0000 | 0X0000 | 0x11, 0X00, 0XCA4A, 0X0000, 0X0000}, |
| | 0X0000 | 0 | 0X0000 | 0X00 | 0X0000 | 0X00 | 0X00 | 0X0101 | 0X0000 | 0X0000 | 0X00, 0X00, 0X0101, 0X0000, 0X0000}, |
| | 0X0000 | 0 | 0X0000 | 0X00 | 0X0000 | 0X00 | 0X00 | 0X0101 | 0x0008 | 26 | 0X00, 0X00, 0X0101, 0x0008, 26}, |
| | 0X0000 | 0 | 0X0000 | 0X00 | 0X0000 | 0X00 | 0X00 | 0X0101 | 0x0008 | 98 | 0X00, 0X00, 0X0101, 0x0008, 98}, |
| | 0X0000 | 0 | 0X0000 | 0X00 | 0x0000 | 0x00 | 0X00 | 0x0000 | 0x0101 | 23 | 0x00, 0X00, 0x0000, 0x0101, 23}, |
| | 0X0000 | 0 | 0X0000 | 0X00 | 0X6000 | 0X09 | 0X00 | 0X005F | 0X0000 | 0X0000 | 0X09, 0X00, 0X005F, 0X0000, 0X0000}, |
| | 0X0000 | 0 | 0x0000 | 0x00 | 0x0000 | 0x00 | 0x00 | 0x0002 | 0X0000 | 0X0000 | 0x00, 0x00, 0x0002, 0X0000, 0X0000}, |
| | 0X0000 | 0 | 0x0005 | 0x42 | 0x0033 | 0x01 | 0x01 | 0X8303 | 0X0000 | 0X0000 | 0x01, 0x01, 0X8303, 0X0000, 0X0000}, |
| | 0X0000 | 0 | 0X0000 | 0x00 | 0X0000 | 0X00 | 0X00 | 0X0002 | 0X0000 | 0X0000 | 0X00, 0X00, 0X0002, 0X0000, 0X0000}, |
| | 0X0000 | 0 | 0X0000 | 0X00 | 0X0000 | 0X00 | 0X00 | 0x0002 | 0X0000 | 0X0000 | 0X00, 0X00, 0x0002, 0X0000, 0X0000}, |
| | 0X0000 | 0 | 0X0000 | 0X00 | 0X0032 | 0x00 | 0x80 | 0X8001 | 0X0001 | 33 | 0x00, 0x80, 0X8001, 0X0001, 33}, |
| | 0X0000 | 0x1F | 0x0000 | 0x00 | 0X0000 | 0x00 | 0x00 | 0x0000 | 0x0101 | 36 | 0x00, 0x00, 0x0000, 0x0101, 36}, |
| | 0X0000 | 0 | 0X0000 | 0X00 | 0X0032 | 0x00 | 0x40 | 0X8001 | 0X0001 | 35 | 0x00, 0x40, 0X8001, 0X0001, 35}, |
| | 0X0000 | 0x20 | 0x0000 | 0x00 | 0X0000 | 0x00 | 0x00 | 0x0000 | 0x0101 | 36 | 0x00, 0x00, 0x0000, 0x0101, 36}, |
| | 0X0000 | 0x21 | 0x0000 | 0x00 | 0X0000 | 0x00 | 0x00 | 0x0000 | 0x0101 | 0x3045 | 0x00, 0x00, 0x0000, 0x0101, 0x3045}, |
| | 0X0000 | 0 | 0X0000 | 0X00 | 0X0000 | 0X00 | 0X00 | 0X0101 | 0X0000 | 0X0000 | 0X00, 0X00, 0X0101, 0X0000, 0X0000}, |
| | 0X0000 | 0 | 0X0000 | 0X00 | 0X0000 | 0X00 | 0X00 | 0X0101 | 0X0008 | 40 | 0X00, 0X00, 0X0101, 0X0008, 40}, |
| | 0X0000 | 0 | 0X0000 | 0X00 | 0X0000 | 0X00 | 0X00 | 0X0101 | 0X0008 | 94 | 0X00, 0X00, 0X0101, 0X0008, 94}, |
| | 0X0000 | 0 | 0X0000 | 0X00 | 0X0000 | 0X00 | 0X00 | 0X001F | 0X0101 | 37 | 0X00, 0X00, 0X001F, 0X0101, 37}, |
| | 0X0000 | 0 | 0x0011 | 0x44 | 0X0000 | 0X00 | 0X00 | 0x8F0E | 0X0000 | 0X0000 | 0X00, 0X00, 0x8F0E, 0X0000, 0X0000}, |
| | 0X0000 | 0x36 | 0x0012 | 0x44 | 0X0000 | 0X00 | 0X00 | 0X001F | 0X0000 | 0X0000 | 0X00, 0X00, 0X001F, 0X0000, 0X0000}, |
| | 0X0000 | 0x32 | 0x0013 | 0x44 | 0X0000 | 0X00 | 0X00 | 0X0101 | 0X0008 | 81 | 0X00, 0X00, 0X0101, 0X0008, 81}, |
| | 0X0000 | 0 | 0x0014 | 0x44 | 0X0000 | 0X00 | 0X00 | 0X0101 | 0X0008 | 41 | 0X00, 0X00, 0X0101, 0X0008, 41}, |
| | 0X0000 | 0 | 0x0015 | 0x44 | 0X0000 | 0X00 | 0X00 | 0X0101 | 0x0008 | 0x5251 | 0X00, 0X00, 0X0101, 0x0008, 0x5251}, |
| | 0X0000 | 0 | 0x0016 | 0x44 | 0X0000 | 0X00 | 0X00 | 0X0101 | 0X0000 | 0X0000 | 0X00, 0X00, 0X0101, 0X0000, 0X0000}, |
| | 0X3032 | 0X81 | 0x0017 | 0x44 | 0X0000 | 0X00 | 0X00 | 0X001F | 0X0000 | 0x0000 | 0X00, 0X00, 0X001F, 0X0000, 0X0000}, |
| | 0X3030 | 0 | 0X0000 | 0X00 | 0X0000 | 0X00 | 0X00 | 0X0101 | 0X0020 | 41 | 0X00, 0X00, 0X0101, 0X0020, 41}, |

FIG. 8B1

| STATE INDEX | STATE DESCRIPTION | SPACMD | FBACMD | STMCMD | OBACMD | SPASTAT | FBASTAT | STMSTAT | OBASTAT |
|---|---|---|---|---|---|---|---|---|---|
| 48 | IF SM REPLIES '-2', BRANCH TO "OE" (CLEAR RACK) | 0X0000 | 0X0000 | 0X0000 | 0X0000 | 0x00 | 0x00 | 0x00 | 0x00 |
| 49 | TO TEST TUBE (INITIALIZE EP PUMP) | TT | 0X0000 | 0X0000 | 0X0000 | 0x11 | 0x00 | 0x00 | 0x00 |
| 50 | WAIT FOR TT COMPLETE | 0X0000 | 0X0000 | 0X0000 | 0X0000 | 0xFF | 0x00 | 0x00 | 0x00 |
| 51 | WAIT FOR "IMAGE PROCESSING IDLE" | 0X0000 | 0X0000 | 0X0000 | 0X0000 | 0x00 | 0x00 | 0x00 | 0x00 |
| 52 | START SHEATH FOR BACKGROUND CAPTURE | SB | 0X0000 | 0X0000 | 0X0000 | 0x31 | 0x00 | 0x00 | 0x00 |
| 53 | WAIT FOR SB COMPLETE | 0X0000 | 0X0000 | 0X0000 | 0X0000 | 0xFF | 0x00 | 0x00 | 0x00 |
| 54 | TIMER DELAY BEFORE CAPTURE | 0X0000 | 0X0000 | 0X0000 | 0X0000 | 0x00 | 0x00 | 0x00 | 0x00 |
| 55 | CAPTURE BACKGROUND AND WAIT FOR FRAME PROCESSING COMPLETE (FUTURE WAIT FOR FRAME CAPTURE COMPLETE) OR SHORT SAMPLE DETECTOR. | 0X0000 | 0X0000 | 0X0000 | 0X0000 | 0x00 | 0x00 | 0x00 | 0x00 |
| 56 | SEND "SHORT SAMPLE" SIGNAL AND WAIT FOR FRAME PROCESSING COMPLETE (FUTURE WAIT FOR FRAME CAPTURE COMPLETE). IF EXCEEDS 10 SECS - GOTO BX. | 0X0000 | 0X0000 | 0X0000 | 0X0000 | 0x00 | 0x00 | 0x00 | 0x00 |
| 57 | TURN OFF EP PUMP ON SPA | EB | 0X0000 | 0X0000 | 0X0000 | 0x34 | 0x00 | 0x00 | 0x00 |
| 58 | WAIT FOR EB COMPLETE | 0X0000 | 0X0000 | 0X0000 | 0X0000 | 0xFF | 0x00 | 0x00 | 0x00 |
| 59 | MOVE PIPETTE DOWN TO ASPIRATE POSITION IN TEST TUBE | TD | 0X0000 | 0X0000 | 0X0000 | 0x13 | 0x00 | 0x00 | 0x00 |
| 60 | WAIT FOR TD COMPLETE AND "IMAGE PROCESSING IDLE" | 0X0000 | 0X0000 | 0X0000 | 0X0000 | 0xFF | 0x00 | 0x00 | 0x00 |
| 61 | START ASPIRATION FOR SAMPLE TRANSFER | AS | RC | 0X0000 | 0X0000 | 0x17 | 0x00 | 0x00 | 0x00 |
| 62 | WAIT FOR AS AND RC COMPLETE | 0X0000 | 0X0000 | 0X0000 | 0X0000 | 0xFF | 0xFF | 0x00 | 0x00 |
| 63 | TIMER DELAY BEFORE CAPTURE | 0X0000 | 0X0000 | 0X0000 | 0X0000 | 0x00 | 0x00 | 0x00 | 0x00 |
| 64 | CAPTURE SAMPLE FRAMES AND WAIT FOR SAMPLE FRAME CAPTURE COMPLETE OR SHORT SAMPLE DETECTOR. | 0X0000 | 0X0000 | 0X0000 | 0X0000 | 0x00 | 0x00 | 0x00 | 0x00 |
| 65 | SEND "SHORT SAMPLE" SIGNAL AND WAIT FOR SAMPLE FRAME CAPTURE COMPLETE | 0X0000 | 0X0000 | 0X0000 | 0X0000 | 0x00 | 0x00 | 0x00 | 0x00 |
| 66 | TURN OFF EP PUMP ON SPA, SP PUMP ON FBA | EB | EB | 0X0000 | 0X0000 | 0x34 | 0x00 | 0x00 | 0x00 |
| 67 | WAIT FOR EB'S COMPLETE (SPA AND FBA) | 0X0000 | 0X0000 | 0X0000 | 0X0000 | 0xFF | 0xFF | 0x00 | 0x00 |
| 68 | TO WASTE WELL | TW | DB | 0X0000 | 0X0000 | 0x15 | 0x00 | 0x00 | 0x00 |
| 69 | | 0X0000 | 0X0000 | 0X0000 | 0X0000 | 0xFF | 0x00 | 0x00 | 0x00 |
| 70 | | 0X0000 | 0X0000 | 0X0000 | 0X0000 | 0x00 | 0xFF | 0x00 | 0x00 |
| 71 | TEST SHEATH FULL SENSOR | 0X0000 | 0X0000 | 0X0000 | 0X0000 | 0x00 | 0x00 | 0x00 | 0x00 |
| 72 | TURN ON RINSE PUMP AND RINSE PIPETTER | TR | RP | 0X0000 | 0X0000 | 0x00 | 0x25 | 0x00 | 0x00 |
| 73 | TURN ON RINSE PUMP AND RINSE PIPETTER | TQ | RP | 0X0000 | 0X0000 | 0x00 | 0x25 | 0x00 | 0x00 |
| 74 | | 0X0000 | 0X0000 | 0X0000 | 0X0000 | 0xFF | 0x00 | 0x00 | 0x00 |
| 75 | | 0X0000 | 0X0000 | 0X0000 | 0X0000 | 0x00 | 0xFF | 0x00 | 0x00 |
| 76 | CLEAR PIPETTER/HOME CP AND SP/MOVE TO NEXT TUBE | CP | HC | MN | 0X0000 | 0x16 | 0x00 | 0x00 | 0x00 |
| 77 | | 0X0000 | 0X0000 | 0X0000 | 0X0000 | 0xFF | 0x00 | 0x00 | 0x00 |
| 78 | | 0X0000 | 0X0000 | 0X0000 | 0X0000 | 0x00 | 0xFF | 0x00 | 0x00 |
| 79 | | 0X0000 | 0X0000 | 0X0000 | 0X0000 | 0x00 | 0x00 | 0xFF | 0x00 |
| 80 | SEND COMPLETION SIGNAL TO HOST, BRANCH TO "RETRIEVE TUBE NUMBER" | 0X0000 | 0X0000 | 0X0000 | 0X0000 | 0x00 | 0x00 | 0x00 | 0x00 |
| 81 | END RACK BRANCH TARGET | 0X0000 | 0X0000 | 0X0000 | 0X0000 | 0x00 | 0xFF | 0x00 | 0x00 |
| 82 | | 0X0000 | 0X0000 | 0X0000 | 0X0000 | 0x00 | 0x00 | 0xFF | 0x00 |
| 83 | EJECT RACK | 0X0000 | 0X0000 | ER | 0X0000 | 0x00 | 0x00 | 0x33 | 0x00 |
| 84 | LOOP TO PH1 | 0X0000 | 0X0000 | 0X0000 | 0X0000 | 0x00 | 0x00 | 0x00 | 0x00 |
| 85 | START SHEATH BOTTLE FILL | S1 | 0X0000 | 0X0000 | 0X0000 | 0x32 | 0x00 | 0x00 | 0x00 |
| 86 | WAIT FOR S1 IDLE AND SHEATH BOTTLE FULL, OR TIMEOUT | 0X0000 | 0X0000 | 0X0000 | 0X0000 | 0xFF | 0x00 | 0x00 | 0x00 |
| 87 | TURN OFF SHEATH PUMP | S0 | 0X0000 | 0X0000 | 0X0000 | 0x33 | 0x00 | 0x00 | 0x00 |
| 88 | WAIT FOR S0 IDLE | 0X0000 | 0X0000 | 0X0000 | 0X0000 | 0xFF | 0x00 | 0x00 | 0x00 |
| 89 | TEST SHEATH LOW SENSE CONDITION | 0X0000 | 0X0000 | 0X0000 | 0X0000 | 0x00 | 0x00 | 0x00 | 0x00 |
| 90 | SHEATH SENSE IS OK, SEND MESSAGE TO SM | 0X0000 | 0X0000 | 0X0000 | 0X0000 | 0x00 | 0x00 | 0x00 | 0x00 |
| 91 | TEST SHEATH EMPTY SENSE CONDITION | 0X0000 | 0X0000 | 0X0000 | 0X0000 | 0x00 | 0x00 | 0x00 | 0x00 |
| 92 | SHEATH SENSE IS LOW, SEND MESSAGE TO SM | 0X0000 | 0X0000 | 0X0000 | 0X0000 | 0x00 | 0x00 | 0x00 | 0x00 |
| 93 | SHEATH SENSE IS EMPTY, SEND MESSAGE TO SM, BRANCH TO "CLEAR RACK" | 0X0000 | 0X0000 | 0X0000 | 0X0000 | 0x00 | 0x00 | 0x00 | 0x00 |
| 94 | SET SP AND CP AT PINCHED STANDBY POSITION, ENDGOBRANCHTARGET, MAKE SURE SPA AND STM IDLE | 0X0000 | HS | 0X0000 | 0X0000 | 0xFF | 0x21 | 0xFF | 0x00 |
| 95 | BRANCH TO END OF GO SEQUENCE | 0X0000 | 0X0000 | 0X0000 | 0X0000 | 0x00 | 0x00 | 0x00 | 0x00 |
| 96 | SUBR: MOVE NEXT | 0X0000 | 0X0000 | MN | 0X0000 | 0x00 | 0x00 | 0x32 | 0x00 |

FIG. 8B2

| SMTST | TOSM | TVALUE | TFUNC | SENS | STST | SMSK | END | BRAN | DEST | TRANSLATED PARAMETERS |
|---|---|---|---|---|---|---|---|---|---|---|
| 0X2D32 | 0 | 0X0000 | 0X00 | 0X0000 | 0X00 | 0X00 | 0X0101 | 0X0020 | 0x3045 | 0X00, 0X00, 0X0101, 0X0020, 0x3045}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0x3338 | 0x37 | 0X0000 | 0x00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0x001F | 0X0000 | 0X0000 | 0X00, 0X00, 0x001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0018 | 0x42 | 0X0000 | 0x00 | 0x00 | 0X0000 | 0x0000 | 0X0000 | 0x00, 0x00, 0X0000, 0x0000, 0X0000}, |
| 0X3034 | 0X83 | 0x0000 | 0x00 | 0x0032 | 0x00 | 0x02 | 0x0001 | 0x0010 | 57 | 0x00, 0x02, 0x0001, 0x0010, 57}, |
| 0X3034 | 0x31 | 0X0019 | 0x43 | 0X0000 | 0x00 | 0x00 | 0X0010 | 0x0000 | 0x4258 | 0x00, 0x00, 0X0010, 0x0000, 0x4258}, |
| 0X0000 | 0 | 0X0000 | 0X00 | 0X0000 | 0X00 | 0X00 | 0x001F | 0X0000 | 0X0000 | 0X00, 0X00, 0x001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0x3338 | 0x37 | 0X0000 | 0X00 | 0X0000 | 0X00 | 0X00 | 0x9212 | 0X0000 | 0X0000 | 0X00, 0X00, 0x9212, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0x8606 | 0X0000 | 0X0000 | 0X00, 0X00, 0x8606, 0X0000, 0X0000}, |
| 0X0000 | 0 | 0X0062 | 0x42 | 0X0000 | 0x00 | 0x00 | 0X0000 | 0x0000 | 0X0000 | 0x00, 0x00, 0X0000, 0x0000, 0X0000}, |
| 0X3036 | 0X85 | 0x0000 | 0x00 | 0x0032 | 0X00 | 0x02 | 0x0001 | 0x0010 | 66 | 0X00, 0x02, 0x0001, 0x0010, 66}, |
| 0X3036 | 0x31 | 0X0063 | 0x43 | 0X0000 | 0X00 | 0X00 | 0X0010 | 0X0000 | 0X4258 | 0X00, 0X00, 0X0010, 0X0000, 0X4258}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X8606 | 0X0000 | 0X0000 | 0X00, 0X00, 0X8606, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0x0033 | 0x01 | 0x01 | 0x0101 | 0x0001 | 73 | 0x01, 0x01, 0x0101, 0x0001, 73}, |
| 0X0000 | 0 | 0X0000 | 0X00 | 0X0000 | 0X00 | 0X00 | 0x0000 | 0x001F | 74 | 0X00, 0X00, 0x0000, 0x001F, 74}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x36 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0x0000 | 0X87 | 0X0000 | 0X00 | 0X0000 | 0X00 | 0X00 | 0X001F | 0X0101 | 42 | 0X00, 0X00, 0X001F, 0X0101, 42}, |
| 0X0000 | 0X2F | 0X001B | 0x44 | 0X0000 | 0X00 | 0X00 | 0X0004 | 0X0000 | 0X0000 | 0X00, 0X00, 0X0004, 0X0000, 0X0000}, |
| 0X0000 | 0 | 0X001C | 0x44 | 0X0000 | 0X00 | 0X00 | 0X001F | 0X0000 | 0X0000 | 0X00, 0X00, 0X001F, 0X0000, 0X0000}, |
| 0X0000 | 0 | 0X001D | 0x44 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X0000 | 0X0101 | 27 | 0X00, 0X00, 0X0000, 0X0101, 27}, |
| 0X0000 | 0 | 0x0000 | 0x00 | 0x0000 | 0x00 | 0x00 | 0x0002 | 0x0000 | 0x0000 | 0x00, 0x00, 0x0002, 0x0000, 0x0000}, |
| 0X0000 | 0 | 0x0005 | 0x42 | 0x0033 | 0x01 | 0x01 | 0X8303 | 0X0000 | 0X0000 | 0x01, 0x01, 0X8303, 0X0000, 0X0000}, |
| 0X0000 | 0 | 0X0000 | 0X00 | 0X0000 | 0X00 | 0X00 | 0x0002 | 0X0000 | 0X0000 | 0X00, 0X00, 0x0002, 0X0000, 0X0000}, |
| 0X0000 | 0 | 0X0000 | 0X00 | 0X0000 | 0X00 | 0X00 | 0x0002 | 0X0000 | 0X0000 | 0X00, 0X00, 0x0002, 0X0000, 0X0000}, |
| 0X0000 | 0 | 0X0000 | 0X00 | 0x0032 | 0x00 | 0x80 | 0X8001 | 0X0001 | 91 | 0x00, 0x80, 0X8001, 0X0001, 91}, |
| 0X0000 | 0x1F | 0X0000 | 0X00 | 0X0000 | 0X00 | 0X00 | 0x0000 | 0x0101 | 94 | 0x00, 0x00, 0x0000, 0x0101, 94}, |
| 0X0000 | 0 | 0X0000 | 0X00 | 0x0032 | 0x00 | 0x40 | 0X8001 | 0X0001 | 93 | 0x00, 0x40, 0X8001, 0X0001, 93}, |
| 0X0000 | 0x20 | 0X0000 | 0X00 | 0X0000 | 0x00 | 0x00 | 0x0000 | 0x0101 | 94 | 0x00, 0x00, 0x0000, 0x0101, 94}, |
| 0X0000 | 0x21 | 0x0000 | 0x00 | 0X0000 | 0x00 | 0x00 | 0x0000 | 0x0101 | 0x3045 | 0x00, 0x00, 0x0000, 0x0101, 0x3045}, |
| 0X0000 | 0 | 0X001E | 0x44 | 0X0000 | 0X00 | 0X00 | 0X8E0E | 0X0000 | 0X0000 | 0X00, 0X00, 0x8E0E, 0X0000, 0X0000}, |
| 0X0000 | 0 | 0X0000 | 0X00 | 0X0000 | 0X00 | 0X00 | 0x0000 | 0X0101 | 99 | 0X00, 0X00, 0x0000, 0X0101, 99}, |
| 0X0000 | 0x36 | 0X001F | 0x44 | 0X0000 | 0X00 | 0X00 | 0X001F | 0X0000 | 0X0000 | 0X00, 0X00, 0X001F, 0X0000, 0X0000}, |

FIG. 8C1

| STATE INDEX | STATE DESCRIPTION | SPACMD | FBACMD | STMCMD | OBACMD | SPASTAT | FBASTAT | STMSTAT | OBASTAT |
|---|---|---|---|---|---|---|---|---|---|
| 97 | END SUBR: BRANCH TO WAITUNTILSTMATIDLE1 | 0X0000 | 0X0000 | 0X0000 | 0X0000 | 0X00 | 0X00 | 0X00 | 0X00 |
| 98 | COULDN'T GO; FLASH RED BUTTON FOR 5 SECONDS | 0X0000 | 0X0000 | 0X0000 | 0X0000 | 0x00 | 0x00 | 0x00 | 0x00 |
| 99 | END OF GO SEQUENCE | 0X0000 | 0X0000 | 0X0000 | 0X0000 | 0X00 | 0X00 | 0X00 | 0X00 |
| 100 | BEGIN OF "OE" (CLEAR RACKS): FULL STOP | RE | RE | RE | 0X0000 | 0XFF | 0XFF | 0XFF | 0X00 |
| 101 | SEND CR TO STM; HOME PIPETTER | PH | 0X0000 | CR | 0X0000 | 0X00 | 0X00 | 0X33 | 0X00 |
| 102 | HOME STM CARRIERS | 0X0000 | 0X0000 | 0x0000 | 0X0000 | 0XFF | 0X00 | 0XFF | 0X00 |
| 103 | END OF "OE" (CLEAR RACKS) | 0X0000 | 0X0000 | 0X0000 | 0X0000 | 0X00 | 0X00 | 0X00 | 0X00 |
| 104 | BEGIN OF "RQ" (RUN QC CONTROL) | RE | RE | RE | 0X0000 | 0XFF | 0XFF | 0XFF | 0X00 |
| 105 | RETRIEVE TUBE NUMBER; BRANCH TO WASH ("WA") IF 1 (0X01), TERM OTHERWISE | 0X0000 | 0X0000 | 0X0708 | 0X0000 | 0X00 | 0X00 | 0x01 | 0X00 |
| 106 | RETRIEVE TUBE NUMBER; BRANCH TO DILUENT ("DL") IF 2 (0X02), TERM OTHERWISE | 0X0000 | 0X0000 | 0X0708 | 0X0000 | 0X00 | 0X00 | 0x02 | 0X00 |
| 107 | RETRIEVE TUBE NUMBER; BRANCH TO DILUENT ("DL") IF 3 (0X03), TERM OTHERWISE | 0X0000 | 0X0000 | 0X0708 | 0X0000 | 0X00 | 0X00 | 0x03 | 0X00 |
| 108 | RETRIEVE TUBE NUMBER; BRANCH TO AUTOFOCUS ("17") IF 5 (0X05), TERM OTHERWISE | 0X0000 | 0X0000 | 0X0708 | 0X0000 | 0X00 | 0X00 | 0x05 | 0X00 |
| 109 | RETRIEVE TUBE NUMBER; BRANCH TO DILUENT ("DL") IF 10 | 0X0000 | 0X0000 | 0X0708 | 0X0000 | 0X00 | 0X00 | 0x0A | 0X00 |
| 110 | RETRIEVE TUBE ID (BAR CODE) | 0X0000 | 0X0000 | 0X0707 | 0X0000 | 0X00 | 0X00 | 0X00 | 0X00 |
| 111 | GET SAMPLE INFO FROM HOST | 0X0000 | 0X0000 | 0X0000 | 0X0000 | 0X00 | 0X00 | 0X00 | 0X00 |
| 112 | IF SM REPLIES '00', BRANCH TO "MOVE TO NEXT CONTROL TUBE POSITION" | 0X0000 | 0X0000 | 0X0000 | 0X0000 | 0X00 | 0X00 | 0X00 | 0X00 |
| 113 | IF SM REPLIES '-2', BRANCH TO "OE" (CLEAR RACK) | 0X0000 | 0X0000 | 0X0000 | 0X0000 | 0X00 | 0X00 | 0X00 | 0X00 |
| 114 | TO TEST TUBE | TT | 0X0000 | 0X0000 | 0X0000 | 0x11 | 0x00 | 0X00 | 0X00 |
| 115 | | 0X0000 | 0X0000 | 0X0000 | 0X0000 | 0XFF | 0x00 | 0X00 | 0X00 |
| 116 | WAIT FOR "IMAGE PROCESSING IDLE" | 0X0000 | 0X0000 | 0X0000 | 0X0000 | 0x00 | 0x00 | 0X00 | 0X00 |
| 117 | START SHEATH FOR BACKGROUND CAPTURE | SB | 0X0000 | 0X0000 | 0X0000 | 0x31 | 0X00 | 0X00 | 0X00 |
| 118 | WAIT FOR SB COMPLETE | 0X0000 | 0X0000 | 0X0000 | 0X0000 | 0xFF | 0x00 | 0X00 | 0X00 |
| 119 | TIMER DELAY BEFORE CAPTURE | 0X0000 | 0X0000 | 0X0000 | 0X0000 | 0x00 | 0x00 | 0x00 | 0x00 |
| 120 | CAPTURE BACKGROUND AND WAIT FOR FRAME PROCESSING COMPLETE (FUTURE WAIT FOR FRAME CAPTURE COMPLETE) OR SHORT SAMPLE DETECTOR. | 0X0000 | 0X0000 | 0X0000 | 0X0000 | 0x00 | 0x00 | 0x00 | 0x00 |
| 121 | SEND "SHORT SAMPLE" SIGNAL AND WAIT FOR FRAME PROCESSING COMPLETE (FUTURE WAIT FOR FRAME CAPTURE COMPLETE). IF EXCEEDS 10 SECS - GOTO BX. | 0X0000 | 0X0000 | 0X0000 | 0X0000 | 0x00 | 0x00 | 0x00 | 0x00 |
| 122 | TURN OFF EP PUMP ON SPA | EB | 0X0000 | 0X0000 | 0X0000 | 0x34 | 0x00 | 0X00 | 0X00 |
| 123 | WAIT FOR EB COMPLETE | 0X0000 | 0X0000 | 0X0000 | 0X0000 | 0xFF | 0x00 | 0X00 | 0X00 |
| 124 | MOVE PIPETTE DOWN TO ASPIRATE POSITION IN TEST TUBE | TD | 0X0000 | 0X0000 | 0X0000 | 0X13 | 0x00 | 0X00 | 0X00 |
| 125 | WAIT FOR TD COMPLETE AND "IMAGE PROCESSING IDLE" | 0X0000 | 0X0000 | 0X0000 | 0X0000 | 0xFF | 0x00 | 0X00 | 0X00 |
| 126 | START ASPIRATION FOR SAMPLE TRANSFER | AS | RC | 0X0000 | 0X0000 | 0x17 | 0x00 | 0X00 | 0X00 |
| 127 | WAIT FOR AS AND RC COMPLETE | 0X0000 | 0X0000 | 0X0000 | 0X0000 | 0xFF | 0xFF | 0X00 | 0X00 |
| 128 | TIMER DELAY BEFORE CAPTURE | 0X0000 | 0X0000 | 0X0000 | 0X0000 | 0x00 | 0x00 | 0x00 | 0x00 |
| 129 | CAPTURE SAMPLE FRAMES AND WAIT FOR SAMPLE FRAME CAPTURE COMPLETE OR SHORT SAMPLE DETECTOR. | 0X0000 | 0X0000 | 0X0000 | 0X0000 | 0x00 | 0X00 | 0X00 | 0X00 |
| 130 | SEND "SHORT SAMPLE" SIGNAL AND WAIT FOR SAMPLE FRAME CAPTURE COMPLETE | 0X0000 | 0X0000 | 0X0000 | 0X0000 | 0x00 | 0X00 | 0X00 | 0X00 |
| 131 | TURN OFF EP PUMP ON SPA, SP PUMP ON FBA | EB | EB | 0X0000 | 0X0000 | 0x34 | 0x00 | 0X00 | 0X00 |
| 132 | WAIT FOR EB'S COMPLETE (SPA AND FBA) | 0X0000 | 0X0000 | 0X0000 | 0X0000 | 0xFF | 0xFF | 0X00 | 0X00 |
| 133 | TO WASTE WELL | TW | DB | 0X0000 | 0X0000 | 0x15 | 0x00 | 0X00 | 0X00 |
| 134 | | 0X0000 | 0X0000 | 0X0000 | 0X0000 | 0xFF | 0x00 | 0X00 | 0X00 |
| 135 | | 0X0000 | 0X0000 | 0X0000 | 0X0000 | 0x00 | 0xFF | 0X00 | 0X00 |
| 136 | TURN ON RINSE PUMP AND RINSE PIPETTER | TR | RP | 0X0000 | 0X0000 | 0X00 | 0x25 | 0X00 | 0X00 |
| 137 | | 0X0000 | 0X0000 | 0X0000 | 0X0000 | 0xFF | 0x00 | 0X00 | 0X00 |
| 138 | | 0X0000 | 0X0000 | 0X0000 | 0X0000 | 0x00 | 0xFF | 0X00 | 0X00 |
| 139 | CLEAR PIPETTER/HOME CP AND SP | CP | HC | 0x0000 | 0X0000 | 0X16 | 0X00 | 0X00 | 0X00 |
| 140 | | 0X0000 | 0X0000 | 0X0000 | 0X0000 | 0XFF | 0x00 | 0X00 | 0X00 |
| 141 | | 0X0000 | 0X0000 | 0X0000 | 0X0000 | 0x00 | 0xFF | 0X00 | 0X00 |
| 142 | | 0X0000 | 0X0000 | 0X0000 | 0X0000 | 0x00 | 0x00 | 0XFF | 0X00 |
| 143 | SEND COMPLETION SIGNAL TO HOST | 0X0000 | 0X0000 | 0X0000 | 0X0000 | 0X00 | 0X00 | 0X00 | 0X00 |
| 144 | WAIT FOR CONTROL RESULT FROM HOST; BRANCH TO "OE" (CLEAR RACK IF FAILED (0) | 0X0000 | 0X0000 | 0X0000 | 0X0000 | 0X00 | 0X00 | 0X00 | 0X00 |

FIG. 8C2

| SMTST | TOSM | TVALUE | TFUNC | SENS | STST | SMSK | END | BRAN | DEST | TRANSLATED PARAMETERS |
|---|---|---|---|---|---|---|---|---|---|---|
| 0X0000 | 0 | 0X0000 | 0X00 | 0X0000 | 0X00 | 0X00 | 0X0000 | 0X0101 | 40 | 0X00, 0X00, 0X0000, 0X0101, 40}, |
| 0X0000 | 0 | 0x0181 | 0x02 | 0x6001 | 0x12 | 0x00 | 0X0000 | 0x0000 | 0X0000 | 0x12, 0x00, 0X0000, 0x0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x2F | 0X0020 | 0x44 | 0X0000 | 0X00 | 0X00 | 0X8E0E | 0X0000 | 0X0000 | 0X00, 0X00, 0X8E0E, 0X0000, 0X0000}, |
| 0X0000 | 0 | 0X0021 | 0x44 | 0X0000 | 0X00 | 0X00 | 0X001F | 0X0000 | 0X0000 | 0X00, 0X00, 0X001F, 0X0000, 0X0000}, |
| 0X0000 | 0 | 0X0022 | 0x44 | 0X0000 | 0X00 | 0X00 | 0X8A0A | 0X0000 | 0X0000 | 0X00, 0X00, 0X8A0A, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0023 | 0x44 | 0X0000 | 0X00 | 0X00 | 0X8E0E | 0X0000 | 0X0000 | 0X00, 0X00, 0X8E0E, 0X0000, 0X0000}, |
| 0X0000 | 0 | 0X0024 | 0x44 | 0X0000 | 0X00 | 0X00 | 0X0101 | 0X0008 | 0x5741 | 0X00, 0X00, 0X0101, 0X0008, 0x5741}, |
| 0X0000 | 0 | 0X0025 | 0x44 | 0X0000 | 0X00 | 0X00 | 0X0101 | 0X0008 | 0x444C | 0X00, 0X00, 0X0101, 0X0008, 0x444C}, |
| 0X0000 | 0 | 0X0026 | 0x44 | 0X0000 | 0X00 | 0X00 | 0X0101 | 0X0008 | 0x444C | 0X00, 0X00, 0X0101, 0X0008, 0x444C}, |
| 0X0000 | 0 | 0X0027 | 0x44 | 0X0000 | 0X00 | 0X00 | 0X0101 | 0X0008 | 0x3137 | 0X00, 0X00, 0X0101, 0X0008, 0x3137}, |
| 0X0000 | 0 | 0X0028 | 0x44 | 0X0000 | 0X00 | 0X00 | 0X0101 | 0X0008 | 0x444C | 0X00, 0X00, 0X0101, 0X0008, 0x444C}, |
| 0X0000 | 0 | 0X0029 | 0x44 | 0X0000 | 0X00 | 0X00 | 0X0101 | 0X0000 | 0X0000 | 0X00, 0X00, 0X0101, 0X0000, 0X0000}, |
| 0X3032 | 0X81 | 0X002A | 0x44 | 0X0000 | 0X00 | 0X00 | 0X001F | 0X0000 | 0X0000 | 0X00, 0X00, 0X001F, 0X0000, 0X0000}, |
| 0X3030 | 0 | 0X0000 | 0X00 | 0X0000 | 0X00 | 0X00 | 0X0101 | 0X0020 | 146 | 0X00, 0X00, 0X0101, 0X0020, 146}, |
| 0X2D32 | 0 | 0X0000 | 0X00 | 0X0000 | 0X00 | 0X00 | 0X0101 | 0X0020 | 0x3045 | 0X00, 0X00, 0X0101, 0X0020, 0x3045}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0x3338 | 0x37 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0069 | 0x42 | 0X0000 | 0x00 | 0X00 | 0X0000 | 0x0000 | 0X0000 | 0x00, 0x00, 0X0000, 0x0000, 0X0000}, |
| 0X3034 | 0X83 | 0x0000 | 0x00 | 0x0032 | 0x00 | 0x02 | 0x0001 | 0x0010 | 122 | 0x00, 0x02, 0x0001, 0x0010, 122}, |
| 0X3034 | 0x31 | 0X006A | 0x43 | 0x0000 | 0x00 | 0x00 | 0X0010 | 0x0000 | 0x4258 | 0x00, 0x00, 0X0010, 0x0000, 0x4258}, |
| 0X0000 | 0 | 0X0000 | 0X00 | 0X0000 | 0X00 | 0X00 | 0x001F | 0X0000 | 0X0000 | 0X00, 0X00, 0x001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0x3338 | 0x37 | 0X0000 | 0X00 | 0X0000 | 0X00 | 0X00 | 0x9212 | 0X0000 | 0X0000 | 0X00, 0X00, 0x9212, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0x8606 | 0X0000 | 0X0000 | 0X00, 0X00, 0x8606, 0X0000, 0X0000}, |
| 0X0000 | 0 | 0X006B | 0x42 | 0X0000 | 0x00 | 0x00 | 0X0000 | 0X0000 | 0X0000 | 0x00, 0x00, 0X0000, 0x0000, 0X0000}, |
| 0X3036 | 0X85 | 0x0000 | 0x00 | 0x0032 | 0X00 | 0x02 | 0x0001 | 0x0010 | 131 | 0X00, 0x02, 0x0001, 0x0010, 131}, |
| 0X3036 | 0x31 | 0X006C | 0x43 | 0X0000 | 0X00 | 0X00 | 0X0010 | 0X0000 | 0X4258 | 0X00, 0X00, 0X0010, 0X0000, 0X4258}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X8606 | 0X0000 | 0X0000 | 0X00, 0X00, 0X8606, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0x0000 | 0X87 | 0X0000 | 0X00 | 0X0000 | 0X00 | 0X00 | 0x0101 | 0x0000 | 0x0000 | 0X00, 0X00, 0x0101, 0x0000, 0x0000}, |
| 0x3245 | 0 | 0X002C | 0x44 | 0X0000 | 0X00 | 0X00 | 0x001F | 0X0000 | 0X0000 | 0X00, 0X00, 0x001F, 0X0000, 0X0000}, |

| STATE INDEX | STATE DESCRIPTION | SPACMD | FBACMD | STMCMD | OBACMD | SPASTAT | FBASTAT | STMSTAT | OBASTAT |
|---|---|---|---|---|---|---|---|---|---|
| 145 | IF SM REPLIES '0', BRANCH TO "OE" (CLEAR RACK) | 0X0000 | 0X0000 | 0X0000 | 0X0000 | 0X00 | 0X00 | 0X00 | 0X00 |
| 146 | MOVE TO NEXT CONTROL TUBE POSITION | 0X0000 | 0X0000 | MN | 0X0000 | 0X00 | 0X00 | 0X32 | 0X00 |
| 147 | BRANCH TO "16" (GO RESUME) | 0X0000 | 0X0000 | 0X0000 | 0X0000 | 0X00 | 0X00 | 0X00 | 0X00 |
| 148 | END OF RQ SEQUENCE | 0X0000 | 0X0000 | 0X0000 | 0X0000 | 0X00 | 0X00 | 0X00 | 0X00 |
| 149 | BEGIN "17" (AUTOFOCUS CONTROL); RESET HLCS | RE | RE | RE | 0X0000 | 0XFF | 0XFF | 0XFF | 0X00 |
| 150 | RETRIEVE CONTROL ID (BAR CODE) | 0X0000 | 0X0000 | 0X0707 | 0X0000 | 0X00 | 0X00 | 0X00 | 0X00 |
| 151 | GET SAMPLE INFO FROM HOST | 0X0000 | 0X0000 | 0X0000 | 0X0000 | 0X00 | 0X00 | 0X00 | 0X00 |
| 152 | IF SM REPLIES '00', BRANCH TO "MOVE TO NEXT | 0X0000 | 0X0000 | 0X0000 | 0X0000 | 0X00 | 0X00 | 0X00 | 0X00 |
| 153 | IF SM REPLIES '-2', BRANCH TO "OE" (CLEAR RACK) | 0X0000 | 0X0000 | 0X0000 | 0X0000 | 0X00 | 0X00 | 0X00 | 0X00 |
| 154 | RECORD CURRENT AUTOFOCUS POSITION (REQUIRES | 0X0000 | 0X0000 | 0X0000 | HW | 0X00 | 0X00 | 0X00 | 0x31 |
| 155 | WAIT FOR OBA COMPLETE. | 0X0000 | 0X0000 | 0X0000 | 0x0000 | 0X00 | 0X00 | 0X00 | 0xFF |
| 156 | RETURN TO AUTOFOCUS POSITION | 0X0000 | 0X0000 | 0X0000 | MO | 0X00 | 0X00 | 0X00 | 0x32 |
| 157 | WAIT FOR OBA COMPLETE. | 0X0000 | 0X0000 | 0X0000 | 0x0000 | 0X00 | 0X00 | 0X00 | 0xFF |
| 158 | TO TEST TUBE (INITIALIZE EP PUMP) | TT | 0X0000 | 0X0000 | 0X0000 | 0x11 | 0x00 | 0X00 | 0X00 |
| 159 | WAIT FOR TT COMPLETE | 0X0000 | 0X0000 | 0X0000 | 0X0000 | 0xFF | 0x00 | 0X00 | 0X00 |
| 160 | DUMMY STATE (FUTURE WAIT FOR HOST TO VERIFY READY | 0X0000 | 0X0000 | 0X0000 | 0X0000 | 0x00 | 0x00 | 0X00 | 0X00 |
| 161 | MOVE PIPETTE DOWN TO ASPIRATE POSITION IN TEST | TD | 0X0000 | 0X0000 | 0X0000 | 0X13 | 0x00 | 0X00 | 0X00 |
| 162 | WAIT FOR TD COMPLETE | 0X0000 | 0X0000 | 0X0000 | 0X0000 | 0xFF | 0x00 | 0X00 | 0X00 |
| 163 | AUTOFOCUSREADYFORCOMMAND: TELL HOST WE'RE | 0X0000 | 0X0000 | 0X0000 | 0X0000 | 0X00 | 0X00 | 0X00 | 0X00 |
| 164 | WAIT FOR AN AUTO FOCUS COMMAND | 0X0000 | 0X0000 | 0X0000 | 0X0000 | 0X00 | 0X00 | 0X00 | 0X00 |
| 165 | SM REPLY = "00" --> AUTOFOCUSCLEANUP | 0X0000 | 0X0000 | 0X0000 | 0X0000 | 0X00 | 0X00 | 0X00 | 0X00 |
| 166 | SM REPLY = "01" --> | 0X0000 | 0X0000 | 0X0000 | 0X0000 | 0X00 | 0X00 | 0X00 | 0X00 |
| 167 | SM REPLY = "02" --> AUTOFOCUSCOARSE | 0X0000 | 0X0000 | 0X0000 | 0X0000 | 0X00 | 0X00 | 0X00 | 0X00 |
| 168 | SM REPLY = "03" --> AUTOFOCUSPEAK | 0X0000 | 0X0000 | 0X0000 | 0X0000 | 0X00 | 0X00 | 0X00 | 0X00 |
| 169 | SM REPLY = "04" --> AUTOFOCUSCLINICAL | 0X0000 | 0X0000 | 0X0000 | 0X0000 | 0X00 | 0X00 | 0X00 | 0X00 |
| 170 | SM REPLY = "05" --> AUTOFOCUSCLINICAL | 0X0000 | 0X0000 | 0X0000 | 0X0000 | 0X00 | 0X00 | 0X00 | 0X00 |
| 171 | SM REPLY = "10" --> | 0X0000 | 0X0000 | 0X0000 | 0X0000 | 0X00 | 0X00 | 0X00 | 0X00 |
| 172 | SM REPLY = "11" --> AUTOFOCUSPEAKFINALOFFSET | 0X0000 | 0X0000 | 0X0000 | 0X0000 | 0X00 | 0X00 | 0X00 | 0X00 |
| 173 | SM REPLY = "12" --> AUTOFOCUSCLINICALFINALOFFSET | 0X0000 | 0X0000 | 0X0000 | 0X0000 | 0X00 | 0X00 | 0X00 | 0X00 |
| 174 | SM REPLY = "20" --> AUTOFOCUSFORWARD1 | 0X0000 | 0X0000 | 0X0000 | 0X0000 | 0X00 | 0X00 | 0X00 | 0X00 |
| 175 | SM REPLY = "21" --> AUTOFOCUSFORWARD2 | 0X0000 | 0X0000 | 0X0000 | 0X0000 | 0X00 | 0X00 | 0X00 | 0X00 |
| 176 | SM REPLY = "22" --> AUTOFOCUSFORWARD4 | 0X0000 | 0X0000 | 0X0000 | 0X0000 | 0X00 | 0X00 | 0X00 | 0X00 |
| 177 | SM REPLY = "23" --> AUTOFOCUSFORWARD8 | 0X0000 | 0X0000 | 0X0000 | 0X0000 | 0X00 | 0X00 | 0X00 | 0X00 |
| 178 | SM REPLY = "24" --> AUTOFOCUSFORWARD16 | 0X0000 | 0X0000 | 0X0000 | 0X0000 | 0X00 | 0X00 | 0X00 | 0X00 |
| 179 | SM REPLY = "25" --> AUTOFOCUSFORWARD32 | 0X0000 | 0X0000 | 0X0000 | 0X0000 | 0X00 | 0X00 | 0X00 | 0X00 |
| 180 | SM REPLY = "26" --> AUTOFOCUSFORWARD64 | 0X0000 | 0X0000 | 0X0000 | 0X0000 | 0X00 | 0X00 | 0X00 | 0X00 |
| 181 | SM REPLY = "27" --> AUTOFOCUSFORWARD128 | 0X0000 | 0X0000 | 0X0000 | 0X0000 | 0X00 | 0X00 | 0X00 | 0X00 |
| 182 | SM REPLY = "28" --> AUTOFOCUSFORWARD256 | 0X0000 | 0X0000 | 0X0000 | 0X0000 | 0X00 | 0X00 | 0X00 | 0X00 |
| 183 | SM REPLY = "29" --> AUTOFOCUSFORWARD512 | 0X0000 | 0X0000 | 0X0000 | 0X0000 | 0X00 | 0X00 | 0X00 | 0X00 |
| 184 | SM REPLY = "2A" --> AUTOFOCUSFORWARD1024 | 0X0000 | 0X0000 | 0X0000 | 0X0000 | 0X00 | 0X00 | 0X00 | 0X00 |
| 185 | SM REPLY = "2B" --> AUTOFOCUSFORWARD2048 | 0X0000 | 0X0000 | 0X0000 | 0X0000 | 0X00 | 0X00 | 0X00 | 0X00 |
| 186 | BRANCH TO AUTOFOCUSREADYFORCOMMAND | 0X0000 | 0X0000 | 0X0000 | 0X0000 | 0X00 | 0X00 | 0X00 | 0X00 |
| 187 | AUTOFOCUSLIGHTLEVELADJUSTMENT: SEND CURRENT | 0X0000 | 0X0000 | 0X0000 | 0X0000 | 0X00 | 0X00 | 0X00 | 0X00 |
| 188 | WAIT FOR STROBE SETTING | 0X0000 | 0X0000 | 0X0000 | 0X0000 | 0X00 | 0X00 | 0X00 | 0X00 |
| 189 | PAUSE FOR IT TO TAKE EFFECT | 0X0000 | 0X0000 | 0X0000 | 0X0000 | 0X00 | 0X00 | 0X00 | 0X00 |

FIG. 8D2

| SMTST | TOSM | TVALUE | TFUNC | SENS | STST | SMSK | END | BRAN | DEST | TRANSLATED PARAMETERS |
|---|---|---|---|---|---|---|---|---|---|---|
| 0x3030 | 0 | 0X0000 | 0X00 | 0X0000 | 0X00 | 0X00 | 0X0101 | 0X0020 | 0x3045 | 0X00, 0X00, 0X0101, 0X0020, 0x3045}, |
| 0X0000 | 0x36 | 0X002D | 0x44 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X0000 | 0X0101 | 0x3136 | 0X00, 0X00, 0X0000, 0X0101, 0x3136}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X002E | 0x44 | 0X0000 | 0X00 | 0X00 | 0X001F | 0X0000 | 0X0000 | 0X00, 0X00, 0X001F, 0X0000, 0X0000}, |
| 0X0000 | 0 | 0X002F | 0x44 | 0X0000 | 0X00 | 0X00 | 0X0101 | 0X0000 | 0X0000 | 0X00, 0X00, 0X0101, 0X0000, 0X0000}, |
| 0X3032 | 0x81 | 0X0030 | 0x44 | 0X0000 | 0X00 | 0X00 | 0X001F | 0X0000 | 0X0000 | 0X00, 0X00, 0X001F, 0X0000, 0X0000}, |
| 0X3030 | 0 | 0X0000 | 0X00 | 0X0000 | 0X00 | 0X00 | 0X0101 | 0X0020 | 326 | 0X00, 0X00, 0X0101, 0X0020, 326}, |
| 0X2D32 | 0 | 0X0000 | 0X00 | 0X0000 | 0X00 | 0X00 | 0X0101 | 0X0020 | 0x3045 | 0X00, 0X00, 0X0101, 0X0020, 0x3045}, |
| 0X0000 | 0 | 0x2000 | 0x04 | 0X0000 | 0X00 | 0X00 | 0x0040 | 0X0000 | 0X0000 | 0X00, 0X00, 0x0040, 0X0000, 0X0000}, |
| 0X0000 | 0 | 0x2000 | 0x04 | 0X0000 | 0X00 | 0X00 | 0x0040 | 0X0000 | 0X0000 | 0X00, 0X00, 0x0040, 0X0000, 0X0000}, |
| 0X0000 | 0 | 0x2000 | 0x04 | 0X0000 | 0X00 | 0X00 | 0x0040 | 0X0000 | 0X0000 | 0X00, 0X00, 0x0040, 0X0000, 0X0000}, |
| 0X0000 | 0 | 0x2000 | 0x04 | 0X0000 | 0X00 | 0X00 | 0x0040 | 0X0000 | 0X0000 | 0X00, 0X00, 0x0040, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0061 | 0x42 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x14 | 0X0000 | 0X00 | 0X0000 | 0X00 | 0X00 | 0x0101 | 0X0000 | 0X0000 | 0X00, 0X00, 0x0101, 0X0000, 0X0000}, |
| 0x3133 | 0 | 0x2000 | 0x04 | 0X0000 | 0X00 | 0X00 | 0X001F | 0x0000 | 0x0000 | 0X00, 0X00, 0X001F, 0X0000, 0X0000}, |
| 0x3030 | 0 | 0X0000 | 0X00 | 0X0000 | 0X00 | 0X00 | 0X0101 | 0x2020 | 313 | 0X00, 0X00, 0X0101, 0x2020, 313}, |
| 0x3031 | 0 | 0X0000 | 0X00 | 0X0000 | 0X00 | 0X00 | 0X0101 | 0x2020 | 187 | 0X00, 0X00, 0X0101, 0x2020, 187}, |
| 0x3032 | 0 | 0X0000 | 0X00 | 0X0000 | 0X00 | 0X00 | 0X0101 | 0x2020 | 197 | 0X00, 0X00, 0X0101, 0x2020, 197}, |
| 0x3033 | 0 | 0X0000 | 0X00 | 0X0000 | 0X00 | 0X00 | 0X0101 | 0x2020 | 224 | 0X00, 0X00, 0X0101, 0x2020, 224}, |
| 0x3034 | 0 | 0X0000 | 0X00 | 0X0000 | 0X00 | 0X00 | 0X0101 | 0x2020 | 252 | 0X00, 0X00, 0X0101, 0x2020, 252}, |
| 0x3035 | 0 | 0X0000 | 0X00 | 0X0000 | 0X00 | 0X00 | 0X0101 | 0x2020 | 328 | 0X00, 0X00, 0X0101, 0x2020, 328}, |
| 0x3130 | 0 | 0X0000 | 0X00 | 0X0000 | 0X00 | 0X00 | 0X0101 | 0x2020 | 283 | 0X00, 0X00, 0X0101, 0x2020, 283}, |
| 0x3131 | 0 | 0X0000 | 0X00 | 0X0000 | 0X00 | 0X00 | 0X0101 | 0x2020 | 285 | 0X00, 0X00, 0X0101, 0x2020, 285}, |
| 0x3132 | 0 | 0X0000 | 0X00 | 0X0000 | 0X00 | 0X00 | 0X0101 | 0x2020 | 287 | 0X00, 0X00, 0X0101, 0x2020, 287}, |
| 0x3230 | 0 | 0X0000 | 0X00 | 0X0000 | 0X00 | 0X00 | 0X0101 | 0x2020 | 289 | 0X00, 0X00, 0X0101, 0x2020, 289}, |
| 0x3231 | 0 | 0X0000 | 0X00 | 0X0000 | 0X00 | 0X00 | 0X0101 | 0x2020 | 291 | 0X00, 0X00, 0X0101, 0x2020, 291}, |
| 0x3232 | 0 | 0X0000 | 0X00 | 0X0000 | 0X00 | 0X00 | 0X0101 | 0x2020 | 293 | 0X00, 0X00, 0X0101, 0x2020, 293}, |
| 0x3233 | 0 | 0X0000 | 0X00 | 0X0000 | 0X00 | 0X00 | 0X0101 | 0x2020 | 295 | 0X00, 0X00, 0X0101, 0x2020, 295}, |
| 0x3234 | 0 | 0X0000 | 0X00 | 0X0000 | 0X00 | 0X00 | 0X0101 | 0x2020 | 297 | 0X00, 0X00, 0X0101, 0x2020, 297}, |
| 0x3235 | 0 | 0X0000 | 0X00 | 0X0000 | 0X00 | 0X00 | 0X0101 | 0x2020 | 299 | 0X00, 0X00, 0X0101, 0x2020, 299}, |
| 0x3236 | 0 | 0X0000 | 0X00 | 0X0000 | 0X00 | 0X00 | 0X0101 | 0x2020 | 301 | 0X00, 0X00, 0X0101, 0x2020, 301}, |
| 0x3237 | 0 | 0X0000 | 0X00 | 0X0000 | 0X00 | 0X00 | 0X0101 | 0x2020 | 303 | 0X00, 0X00, 0X0101, 0x2020, 303}, |
| 0x3238 | 0 | 0X0000 | 0X00 | 0X0000 | 0X00 | 0X00 | 0X0101 | 0x2020 | 305 | 0X00, 0X00, 0X0101, 0x2020, 305}, |
| 0x3239 | 0 | 0X0000 | 0X00 | 0X0000 | 0X00 | 0X00 | 0X0101 | 0x2020 | 307 | 0X00, 0X00, 0X0101, 0x2020, 307}, |
| 0x3241 | 0 | 0X0000 | 0X00 | 0X0000 | 0X00 | 0X00 | 0X0101 | 0x2020 | 309 | 0X00, 0X00, 0X0101, 0x2020, 309}, |
| 0x3242 | 0 | 0X0000 | 0X00 | 0X0000 | 0X00 | 0X00 | 0X0101 | 0x2020 | 311 | 0X00, 0X00, 0X0101, 0x2020, 311}, |
| 0X0000 | 0 | 0X0000 | 0X00 | 0X0000 | 0X00 | 0X00 | 0X0000 | 0X0101 | 163 | 0X00, 0X00, 0X0000, 0X0101, 163}, |
| 0X0000 | 0x8B | 0X0000 | 0X00 | 0X0000 | 0X00 | 0X00 | 0X0101 | 0X0000 | 0X0000 | 0X00, 0X00, 0X0101, 0X0000, 0X0000}, |
| 0x3130 | 0 | 0x2000 | 0x04 | 0X0000 | 0X00 | 0X00 | 0X001F | 0x0000 | 0x0000 | 0X00, 0X00, 0X001F, 0X0000, 0X0000}, |
| 0X0000 | 0 | 0X0032 | 0x42 | 0X0000 | 0X00 | 0X00 | 0X001F | 0x0000 | 0x0000 | 0X00, 0X00, 0X001F, 0X0000, 0X0000}, |

FIG. 8E1

| STATE INDEX | STATE DESCRIPTION | SPACMD | FBACMD | STMCMD | OBACMD | SPASTAT | FBASTAT | STMSTAT | OBASTAT |
|---|---|---|---|---|---|---|---|---|---|
| 190 | SEND STROBE SETTING TO SM | 0X0000 | 0X0000 | 0X0000 | 0X0000 | 0X00 | 0X00 | 0X00 | 0X00 |
| 191 | WAIT FOR "IMAGE PROCESSING IDLE" | 0X0000 | 0X0000 | 0X0000 | 0X0000 | 0X00 | 0X00 | 0X00 | 0X00 |
| 192 | CAPTURE BACKGROUNDS FOR LIGHT LEVEL | 0X0000 | 0X0000 | 0X0000 | 0X0000 | 0X00 | 0X00 | 0X00 | 0X00 |
| 193 | WAITFORSMTOBEDONEWITHBACKGROUNDS: WAIT FOR SM TO BE DONE WITH LIGHT LEVEL BACKGROUNDS | 0X0000 | 0X0000 | 0X0000 | 0X0000 | 0X00 | 0X00 | 0X00 | 0X00 |
| 194 | IF SM REPLIES '00' BRANCH TO "HANDLE STROBE"; ELSE FALL THROUGH | 0X0000 | 0X0000 | 0X0000 | 0X0000 | 0X00 | 0X00 | 0X00 | 0X00 |
| 195 | SEND COMPLETION SIGNAL TO HOST | 0X0000 | 0X0000 | 0X0000 | 0X0000 | 0X00 | 0X00 | 0X00 | 0X00 |
| 196 | BRANCH TO AUTOFOCUSREADYFORCOMMAND | 0X0000 | 0X0000 | 0X0000 | 0X0000 | 0X00 | 0X00 | 0X00 | 0X00 |
| 197 | AUTOFOCUSCOARSE: RETRIEVE CONTROL ID (BAR CODE) | 0X0000 | 0X0000 | 0X0707 | 0X0000 | 0X00 | 0X00 | 0X00 | 0X00 |
| 198 | GET SAMPLE INFO FROM HOST | 0X0000 | 0X0000 | 0X0000 | 0X0000 | 0X00 | 0X00 | 0X00 | 0X00 |
| 199 | IF SM REPLIES '00', BRANCH TO "MOVE TO NEXT CONTROL TUBEPOSITION (AF)" | 0X0000 | 0X0000 | 0X0000 | 0X0000 | 0X00 | 0X00 | 0X00 | 0X00 |
| 200 | IF SM REPLIES '-2', BRANCH TO "OE" (CLEAR RACK) | 0X0000 | 0X0000 | 0X0000 | 0X0000 | 0X00 | 0X00 | 0X00 | 0X00 |
| 201 | WAIT FOR "IMAGE PROCESSING IDLE" | 0X0000 | 0X0000 | 0X0000 | 0X0000 | 0X00 | 0X00 | 0X00 | 0X00 |
| 202 | START SHEATH FOR BACKGROUND CAPTURE | SB | 0X0000 | 0X0000 | 0X0000 | 0X31 | 0X00 | 0X00 | 0X00 |
| 203 | WAIT FOR SB COMPLETE | 0X0000 | 0X0000 | 0X0000 | 0X0000 | 0XFF | 0X00 | 0X00 | 0X00 |
| 204 | TIMER DELAY BEFORE CAPTURE | 0X0000 | 0X0000 | 0X0000 | 0X0000 | 0X00 | 0X00 | 0X00 | 0X00 |
| 205 | CAPTURE BACKGROUND AND WAIT FOR FRAME PROCESSING COMPLETE (FUTURE WAIT FOR FRAME CAPTURE COMPLETE) OR SHORT SAMPLE DETECTOR | 0X0000 | 0X0000 | 0X0000 | 0X0000 | 0X00 | 0X00 | 0X00 | 0X00 |
| 206 | SEND "SHORT SAMPLE" MESSAGE AND WAIT FOR FRAME PROCESSING COMPLETE (FUTURE WAIT FOR FRAME CAPTURE COMPLETE). IF EXCEEDS 10 SECS - GOTO BX. | 0X0000 | 0X0000 | 0X0000 | 0X0000 | 0X00 | 0X00 | 0X00 | 0X00 |
| 207 | TURN OFF EP PUMP ON SPA | EB | 0X0000 | 0X0000 | 0X0000 | 0X34 | 0X00 | 0X00 | 0X00 |
| 208 | WAIT FOR EB COMPLETE | 0X0000 | 0X0000 | 0X0000 | 0X0000 | 0XFF | 0X00 | 0X00 | 0X00 |
| 209 | INITIAL OFFSET A (COARSE) | 0X0000 | 0X0000 | 0X0000 | IA | 0X00 | 0X00 | 0X00 | 0X33 |
| 210 | WAIT FOR OBA BACK TO IDLE | 0X0000 | 0X0000 | 0X0000 | 0X0000 | 0X00 | 0X00 | 0X00 | 0XFF |
| 211 | WAIT FOR "IMAGE PROCESSING IDLE" | 0X0000 | 0X0000 | 0X0000 | 0X0000 | 0X00 | 0X00 | 0X00 | 0X00 |
| 212 | START ASPIRATION FOR SAMPLE TRANSFER | AS | RC | 0X0000 | 0X0000 | 0X17 | 0X00 | 0X00 | 0X00 |
| 213 | WAIT FOR AS AND RC COMPLETE | 0X0000 | 0X0000 | 0X0000 | 0X0000 | 0XFF | 0XFF | 0X00 | 0X00 |
| 214 | TIMER DELAY BEFORE CAPTURE | 0X0000 | 0X0000 | 0X0000 | 0X0000 | 0X00 | 0X00 | 0X00 | 0X00 |
| 215 | COARSEFW1_AF | 0X0000 | 0X0000 | 0X0000 | NA | 0X00 | 0X28 | 0X00 | 0X33 |
| 216 | WAIT FOR OBA BACK TO IDLE | 0X0000 | 0X0000 | 0X0000 | 0X0000 | 0X00 | 0X00 | 0X00 | 0XFF |
| 217 | CAPTURE SAMPLE FRAMES ("SMCSATNEXTAUTOFOCUSPOSITION") AND WAIT FOR SAMPLE FRAME CAPTURE COMPLETE OR SHORT SAMPLE DETECTOR | 0X0000 | 0X0000 | 0X0000 | 0X0000 | 0X00 | 0X00 | 0X00 | 0X00 |
| 218 | SEND "SHORT SAMPLE" MESSAGE AND WAIT FOR SAMPLE FRAME CAPTURE COMPLETE | 0X0000 | 0X0000 | 0X0000 | 0X0000 | 0X00 | 0X00 | 0X00 | 0X00 |
| 219 | IF SM ARGUMENT TO "DONEGATHERINGIMAGES" IS '00' BRANCH TO FORWARD1ONFOCUSMOTOR; ELSE FALL THROUGH | 0X0000 | 0X0000 | 0X0000 | 0X0000 | 0X00 | 0X00 | 0X00 | 0X00 |
| 220 | SEND COMPLETION SIGNAL TO HOST | 0X0000 | 0X0000 | 0X0000 | 0X0000 | 0X00 | 0X00 | 0X00 | 0X00 |
| 221 | HOME PUMPS | HC | HC | 0X0000 | 0X0000 | 0X27 | 0X00 | 0X00 | 0X00 |
| 222 | WAIT FOR AS AND RC COMPLETE | 0X0000 | 0X0000 | 0X0000 | 0X0000 | 0XFF | 0XFF | 0X00 | 0X00 |
| 223 | BRANCH TO AUTOFOCUSREADYFORCOMMAND | 0X0000 | 0X0000 | 0X0000 | 0X0000 | 0X00 | 0X00 | 0X00 | 0X00 |
| 224 | AUTOFOCUSPEAK: RETRIEVE CONTROL ID (BAR CODE) | 0X0000 | 0X0000 | 0X0707 | 0X0000 | 0X00 | 0X00 | 0X00 | 0X00 |
| 225 | GET SAMPLE INFO FROM HOST | 0X0000 | 0X0000 | 0X0000 | 0X0000 | 0X00 | 0X00 | 0X00 | 0X00 |
| 226 | IF SM REPLIES '00', BRANCH TO "MOVE TO NEXT CONTROL TUBE POSITION (AF)" | 0X0000 | 0X0000 | 0X0000 | 0X0000 | 0X00 | 0X00 | 0X00 | 0X00 |
| 227 | IF SM REPLIES '-2', BRANCH TO "OE" (CLEAR RACK) | 0X0000 | 0X0000 | 0X0000 | 0X0000 | 0X00 | 0X00 | 0X00 | 0X00 |
| 228 | WAIT FOR "IMAGE PROCESSING IDLE" | 0X0000 | 0X0000 | 0X0000 | 0X0000 | 0X00 | 0X00 | 0X00 | 0X00 |
| 229 | START SHEATH FOR BACKGROUND CAPTURE | SB | 0X0000 | 0X0000 | 0X0000 | 0X31 | 0X00 | 0X00 | 0X00 |
| 230 | WAIT FOR SB COMPLETE | 0X0000 | 0X0000 | 0X0000 | 0X0000 | 0XFF | 0X00 | 0X00 | 0X00 |
| 231 | TIMER DELAY BEFORE CAPTURE | 0X0000 | 0X0000 | 0X0000 | 0X0000 | 0X00 | 0X00 | 0X00 | 0X00 |

FIG. 8E2

| SMTST | TOSM | TVALUE | TFUNC | SENS | STST | SMSK | END | BRAN | DEST | TRANSLATED PARAMETERS |
|---|---|---|---|---|---|---|---|---|---|---|
| 0X0000 | 0x8B | 0X0000 | 0X00 | 0X0000 | 0X00 | 0X00 | 0x0101 | 0X0000 | 0X0000 | 0X00, 0X00, 0x0101, 0X0000, 0X0000} |
| 0x3338 | 0X37 | 0X0000 | 0x00 | 0X0000 | 0X00 | 0X00 | 0X001F | 0X0000 | 0X0000 | 0X00, 0X00, 0X001F, 0X0000, 0X0000} |
| 0x0000 | 0X83 | 0x0000 | 0x00 | 0x0000 | 0x00 | 0x00 | 0x0101 | 0x0000 | 0x0000 | 0x00, 0x00, 0x0101, 0x0000, 0x0000} |
| 0X3034 | 0 | 0x0000 | 0x00 | 0X0000 | 0x00 | 0x00 | 0X0010 | 0x0000 | 0x0000 | 0x00, 0x00, 0X0010, 0x0000, 0x0000} |
| 0X3030 | 0 | 0X0000 | 0X00 | 0X0000 | 0X00 | 0X00 | 0X0101 | 0X0020 | 279 | 0X00, 0X00, 0X0101, 0X0020, 279} |
| 0x0000 | 0x87 | 0X0000 | 0X0000 | 0X0000 | 0X00 | 0X00 | 0X0101 | 0X0000 | 0X0000 | 0X00, 0X00, 0X0101, 0X0000, 0X0000} |
| 0X0000 | 0 | 0X0000 | 0X00 | 0X0000 | 0X00 | 0X00 | 0X0000 | 0X0101 | 163 | 0X00, 0X00, 0X0000, 0X0101, 163} |
| 0X0000 | 0 | 0X002F | 0x44 | 0X0000 | 0X00 | 0X00 | 0X0101 | 0X0000 | 0X0000 | 0X00, 0X00, 0X0101, 0X0000, 0X0000} |
| 0X3032 | 0x81 | 0X0030 | 0x44 | 0X0000 | 0X00 | 0X00 | 0X001F | 0X0000 | 0X0000 | 0X00, 0X00, 0X001F, 0X0000, 0X0000} |
| 0X3030 | 0 | 0X0000 | 0X00 | 0X0000 | 0X00 | 0X00 | 0X0101 | 0X0020 | 326 | 0X00, 0X00, 0X0101, 0X0020, 326} |
| 0X2D32 | 0 | 0X0000 | 0X00 | 0X0000 | 0X00 | 0X00 | 0X0101 | 0X0020 | 0x3045 | 0X00, 0X00, 0X0101, 0X0020, 0x3045} |
| 0x3338 | 0x37 | 0X0000 | 0x00 | 0X0000 | 0X00 | 0X00 | 0X001F | 0X0000 | 0X0000 | 0X00, 0X00, 0X001F, 0X0000, 0X0000} |
| 0X0000 | 0 | 0X0000 | 0X00 | 0X0000 | 0X00 | 0X00 | 0x001F | 0X0000 | 0X0000 | 0X00, 0X00, 0x001F, 0X0000, 0X0000} |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000} |
| 0X0000 | 0 | 0X0018 | 0x42 | 0X0000 | 0x00 | 0x00 | 0X0000 | 0x0000 | 0X0000 | 0x00, 0x00, 0X0000, 0x0000, 0X0000} |
| 0X3034 | 0X83 | 0x0000 | 0x00 | 0x0032 | 0x00 | 0x02 | 0x0001 | 0x0010 | 207 | 0x00, 0x02, 0x0001, 0x0010, 207} |
| 0X3034 | 0x31 | 0x0019 | 0x43 | 0X0000 | 0x00 | 0x00 | 0X0010 | 0x0000 | 0x4258 | 0x00, 0x00, 0X0010, 0x0000, 0x4258} |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000} |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000} |
| 0X0000 | 0 | 0X003B | 0x44 | 0X0000 | 0X00 | 0X00 | 0x0040 | 0X0000 | 0X0000 | 0X00, 0X00, 0x0040, 0X0000, 0X0000} |
| 0X0000 | 0 | 0X003B | 0x44 | 0X0000 | 0X00 | 0X00 | 0x0040 | 0X0000 | 0X0000 | 0X00, 0X00, 0x0040, 0X0000, 0X0000} |
| 0x3338 | 0x37 | 0X0000 | 0x00 | 0X0000 | 0X00 | 0X00 | 0X001F | 0X0000 | 0X0000 | 0X00, 0X00, 0X001F, 0X0000, 0X0000} |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000} |
| 0X0000 | 0 | 0X0000 | 0X00 | 0X0000 | 0X00 | 0X00 | 0x8606 | 0X0000 | 0X0000 | 0X00, 0X00, 0x8606, 0X0000, 0X0000} |
| 0X0000 | 0 | 0X0062 | 0x42 | 0X0000 | 0x00 | 0x00 | 0X0000 | 0x0000 | 0X0000 | 0x00, 0x00, 0X0000, 0x0000, 0X0000} |
| 0X0000 | 0 | 0X0041 | 0x44 | 0X0000 | 0X00 | 0X00 | 0x0040 | 0X0000 | 0X0000 | 0X00, 0X00, 0x0040, 0X0000, 0X0000} |
| 0X0000 | 0 | 0x2000 | 0x04 | 0X0000 | 0X00 | 0X00 | 0x0040 | 0X0000 | 0X0000 | 0X00, 0X00, 0x0040, 0X0000, 0X0000} |
| 0X3036 | 0X8D | 0x0000 | 0x00 | 0x0032 | 0X00 | 0x02 | 0x0001 | 0x0010 | 219 | 0X00, 0x02, 0x0001, 0x0010, 219} |
| 0X3036 | 0x31 | 0X0063 | 0x43 | 0X0000 | 0X00 | 0X00 | 0X0010 | 0X0000 | 0X4258 | 0X00, 0X00, 0X0010, 0X0000, 0X4258} |
| 0X3030 | 0 | 0X0000 | 0X00 | 0X0000 | 0X00 | 0X00 | 0X0101 | 0X0020 | 215 | 0X00, 0X00, 0X0101, 0X0020, 215} |
| 0x0000 | 0x87 | 0X0000 | 0X00 | 0X0000 | 0X00 | 0X00 | 0X0101 | 0X0000 | 0X0000 | 0X00, 0X00, 0X0101, 0X0000, 0X0000} |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000} |
| 0X0000 | 0 | 0X0000 | 0X00 | 0X0000 | 0X00 | 0X00 | 0x8606 | 0X0000 | 0X0000 | 0X00, 0X00, 0x8606, 0X0000, 0X0000} |
| 0X0000 | 0 | 0X0000 | 0X00 | 0X0000 | 0X00 | 0X00 | 0X0000 | 0X0101 | 163 | 0X00, 0X00, 0X0000, 0X0101, 163} |
| 0X0000 | 0 | 0X002F | 0x44 | 0X0000 | 0X00 | 0X00 | 0X0101 | 0X0000 | 0X0000 | 0X00, 0X00, 0X0101, 0X0000, 0X0000} |
| 0X3032 | 0x81 | 0X0030 | 0x44 | 0X0000 | 0X00 | 0X00 | 0X001F | 0X0000 | 0X0000 | 0X00, 0X00, 0X001F, 0X0000, 0X0000} |
| 0X3030 | 0 | 0X0000 | 0X00 | 0X0000 | 0X00 | 0X00 | 0X0101 | 0X0020 | 326 | 0X00, 0X00, 0X0101, 0X0020, 326} |
| 0X2D32 | 0 | 0X0000 | 0X00 | 0X0000 | 0X00 | 0X00 | 0X0101 | 0X0020 | 0x3045 | 0X00, 0X00, 0X0101, 0X0020, 0x3045} |
| 0x3338 | 0x37 | 0X0000 | 0x00 | 0X0000 | 0X00 | 0X00 | 0X001F | 0X0000 | 0X0000 | 0X00, 0X00, 0X001F, 0X0000, 0X0000} |
| 0X0000 | 0 | 0X0000 | 0X00 | 0X0000 | 0X00 | 0X00 | 0x001F | 0X0000 | 0X0000 | 0X00, 0X00, 0x001F, 0X0000, 0X0000} |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000} |
| 0X0000 | 0 | 0X0018 | 0x42 | 0X0000 | 0x00 | 0x00 | 0X0000 | 0x0000 | 0X0000 | 0x00, 0x00, 0X0000, 0x0000, 0X0000} |

FIG. 8F1

| STATE INDEX | STATE DESCRIPTION | SPACMD | FBACMD | STMCMD | OBACMD | SPASTAT | FBASTAT | STMSTAT | OBASTAT |
|---|---|---|---|---|---|---|---|---|---|
| 232 | CAPTURE BACKGROUND AND WAIT FOR FRAME PROCESSING COMPLETE (FUTURE WAIT FOR FRAME CAPTURE COMPLETE) OR SHORT SAMPLE DETECTOR. | 0X0000 | 0X0000 | 0X0000 | 0X0000 | 0x00 | 0x00 | 0x00 | 0x00 |
| 233 | SEND "SHORT SAMPLE" MESSAGE AND WAIT FOR FRAME PROCESSING COMPLETE (FUTURE WAIT FOR FRAME CAPTURE COMPLETE). IF EXCEEDS 10 SECS - GOTO BX. | 0X0000 | 0X0000 | 0X0000 | 0X0000 | 0x00 | 0x00 | 0x00 | 0x00 |
| 234 | TURN OFF EP PUMP ON SPA | EB | 0X0000 | 0X0000 | 0X0000 | 0x34 | 0x00 | 0X00 | 0X00 |
| 235 | WAIT FOR EB COMPLETE | 0X0000 | 0X0000 | 0X0000 | 0X0000 | 0xFF | 0x00 | 0X00 | 0X00 |
| 236 | IF SM REPLIES '-1' BRANCH TO "END"; ELSE FALL THROUGH | 0X0000 | 0X0000 | 0X0000 | 0X0000 | 0X00 | 0X00 | 0X00 | 0X00 |
| 237 | INITIAL OFFSET B (PEAK) | 0X0000 | 0X0000 | 0X0000 | IB | 0X00 | 0X00 | 0X00 | 0x33 |
| 238 | WAIT FOR OBA BACK TO IDLE | 0X0000 | 0X0000 | 0X0000 | 0x0000 | 0X00 | 0X00 | 0X00 | 0xFF |
| 239 | WAIT FOR "IMAGE PROCESSING IDLE" | 0X0000 | 0X0000 | 0X0000 | 0X0000 | 0x00 | 0x00 | 0X00 | 0X00 |
| 240 | START ASPIRATION FOR SAMPLE TRANSFER | AS | RC | 0X0000 | 0X0000 | 0x17 | 0x00 | 0X00 | 0X00 |
| 241 | WAIT FOR AS AND RC COMPLETE | 0X0000 | 0X0000 | 0X0000 | 0X0000 | 0xFF | 0xFF | 0X00 | 0X00 |
| 242 | TIMER DELAY BEFORE CAPTURE | 0X0000 | 0X0000 | 0X0000 | 0X0000 | 0x00 | 0x00 | 0x00 | 0x00 |
| 243 | PEAKFW1 AF | 0X0000 | 0X0000 | 0X0000 | NB | 0X00 | 0x28 | 0X00 | 0x33 |
| 244 | WAIT FOR OBA BACK TO IDLE | 0X0000 | 0X0000 | 0X0000 | 0x0000 | 0X00 | 0X00 | 0X00 | 0xFF |
| 245 | CAPTURE SAMPLE FRAMES ("SMCSATNEXTAUTOFOCUSPOSITION") AND WAIT FOR SAMPLE FRAME CAPTURE COMPLETE OR SHORT SAMPLE | 0X0000 | 0X0000 | 0X0000 | 0X0000 | 0x00 | 0X00 | 0X00 | 0X00 |
| 246 | SEND "SHORT SAMPLE" MESSAGE AND WAIT FOR SAMPLE FRAME CAPTURE COMPLETE | 0X0000 | 0X0000 | 0X0000 | 0X0000 | 0x00 | 0X00 | 0X00 | 0X00 |
| 247 | IF SM ARGUMENT TO "DONEGATHERINGIMAGES" IS "00" BRANCH TO FORWARDIONFOCUSMOTOR; ELSE FALL THROUGH | 0X0000 | 0X0000 | 0X0000 | 0X0000 | 0X00 | 0X00 | 0X00 | 0X00 |
| 248 | SEND COMPLETION SIGNAL TO HOST | 0X0000 | 0X0000 | 0X0000 | 0X0000 | 0X00 | 0X00 | 0X00 | 0X00 |
| 249 | HOME PUMPS | HC | HC | 0X0000 | 0X0000 | 0x27 | 0x00 | 0X00 | 0X00 |
| 250 | WAIT FOR AS AND RC COMPLETE | 0X0000 | 0X0000 | 0X0000 | 0X0000 | 0xFF | 0xFF | 0X00 | 0X00 |
| 251 | BRANCH TO AUTOFOCUSREADYFORCOMMAND | 0X0000 | 0X0000 | 0X0000 | 0X0000 | 0X00 | 0X00 | 0X00 | 0X00 |
| 252 | AUTOFOCUSCLINICAL: RETRIEVE CONTROL ID (BAR CODE) | 0X0000 | 0X0000 | 0X0707 | 0X0000 | 0X00 | 0X00 | 0X00 | 0X00 |
| 253 | GET SAMPLE INFO FROM HOST | 0X0000 | 0X0000 | 0X0000 | 0X0000 | 0X00 | 0X00 | 0X00 | 0X00 |
| 254 | IF SM REPLIES '00', BRANCH TO "MOVE TO NEXT CONTROL TUBE POSITION (AF)" | 0X0000 | 0X0000 | 0X0000 | 0X0000 | 0X00 | 0X00 | 0X00 | 0X00 |
| 255 | IF SM REPLIES '-2', BRANCH TO "OE" (CLEAR RACK) | 0X0000 | 0X0000 | 0X0000 | 0X0000 | 0X00 | 0X00 | 0X00 | 0X00 |
| 256 | WAIT FOR "IMAGE PROCESSING IDLE" | 0X0000 | 0X0000 | 0X0000 | 0X0000 | 0x00 | 0X00 | 0X00 | 0X00 |
| 257 | START SHEATH FOR BACKGROUND CAPTURE | SB | 0X0000 | 0X0000 | 0X0000 | 0x31 | 0X00 | 0X00 | 0X00 |
| 258 | WAIT FOR SB COMPLETE | 0X0000 | 0X0000 | 0X0000 | 0X0000 | 0xFF | 0x00 | 0X00 | 0X00 |
| 259 | TIMER DELAY BEFORE CAPTURE | 0X0000 | 0X0000 | 0X0000 | 0X0000 | 0x00 | 0x00 | 0x00 | 0x00 |
| 260 | CAPTURE BACKGROUND AND WAIT FOR FRAME PROCESSING COMPLETE (FUTURE WAIT FOR FRAME CAPTURE COMPLETE) OR SHORT SAMPLE DETECTOR. | 0X0000 | 0X0000 | 0X0000 | 0X0000 | 0x00 | 0x00 | 0x00 | 0x00 |
| 261 | SEND "SHORT SAMPLE" MESSAGE AND WAIT FOR FRAME PROCESSING COMPLETE (FUTURE WAIT FOR FRAME CAPTURE COMPLETE). IF EXCEEDS 10 SECS - GOTO BX. | 0X0000 | 0X0000 | 0X0000 | 0X0000 | 0x00 | 0x00 | 0x00 | 0x00 |
| 262 | TURN OFF EP PUMP ON SPA | EB | 0X0000 | 0X0000 | 0X0000 | 0x34 | 0x00 | 0X00 | 0X00 |
| 263 | WAIT FOR EB COMPLETE | 0X0000 | 0X0000 | 0X0000 | 0X0000 | 0xFF | 0x00 | 0X00 | 0X00 |
| 264 | IF SM REPLIES '-1' BRANCH TO "END"; ELSE FALL THROUGH | 0X0000 | 0X0000 | 0X0000 | 0X0000 | 0X00 | 0X00 | 0X00 | 0X00 |
| 265 | INITIAL OFFSET C (CLINICAL) | 0X0000 | 0X0000 | 0X0000 | IC | 0X00 | 0X00 | 0X00 | 0x33 |
| 266 | WAIT FOR OBA BACK TO IDLE | 0X0000 | 0X0000 | 0X0000 | 0x0000 | 0X00 | 0X00 | 0X00 | 0xFF |
| 267 | START ASPIRATION FOR SAMPLE TRANSFER | AS | RC | 0X0000 | 0X0000 | 0x17 | 0x00 | 0X00 | 0X00 |
| 268 | WAIT FOR AS AND RC COMPLETE | 0X0000 | 0X0000 | 0X0000 | 0X0000 | 0xFF | 0xFF | 0X00 | 0X00 |
| 269 | TIMER DELAY BEFORE CAPTURE | 0X0000 | 0X0000 | 0X0000 | 0X0000 | 0x00 | 0x00 | 0x00 | 0x00 |
| 270 | CLINICALFW1 AF | 0X0000 | 0X0000 | 0X0000 | NC | 0X00 | 0x28 | 0X00 | 0x33 |
| 271 | WAIT FOR OBA BACK TO IDLE | 0X0000 | 0X0000 | 0X0000 | 0x0000 | 0X00 | 0X00 | 0X00 | 0xFF |

FIG. 8F2

| SMTST | TOSM | TVALUE | TFUNC | SENS | STST | SMSK | END | BRAN | DEST | TRANSLATED PARAMETERS |
|---|---|---|---|---|---|---|---|---|---|---|
| 0X3034 | 0X83 | 0x0000 | 0x00 | 0x0032 | 0x00 | 0x02 | 0x0001 | 0x0010 | 234 | 0x00, 0x02, 0x0001, 0x0010, 234}, |
| 0X3034 | 0x31 | 0X0019 | 0x43 | 0X0000 | 0X00 | 0X00 | 0X0010 | 0x0000 | 0x4258 | 0x00, 0x00, 0X0010, 0x0000, 0x4258}, |
| 0X0000 | | 0 | 0X0000 | 0X00 | 0X0000 | 0X00 | 0X00 | 0x001F | 0X0000 | 0X0000 | 0X00, 0X00, 0x001F, 0X0000, 0X0000}, |
| 0X0000 | | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0x2D31 | | 0 | 0X0000 | 0X00 | 0X0000 | 0X00 | 0X00 | 0X0101 | 0X0020 | 335 | 0X00, 0X00, 0X0101, 0X0020, 335}, |
| 0X0000 | | 0 | 0X003B | 0x44 | 0X0000 | 0X00 | 0X00 | 0x0040 | 0X0000 | 0X0000 | 0X00, 0X00, 0x0040, 0X0000, 0X0000}, |
| 0X0000 | | 0 | 0X003B | 0x44 | 0X0000 | 0X00 | 0X00 | 0x0040 | 0X0000 | 0X0000 | 0X00, 0X00, 0x0040, 0X0000, 0X0000}, |
| 0x3338 | 0x37 | 0X0000 | 0x00 | 0X0000 | 0X00 | 0X00 | 0X001F | 0X0000 | 0X0000 | 0X00, 0X00, 0X001F, 0X0000, 0X0000}, |
| 0X0000 | | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | | 0 | 0X0000 | 0X00 | 0X0000 | 0X00 | 0X00 | 0x8606 | 0X0000 | 0X0000 | 0X00, 0X00, 0x8606, 0X0000, 0X0000}, |
| 0X0000 | | 0 | 0X0062 | 0x42 | 0X0000 | 0x00 | 0x00 | 0X0000 | 0x0000 | 0X0000 | 0x00, 0x00, 0X0000, 0x0000, 0X0000}, |
| 0X0000 | | 0 | 0X0041 | 0x44 | 0X0000 | 0X00 | 0X00 | 0x0040 | 0X0000 | 0X0000 | 0X00, 0X00, 0x0040, 0X0000, 0X0000}, |
| 0X0000 | | 0 | 0X003B | 0x44 | 0X0000 | 0X00 | 0X00 | 0x0040 | 0X0000 | 0X0000 | 0X00, 0X00, 0x0040, 0X0000, 0X0000}, |
| 0X3036 | 0X8D | 0x0000 | 0x00 | 0x0032 | 0X00 | 0x02 | 0x0001 | 0x0010 | 247 | 0X00, 0x02, 0x0001, 0x0010, 247}, |
| 0X3036 | 0x31 | 0X0063 | 0x43 | 0X0000 | 0X00 | 0X00 | 0X0010 | 0x0000 | 0X4258 | 0X00, 0X00, 0X0010, 0X0000, 0X4258}, |
| 0X3030 | | 0 | 0X0000 | 0X00 | 0X0000 | 0X00 | 0X00 | 0X0101 | 0X0020 | 243 | 0X00, 0X00, 0X0101, 0X0020, 243}, |
| 0x0000 | 0x87 | 0X0000 | 0X00 | 0X0000 | 0X00 | 0X00 | 0X0101 | 0X0000 | 0X0000 | 0X00, 0X00, 0X0101, 0X0000, 0X0000}, |
| 0X0000 | | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | | 0 | 0X0000 | 0X00 | 0X0000 | 0X00 | 0X00 | 0x8606 | 0X0000 | 0X0000 | 0X00, 0X00, 0x8606, 0X0000, 0X0000}, |
| 0X0000 | | 0 | 0X0000 | 0X00 | 0X0000 | 0X00 | 0X00 | 0X0000 | 0X0101 | 163 | 0X00, 0X00, 0X0000, 0X0101, 163}, |
| 0X0000 | | 0 | 0X002F | 0x44 | 0X0000 | 0X00 | 0X00 | 0X0101 | 0X0000 | 0X0000 | 0X00, 0X00, 0X0101, 0X0000, 0X0000}, |
| 0X3032 | 0x81 | 0X0030 | 0x44 | 0X0000 | 0X00 | 0X00 | 0X001F | 0X0000 | 0X0000 | 0X00, 0X00, 0X001F, 0X0000, 0X0000}, |
| 0X3030 | | 0 | 0X0000 | 0X00 | 0X0000 | 0X00 | 0X00 | 0X0101 | 0X0020 | 326 | 0X00, 0X00, 0X0101, 0X0020, 326}, |
| 0X2D32 | | 0 | 0X0000 | 0X00 | 0X0000 | 0X00 | 0X00 | 0X0101 | 0X0020 | 0X3045 | 0X00, 0X00, 0X0101, 0X0020, 0x3045}, |
| 0X3338 | 0x37 | 0X0000 | 0x00 | 0X0000 | 0X00 | 0X00 | 0X001F | 0X0000 | 0X0000 | 0X00, 0X00, 0X001F, 0X0000, 0X0000}, |
| 0X0000 | | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | | 0 | 0X0018 | 0x42 | 0X0000 | 0x00 | 0x00 | 0X0000 | 0X0000 | 0X0000 | 0x00, 0x00, 0X0000, 0X0000, 0X0000}, |
| 0X3034 | 0X83 | 0x0000 | 0x00 | 0x0032 | 0x00 | 0x02 | 0x0001 | 0x0010 | 262 | 0x00, 0x02, 0x0001, 0x0010, 262}, |
| 0X3034 | 0x31 | 0X0019 | 0x43 | 0X0000 | 0X00 | 0X00 | 0X0010 | 0x0000 | 0x4258 | 0x00, 0x00, 0X0010, 0x0000, 0x4258}, |
| 0X0000 | | 0 | 0X0000 | 0X00 | 0X0000 | 0X00 | 0X00 | 0x001F | 0X0000 | 0X0000 | 0X00, 0X00, 0x001F, 0X0000, 0X0000}, |
| 0X0000 | | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0x2D31 | | 0 | 0X0000 | 0X00 | 0X0000 | 0X00 | 0X00 | 0X0101 | 0X0020 | 335 | 0X00, 0X00, 0X0101, 0X0020, 335}, |
| 0X0000 | | 0 | 0X003B | 0x44 | 0X0000 | 0X00 | 0X00 | 0x0040 | 0X0000 | 0X0000 | 0X00, 0X00, 0x0040, 0X0000, 0X0000}, |
| 0X0000 | | 0 | 0X003B | 0x44 | 0X0000 | 0X00 | 0X00 | 0x0040 | 0X0000 | 0X0000 | 0X00, 0X00, 0x0040, 0X0000, 0X0000}, |
| 0X0000 | | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | | 0 | 0X0000 | 0X00 | 0X0000 | 0X00 | 0X00 | 0x8606 | 0X0000 | 0X0000 | 0X00, 0X00, 0x8606, 0X0000, 0X0000}, |
| 0X0000 | | 0 | 0X0062 | 0x42 | 0X0000 | 0x00 | 0x00 | 0X0000 | 0x0000 | 0X0000 | 0x00, 0x00, 0X0000, 0X0000, 0X0000}, |
| 0X0000 | | 0 | 0X0041 | 0x44 | 0X0000 | 0X00 | 0X00 | 0x0040 | 0X0000 | 0X0000 | 0X00, 0X00, 0x0040, 0X0000, 0X0000}, |
| 0X0000 | | 0 | 0X003B | 0x44 | 0X0000 | 0X00 | 0X00 | 0x0040 | 0X0000 | 0X0000 | 0X00, 0X00, 0x0040, 0X0000, 0X0000}, |

FIG. 8G1

| STATE INDEX | STATE DESCRIPTION | SPACMD | FBACMD | STMCMD | OBACMD | SPASTAT | FBASTAT | STMSTAT | OBASTAT |
|---|---|---|---|---|---|---|---|---|---|
| 272 | CAPTURE SAMPLE FRAMES ("SMCSATNEXTAUTOFOCUSPOSITION") AND WAIT FOR SAMPLE FRAME CAPTURE COMPLETE OR SHORT SAMPLE DETECTOR | 0X0000 | 0X0000 | 0X0000 | 0X0000 | 0x00 | 0X00 | 0X00 |
| 273 | SEND "SHORT SAMPLE" MESSAGE AND WAIT FOR SAMPLE FRAME CAPTURE COMPLETE | 0X0000 | 0X0000 | 0X0000 | 0X0000 | 0x00 | 0X00 | 0X00 |
| 274 | IF SM ARGUMENT TO "DONEGATHERINGIMAGES" IS '00' BRANCH TO FORWARD1ONFOCUSMOTOR; ELSE FALL THROUGH | 0X0000 | 0X0000 | 0X0000 | 0X0000 | 0X00 | 0X00 | 0X00 |
| 275 | SEND COMPLETION SIGNAL TO HOST | 0X0000 | 0X0000 | 0X0000 | 0X0000 | 0X00 | 0X00 | 0X00 |
| 276 | HOME PUMPS | HC | HC | 0X0000 | 0X0000 | 0x27 | 0x00 | 0X00 |
| 277 | WAIT FOR AS AND RC COMPLETE | 0X0000 | 0X0000 | 0X0000 | 0X0000 | 0xFF | 0xFF | 0X00 |
| 278 | BRANCH TO AUTOFOCUSREADYFORCOMMAND | 0X0000 | 0X0000 | 0X0000 | 0X0000 | 0X00 | 0X00 | 0X00 |
| 279 | HANDLESTROBE: WAIT FOR STROBE SETTING | 0X0000 | 0X0000 | 0X0000 | 0X0000 | 0X00 | 0X00 | 0X00 |
| 280 | PAUSE FOR IT TO TAKE EFFECT | 0X0000 | 0X0000 | 0X0000 | 0X0000 | 0X00 | 0X00 | 0X00 |
| 281 | SEND STROBE SETTING TO SM | 0X0000 | 0X0000 | 0X0000 | 0X0000 | 0X00 | 0X00 | 0X00 |
| 282 | BRANCH BACK TO WAITFORSMTOBEDONEWITHBACKGROUNDS | 0X0000 | 0X0000 | 0X0000 | 0X0000 | 0X00 | 0X00 | 0X00 |
| 283 | AUTOFOCUSCOARSEFINALOFFSET | 0X0000 | 0X0000 | 0X0000 | BA | 0X00 | 0X00 | 0X00 |
| 284 | WAIT FOR OBA AND BRANCH TO AUTOFOCUSREADYFORCOMMAND | 0X0000 | 0X0000 | 0X0000 | 0X0000 | 0X00 | 0X00 | 0X00 |
| 285 | AUTOFOCUSPEAKFINALOFFSET | 0X0000 | 0X0000 | 0X0000 | BB | 0X00 | 0X00 | 0X00 |
| 286 | WAIT FOR OBA AND BRANCH TO AUTOFOCUSREADYFORCOMMAND | 0X0000 | 0X0000 | 0X0000 | 0X0000 | 0X00 | 0X00 | 0X00 |
| 287 | AUTOFOCUSCLINICALFINALOFFSET | 0X0000 | 0X0000 | 0X0000 | BC | 0X00 | 0X00 | 0X00 |
| 288 | WAIT FOR OBA AND BRANCH TO AUTOFOCUSREADYFORCOMMAND | 0X0000 | 0X0000 | 0X0000 | 0X0000 | 0X00 | 0X00 | 0X00 |
| 289 | AUTOFOCUSFORWARD1 | 0X0000 | 0X0000 | 0X0000 | F0 | 0X00 | 0X00 | 0X00 |
| 290 | WAIT FOR OBA AND BRANCH TO AUTOFOCUSREADYFORCOMMAND | 0X0000 | 0X0000 | 0X0000 | 0X0000 | 0X00 | 0X00 | 0X00 |
| 291 | AUTOFOCUSFORWARD2 | 0X0000 | 0X0000 | 0X0000 | F1 | 0X00 | 0X00 | 0X00 |
| 292 | WAIT FOR OBA AND BRANCH TO AUTOFOCUSREADYFORCOMMAND | 0X0000 | 0X0000 | 0X0000 | 0X0000 | 0X00 | 0X00 | 0X00 |
| 293 | AUTOFOCUSFORWARD4 | 0X0000 | 0X0000 | 0X0000 | F2 | 0X00 | 0X00 | 0X00 |
| 294 | WAIT FOR OBA AND BRANCH TO AUTOFOCUSREADYFORCOMMAND | 0X0000 | 0X0000 | 0X0000 | 0X0000 | 0X00 | 0X00 | 0X00 |
| 295 | AUTOFOCUSFORWARD8 | 0X0000 | 0X0000 | 0X0000 | F3 | 0X00 | 0X00 | 0X00 |
| 296 | WAIT FOR OBA AND BRANCH TO AUTOFOCUSREADYFORCOMMAND | 0X0000 | 0X0000 | 0X0000 | 0X0000 | 0X00 | 0X00 | 0X00 |
| 297 | AUTOFOCUSFORWARD16 | 0X0000 | 0X0000 | 0X0000 | F4 | 0X00 | 0X00 | 0X00 |
| 298 | WAIT FOR OBA AND BRANCH TO AUTOFOCUSREADYFORCOMMAND | 0X0000 | 0X0000 | 0X0000 | 0X0000 | 0X00 | 0X00 | 0X00 |
| 299 | AUTOFOCUSFORWARD32 | 0X0000 | 0X0000 | 0X0000 | F5 | 0X00 | 0X00 | 0X00 |
| 300 | WAIT FOR OBA AND BRANCH TO AUTOFOCUSREADYFORCOMMAND | 0X0000 | 0X0000 | 0X0000 | 0X0000 | 0X00 | 0X00 | 0X00 |
| 301 | AUTOFOCUSFORWARD64 | 0X0000 | 0X0000 | 0X0000 | F6 | 0X00 | 0X00 | 0X00 |
| 302 | WAIT FOR OBA AND BRANCH TO AUTOFOCUSREADYFORCOMMAND | 0X0000 | 0X0000 | 0X0000 | 0X0000 | 0X00 | 0X00 | 0X00 |
| 303 | AUTOFOCUSFORWARD128 | 0X0000 | 0X0000 | 0X0000 | F7 | 0X00 | 0X00 | 0X00 |
| 304 | WAIT FOR OBA AND BRANCH TO AUTOFOCUSREADYFORCOMMAND | 0X0000 | 0X0000 | 0X0000 | 0X0000 | 0X00 | 0X00 | 0X00 |
| 305 | AUTOFOCUSFORWARD256 | 0X0000 | 0X0000 | 0X0000 | F8 | 0X00 | 0X00 | 0X00 |
| 306 | WAIT FOR OBA AND BRANCH TO AUTOFOCUSREADYFORCOMMAND | 0X0000 | 0X0000 | 0X0000 | 0X0000 | 0X00 | 0X00 | 0X00 |
| 307 | AUTOFOCUSFORWARD512 | 0X0000 | 0X0000 | 0X0000 | F9 | 0X00 | 0X00 | 0X00 |
| 308 | WAIT FOR OBA AND BRANCH TO AUTOFOCUSREADYFORCOMMAND | 0X0000 | 0X0000 | 0X0000 | 0X0000 | 0X00 | 0X00 | 0X00 |
| 309 | AUTOFOCUSFORWARD1024 | 0X0000 | 0X0000 | 0X0000 | FA | 0X00 | 0X00 | 0X00 |
| 310 | WAIT FOR OBA AND BRANCH TO AUTOFOCUSREADYFORCOMMAND | 0X0000 | 0X0000 | 0X0000 | 0X0000 | 0X00 | 0X00 | 0X00 |
| 311 | AUTOFOCUSFORWARD2048 | 0X0000 | 0X0000 | 0X0000 | FB | 0X00 | 0X00 | 0X00 |
| 312 | WAIT FOR OBA AND BRANCH TO AUTOFOCUSREADYFORCOMMAND | 0X0000 | 0X0000 | 0X0000 | 0X0000 | 0X00 | 0X00 | 0X00 |
| 313 | AUTOFOCUSCLEANUP: TO WASTE WELL | TW | DB | 0X0000 | 0X0000 | 0x15 | 0x00 | 0X00 |
| 314 | | 0X0000 | 0X0000 | 0X0000 | 0X0000 | 0xFF | 0x00 | 0X00 |
| 315 | | 0X0000 | 0X0000 | 0X0000 | 0X0000 | 0x00 | 0xFF | 0X00 |
| 316 | TEST SHEATH FULL SENSOR | 0X0000 | 0X0000 | 0X0000 | 0X0000 | 0X00 | 0X00 | 0X00 |
| 317 | TURN ON RINSE PUMP AND RINSE PIPETTER | TR | RP | 0X0000 | 0X0000 | 0X00 | 0x25 | 0X00 |

FIG. 8G2

| SMTST | TOSM | TVALUE | TFUNC | SENS | STST | SMSK | END | BRAN | DEST | TRANSLATED PARAMETERS |
|---|---|---|---|---|---|---|---|---|---|---|
| 0X3036 | 0X8D | 0x0000 | 0x00 | 0x0032 | 0X00 | 0x02 | 0x0001 | 0x0010 | 274 | 0X00, 0x02, 0x0001, 0x0010, 274}, |
| 0X3036 | 0x31 | 0X0063 | 0x43 | 0X0000 | 0X00 | 0X00 | 0X0010 | 0X0000 | 0X4258 | 0X00, 0X00, 0X0010, 0X0000, 0X4258}, |
| 0X3030 | 0 | 0X0000 | 0X00 | 0X0000 | 0X00 | 0X00 | 0X0101 | 0X0020 | 270 | 0X00, 0X00, 0X0101, 0X0020, 270}, |
| 0x0000 | 0x87 | 0X0000 | 0X00 | 0X0000 | 0X00 | 0X00 | 0X0101 | 0X0000 | 0X0000 | 0X00, 0X00, 0X0101, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0x8606 | 0X0000 | 0X0000 | 0X00, 0X00, 0x8606, 0X0000, 0X0000}, |
| 0X0000 | 0 | 0X0000 | 0X00 | 0X0000 | 0X00 | 0X00 | 0X0000 | 0X0101 | 163 | 0X00, 0X00, 0X0000, 0X0101, 163}, |
| 0x3130 | 0 | 0X0044 | 0x44 | 0X0000 | 0X00 | 0X00 | 0X001F | 0X0000 | 0X0000 | 0X00, 0X00, 0X001F, 0X0000, 0X0000}, |
| 0x0000 | 0 | 0X0045 | 0x42 | 0X0000 | 0X00 | 0X00 | 0X001F | 0x0000 | 0x0000 | 0X00, 0X00, 0X001F, 0X0000, 0X0000}, |
| 0X0000 | 0x8B | 0X0000 | 0X00 | 0X0000 | 0X00 | 0X00 | 0x0101 | 0X0000 | 0X0000 | 0X00, 0X00, 0x0101, 0X0000, 0X0000}, |
| 0X0000 | 0 | 0X0000 | 0X00 | 0X0000 | 0X00 | 0X00 | 0X0000 | 0x0101 | 193 | 0X00, 0X00, 0X0000, 0x0101, 193}, |
| 0X0000 | 0 | 0x2000 | 0x04 | 0X0000 | 0X00 | 0X00 | 0x0040 | 0X0000 | 0X0000 | 0X00, 0X00, 0x0040, 0X0000, 0X0000}, |
| 0X0000 | 0 | 0X0000 | 0X00 | 0X0000 | 0X00 | 0X00 | 0x0040 | 0x0040 | 163 | 0X00, 0X00, 0x0040, 0x0040, 163}, |
| 0X0000 | 0 | 0x2000 | 0x04 | 0X0000 | 0X00 | 0X00 | 0x0040 | 0X0000 | 0X0000 | 0X00, 0X00, 0x0040, 0X0000, 0X0000}, |
| 0X0000 | 0 | 0X0000 | 0X00 | 0X0000 | 0X00 | 0X00 | 0x0040 | 0x0040 | 163 | 0X00, 0X00, 0x0040, 0x0040, 163}, |
| 0X0000 | 0 | 0x2000 | 0x04 | 0X0000 | 0X00 | 0X00 | 0x0040 | 0X0000 | 0X0000 | 0X00, 0X00, 0x0040, 0X0000, 0X0000}, |
| 0X0000 | 0 | 0X0000 | 0X00 | 0X0000 | 0X00 | 0X00 | 0x0040 | 0x0040 | 163 | 0X00, 0X00, 0x0040, 0x0040, 163}, |
| 0X0000 | 0 | 0x2000 | 0x04 | 0X0000 | 0X00 | 0X00 | 0x0040 | 0X0000 | 0X0000 | 0X00, 0X00, 0x0040, 0X0000, 0X0000}, |
| 0X0000 | 0 | 0X0000 | 0X00 | 0X0000 | 0X00 | 0X00 | 0x0040 | 0x0040 | 163 | 0X00, 0X00, 0x0040, 0x0040, 163}, |
| 0X0000 | 0 | 0x2000 | 0x04 | 0X0000 | 0X00 | 0X00 | 0x0040 | 0X0000 | 0X0000 | 0X00, 0X00, 0x0040, 0X0000, 0X0000}, |
| 0X0000 | 0 | 0X0000 | 0X00 | 0X0000 | 0X00 | 0X00 | 0x0040 | 0x0040 | 163 | 0X00, 0X00, 0x0040, 0x0040, 163}, |
| 0X0000 | 0 | 0x2000 | 0x04 | 0X0000 | 0X00 | 0X00 | 0x0040 | 0X0000 | 0X0000 | 0X00, 0X00, 0x0040, 0X0000, 0X0000}, |
| 0X0000 | 0 | 0X0000 | 0X00 | 0X0000 | 0X00 | 0X00 | 0x0040 | 0x0040 | 163 | 0X00, 0X00, 0x0040, 0x0040, 163}, |
| 0X0000 | 0 | 0x2000 | 0x04 | 0X0000 | 0X00 | 0X00 | 0x0040 | 0X0000 | 0X0000 | 0X00, 0X00, 0x0040, 0X0000, 0X0000}, |
| 0X0000 | 0 | 0X0000 | 0X00 | 0X0000 | 0X00 | 0X00 | 0x0040 | 0x0040 | 163 | 0X00, 0X00, 0x0040, 0x0040, 163}, |
| 0X0000 | 0 | 0x2000 | 0x04 | 0X0000 | 0X00 | 0X00 | 0x0040 | 0X0000 | 0X0000 | 0X00, 0X00, 0x0040, 0X0000, 0X0000}, |
| 0X0000 | 0 | 0X0000 | 0X00 | 0X0000 | 0X00 | 0X00 | 0x0040 | 0x0040 | 163 | 0X00, 0X00, 0x0040, 0x0040, 163}, |
| 0X0000 | 0 | 0x2000 | 0x04 | 0X0000 | 0X00 | 0X00 | 0x0040 | 0X0000 | 0X0000 | 0X00, 0X00, 0x0040, 0X0000, 0X0000}, |
| 0X0000 | 0 | 0X0000 | 0X00 | 0X0000 | 0X00 | 0X00 | 0x0040 | 0x0040 | 163 | 0X00, 0X00, 0x0040, 0x0040, 163}, |
| 0X0000 | 0 | 0x2000 | 0x04 | 0X0000 | 0X00 | 0X00 | 0x0040 | 0X0000 | 0X0000 | 0X00, 0X00, 0x0040, 0X0000, 0X0000}, |
| 0X0000 | 0 | 0X0000 | 0X00 | 0X0000 | 0X00 | 0X00 | 0x0040 | 0x0040 | 163 | 0X00, 0X00, 0x0040, 0x0040, 163}, |
| 0X0000 | 0 | 0x2000 | 0x04 | 0X0000 | 0X00 | 0X00 | 0x0040 | 0X0000 | 0X0000 | 0X00, 0X00, 0x0040, 0X0000, 0X0000}, |
| 0X0000 | 0 | 0X0000 | 0X00 | 0X0000 | 0X00 | 0X00 | 0x0040 | 0x0040 | 163 | 0X00, 0X00, 0x0040, 0x0040, 163}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0x0033 | 0x01 | 0x01 | 0x0101 | 0x0001 | 318 | 0x01, 0x01, 0x0101, 0x0001, 318}, |
| 0X0000 | 0 | 0X0000 | 0X00 | 0X0000 | 0X00 | 0X00 | 0x0000 | 0x001F | 319 | 0X00, 0X00, 0x0000, 0x001F, 319}, |

FIG. 8H1

| STATE INDEX | STATE DESCRIPTION | SPACMD | FBACMD | STMCMD | OBACMD | SPASTAT | FBASTAT | STMSTAT | OBASTAT |
|---|---|---|---|---|---|---|---|---|---|
| 317 | TURN ON RINSE PUMP AND RINSE PIPETTER | TR | RP | 0X0000 | 0X0000 | 0X00 | 0x25 | 0X00 | 0X00 |
| 318 | TURN ON RINSE PUMP AND RINSE PIPETTER | TO | RP | 0X0000 | 0X0000 | 0X00 | 0x25 | 0X00 | 0X00 |
| 319 | | 0X0000 | 0X0000 | 0X0000 | 0X0000 | 0xFF | 0x00 | 0X00 | 0X00 |
| 320 | | 0X0000 | 0X0000 | 0X0000 | 0X0000 | 0x00 | 0xFF | 0X00 | 0X00 |
| 321 | CLEAR PIPETTER/HOME CP AND SP/MOVE TO NEXT TUBE | CP | HC | MN | 0X0000 | 0X16 | 0X00 | 0X00 | 0X00 |
| 322 | | 0X0000 | 0X0000 | 0X0000 | 0X0000 | 0XFF | 0x00 | 0X00 | 0X00 |
| 323 | | 0X0000 | 0X0000 | 0X0000 | 0X0000 | 0x00 | 0xFF | 0X00 | 0X00 |
| 324 | | 0X0000 | 0X0000 | 0X0000 | 0X0000 | 0x00 | 0x00 | 0XFF | 0X00 |
| 325 | BRANCH TO "16" (GO RESUME) | 0X0000 | 0X0000 | 0X0000 | 0X0000 | 0X00 | 0X00 | 0X00 | 0X00 |
| 326 | MOVETONEXTCONTROLTUBE_AF: MOVE TO NEXT CONTROL TUBE POSITION (AF) | 0X0000 | 0X0000 | MN | 0X0000 | 0X00 | 0X00 | 0X32 | 0X00 |
| 327 | BRANCH TO "16" (GO RESUME) | 0X0000 | 0X0000 | 0X0000 | 0X0000 | 0X00 | 0X00 | 0X00 | 0X00 |
| 328 | VALIDATEFOCUSPOSITION: WAIT FOR OBA IDLE | 0X0000 | 0X0000 | 0X0000 | 0x0000 | 0X00 | 0X00 | 0X00 | 0xFF |
| 329 | VALIDATE CURRENT FOCUS POSITION (MUST BE "IN FIRST | 0X0000 | 0X0000 | 0X0000 | VP | 0X00 | 0X00 | 0X00 | 0x00 |
| 330 | AF_VALIDATE1: IF 31 ("GOOD") FROM OBA GOTO AF_ISVALID | 0X0000 | 0X0000 | 0X0000 | 0X0000 | 0X00 | 0X00 | 0x00 | 0x31 |
| 331 | IF 30 ("BAD") FROM OBA GOTO AF_ISNOTVALID | 0X0000 | 0X0000 | 0X0000 | 0X0000 | 0X00 | 0X00 | 0x00 | 0x30 |
| 332 | LOOP BACK TO AF_VALIDATE1 | 0X0000 | 0X0000 | 0X0000 | 0X0000 | 0X00 | 0X00 | 0X00 | 0X00 |
| 333 | AF_ISVALID: SEND EFOCUSPOSITIONISVALID (0X29) TO HOST AND GOTO AUTOFOCUSREADYFORCOMMAND | 0X0000 | 0X0000 | 0X0000 | 0X0000 | 0X00 | 0X00 | 0X00 | 0X00 |
| 334 | AF_ISNOTVALID: SEND EFOCUSPOSITIONISNOTVALID (0X28) TO HOST AND GOTO AUTOFOCUSREADYFORCOMMAND | 0X0000 | 0X0000 | 0X0000 | 0X0000 | 0X00 | 0X00 | 0X00 | 0X00 |
| 335 | END "17" (AUTOFOCUS CONTROL) | 0X0000 | 0X0000 | 0X0000 | 0X0000 | 0X00 | 0X00 | 0X00 | 0X00 |
| 336 | START NEW IDLE | 0X0000 | 0X0000 | 0X0000 | 0X0000 | 0X00 | 0X00 | 0X00 | 0xFF |
| 337 | SEND SYNCH COMMAND TO HOST | 0X0000 | 0X0000 | 0X0000 | 0X0000 | 0X00 | 0X00 | 0x00 | 0X00 |
| 338 | WAIT FOR SM COMMAND | 0X0000 | 0X0000 | 0X0000 | 0X0000 | 0X00 | 0X00 | 0x00 | 0X00 |
| 339 | TELL STM TO LOOK FOR RACKS | 0X0000 | 0X0000 | WR | 0X0000 | 0X00 | 0X00 | 0X00 | 0X00 |
| 340 | WAIT FOR BUTTON OR RACK | 0X0000 | 0X0000 | 0X0000 | 0X0000 | 0X00 | 0X00 | 0X52 | 0X00 |
| 341 | SEND SYNCH COMMAND TO HOST | 0X0000 | 0X0000 | 0X0000 | 0X0000 | 0X00 | 0X00 | 0x00 | 0X00 |
| 342 | WAIT FOR SM COMMAND | 0X0000 | 0X0000 | 0X0000 | 0X0000 | 0X00 | 0X00 | 0X00 | 0X00 |
| 343 | BRANCH TO SHUTDOWN IF STANDBY PERIOD EXCEEDED | 0X0000 | 0X0000 | 0X0000 | 0X0000 | 0X00 | 0X00 | 0X00 | 0X00 |
| 344 | UNCONDITIONALLY BRANCH TO END IDLE | 0X0000 | 0X0000 | 0X0000 | 0X0000 | 0X00 | 0X00 | 0X00 | 0X00 |
| 345 | BRANCH TO WAKEUP LONG IF LONG STANDBY PERIOD EXCEEDED | 0X0000 | 0X0000 | 0X0000 | 0X0000 | 0X00 | 0X00 | 0X00 | 0X00 |
| 346 | BRANCH TO WAKEUP MEDIUM IF INTERMEDIATE STANDBY PERIOD | 0X0000 | 0X0000 | 0X0000 | 0X0000 | 0X00 | 0X00 | 0X00 | 0X00 |
| 347 | BRANCH UNCONDITIONALLY TO WAKEUP SHORT | 0X0000 | 0X0000 | 0X0000 | 0X0000 | 0X00 | 0X00 | 0X00 | 0X00 |
| 348 | | 0X0000 | 0X0000 | 0X0000 | 0X0000 | 0X00 | 0X00 | 0X00 | 0X00 |
| 349 | TIMEOUT -- GO TO REAL IDLE | 0X0000 | 0X0000 | 0X0000 | 0X0000 | 0X00 | 0X00 | 0X00 | 0X00 |
| 350 | START PI TO TEST TUBE;ALSO START WA(WASH) | TT | 0X0000 | 0X0000 | 0X0000 | 0x11 | 0x00 | 0X00 | 0X00 |
| 351 | | 0X0000 | 0X0000 | 0X0000 | 0X0000 | 0xFF | 0x00 | 0X00 | 0X00 |
| 352 | START SHEATH FOR BACKGROUND CAPTURE | SB | 0X0000 | 0X0000 | 0X0000 | 0x31 | 0X00 | 0X00 | 0X00 |
| 353 | WAIT FOR SB COMPLETE | 0X0000 | 0X0000 | 0X0000 | 0X0000 | 0xFF | 0x00 | 0X00 | 0X00 |
| 354 | TIMER DELAY | 0X0000 | 0X0000 | 0X0000 | 0X0000 | 0x00 | 0x00 | 0X00 | 0x00 |
| 355 | TURN OFF EP PUMP ON SPA | EB | 0X0000 | 0X0000 | 0X0000 | 0x34 | 0x00 | 0X00 | 0X00 |
| 356 | WAIT FOR EB COMPLETE | 0X0000 | 0X0000 | 0X0000 | 0X0000 | 0xFF | 0x00 | 0X00 | 0X00 |
| 357 | MOVE PIPETTE DOWN TO ASPIRATE POSITION IN TEST TUBE | TD | 0X0000 | 0X0000 | 0X0000 | 0x13 | 0x00 | 0X00 | 0X00 |
| 358 | WAIT FOR TD COMPLETE | 0X0000 | 0X0000 | 0X0000 | 0X0000 | 0xFF | 0x00 | 0X00 | 0X00 |
| 359 | START ASPIRATION FOR SAMPLE TRANSFER | AS | RC | 0X0000 | 0X0000 | 0x17 | 0x00 | 0X00 | 0X00 |
| 360 | WAIT FOR AS AND RC COMPLETE | 0X0000 | 0X0000 | 0X0000 | 0X0000 | 0xFF | 0xFF | 0X00 | 0X00 |
| 361 | TIMER DELAY | 0X0000 | 0X0000 | 0X0000 | 0X0000 | 0x00 | 0X00 | 0X00 | 0X00 |
| 362 | TURN OFF EP PUMP ON SPA, SP PUMP ON FBA | EB | EB | 0X0000 | 0X0000 | 0x34 | 0x00 | 0X00 | 0X00 |
| 363 | WAIT FOR EB'S COMPLETE (SPA AND FBA) | 0X0000 | 0X0000 | 0X0000 | 0X0000 | 0xFF | 0xFF | 0X00 | 0X00 |
| 364 | TO WASTE WELL | TW | DB | 0X0000 | 0X0000 | 0x15 | 0x00 | 0X00 | 0X00 |
| 365 | | 0X0000 | 0X0000 | 0X0000 | 0X0000 | 0xFF | 0x00 | 0X00 | 0X00 |
| 366 | | 0X0000 | 0X0000 | 0X0000 | 0X0000 | 0x00 | 0xFF | 0X00 | 0X00 |
| 367 | DRAIN FLOWCELL | DF | 0x0000 | 0X0000 | 0X0000 | 0X26 | 0x00 | 0X00 | 0X00 |
| 368 | | 0X0000 | 0X0000 | 0X0000 | 0X0000 | 0xFF | 0x00 | 0X00 | 0X00 |
| 369 | PRIME SHEATH SUPPLY LINE | PS | 0X0000 | 0X0000 | 0X0000 | 0X20 | 0x00 | 0X00 | 0X00 |
| 370 | | 0X0000 | 0X0000 | 0X0000 | 0X0000 | 0xFF | 0x00 | 0X00 | 0X00 |
| 371 | PRIME ALL PUMPS | PP | PC | 0X0000 | 0X0000 | 0X21 | 0x00 | 0X00 | 0X00 |
| 372 | | 0X0000 | 0X0000 | 0X0000 | 0X0000 | 0xFF | 0x00 | 0X00 | 0X00 |
| 373 | | 0X0000 | 0X0000 | 0X0000 | 0X0000 | 0x00 | 0xFF | 0X00 | 0X00 |
| 374 | PRIME INNER LINES #1 | TR | PI | 0X0000 | 0X0000 | 0x00 | 0x24 | 0X00 | 0X00 |
| 375 | | 0X0000 | 0X0000 | 0X0000 | 0X0000 | 0x00 | 0xFF | 0X00 | 0X00 |

FIG. 8H2

| SMTST | TOSM | TVALUE | TFUNC | SENS | STST | SMSK | END | BRAN | DEST | TRANSLATED PARAMETERS |
|---|---|---|---|---|---|---|---|---|---|---|
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x36 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X0000 | 0X0101 | 0x3136 | 0X00, 0X00, 0X0000, 0X0101, 0x3136}, |
| 0X0000 | 0x36 | 0X0049 | 0x04 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X0000 | 0X0101 | 0x3136 | 0X00, 0X00, 0X0000, 0X0101, 0x3136}, |
| 0X0000 | 0 | 0x2000 | 0x04 | 0X0000 | 0X00 | 0X00 | 0x0040 | 0X0000 | 0X0000 | 0X00, 0X00, 0x0040, 0X0000, 0X0000}, |
| 0X0000 | 0 | 0x2000 | 0x04 | 0X0000 | 0X00 | 0X00 | 0x0101 | 0X0000 | 0X0000 | 0X00, 0X00, 0x0101, 0X0000, 0X0000}, |
| 0X0000 | 0x00 | 0X0000 | 0X00 | 0X0000 | 0X00 | 0X00 | 0x4040 | 0x0040 | 333 | 0X00, 0X00, 0x4040, 0x0040, 333}, |
| 0X0000 | 0x00 | 0X0000 | 0X00 | 0X0000 | 0X00 | 0X00 | 0x4040 | 0x0040 | 334 | 0X00, 0X00, 0x4040, 0x0040, 334}, |
| 0X0000 | 0 | 0X0000 | 0X00 | 0X0000 | 0X00 | 0X00 | 0X001F | 0X0101 | 330 | 0X00, 0X00, 0X001F, 0X0101, 330}, |
| 0X0000 | 0x29 | 0x0020 | 0x03 | 0X0000 | 0X00 | 0X00 | 0X0000 | 0x0000 | 163 | 0X00, 0X00, 0X0000, 0x0000, 163}, |
| 0X0000 | 0x28 | 0x0020 | 0x03 | 0X0000 | 0X00 | 0X00 | 0X0000 | 0x0000 | 163 | 0X00, 0X00, 0X0000, 0x0000, 163}, |
| 0X0000 | 0 | 0x00A0 | 0x04 | 0X0000 | 0X00 | 0X00 | 0x0000 | 0X0000 | 0X0000 | 0X00, 0X00, 0x0000, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x2c | 0X0000 | 0X00 | 0X0000 | 0X00 | 0X00 | 0X0101 | 0X0000 | 0X0000 | 0X00, 0X00, 0X0101, 0X0000, 0X0000}, |
| 0X0000 | 0 | 0X004A | 0x42 | 0x0000 | 0X00 | 0x00 | 0X0000 | 0x0080 | 0x0000 | 0x00, 0x00, 0X0000, 0x0080, 0x0000}, |
| 0X0000 | 0 | 0X004B | 0x44 | 0X0000 | 0X00 | 0X00 | 0X0101 | 0X0000 | 0X0000 | 0X00, 0X00, 0X0101, 0X0000, 0X0000}, |
| 0X0000 | 0 | 0X004C | 0X42 | 0X0032 | 0X00 | 0X01 | 0X0000 | 0x0009 | 345 | 0X00, 0X01, 0X0000, 0x0009, 345}, |
| 0X0000 | 0x2c | 0X0000 | 0X00 | 0X0000 | 0X00 | 0X00 | 0X0101 | 0X0000 | 0X0000 | 0X00, 0X00, 0X0101, 0X0000, 0X0000}, |
| 0X0000 | 0 | 0X004D | 0x42 | 0x0000 | 0X00 | 0x00 | 0X0000 | 0x0080 | 0X0000 | 0x00, 0x00, 0X0000, 0x0080, 0X0000}, |
| 0X0000 | 0 | 0X0000 | 0X00 | 0x9000 | 0x05 | 0x40 | 0x0101 | 0x0001 | 0X5344 | 0x05, 0x40, 0x0101, 0X0001, 0X5344}, |
| 0X0000 | 0 | 0X0000 | 0X00 | 0X0000 | 0X00 | 0X00 | 0X0000 | 0X0101 | 349 | 0X00, 0X00, 0X0000, 0X0101, 349}, |
| 0X0000 | 0 | 0X0000 | 0X00 | 0x9000 | 0x05 | 0x41 | 0X0101 | 0x0001 | 0X574C | 0x05, 0x41, 0X0101, 0x0001, 0X574C}, |
| 0X0000 | 0 | 0X0000 | 0X00 | 0x9000 | 0x05 | 0x42 | 0X0101 | 0x0001 | 0X574D | 0x05, 0x42, 0X0101, 0x0001, 0X574D}, |
| 0X0000 | 0 | 0X0000 | 0X00 | 0X0000 | 0X00 | 0X00 | 0X0000 | 0X0101 | 0X5753 | 0X00, 0X00, 0X0000, 0X0101, 0X5753}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x33 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X004E | 0x42 | 0x0000 | 0x00 | 0x00 | 0X0010 | 0x0000 | 0x4258 | 0x00, 0x00, 0X0010, 0x0000, 0x4258}, |
| 0X0000 | 0x32 | 0X0000 | 0X00 | 0X0000 | 0X00 | 0X00 | 0x001F | 0X0000 | 0X0000 | 0X00, 0X00, 0x001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0x8606 | 0X0000 | 0X0000 | 0X00, 0X00, 0x8606, 0X0000, 0X0000}, |
| 0X0000 | 0x32 | 0x0065 | 0x42 | 0X0000 | 0X00 | 0X00 | 0X0010 | 0X0000 | 0X0000 | 0X00, 0X00, 0X0010, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0x8606 | 0X0000 | 0X0000 | 0X00, 0X00, 0x8606, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |

FIG. 8I1

| STATE INDEX | STATE DESCRIPTION | SPACMD | FBACMD | STMCMD | OBACMD | SPASTAT | FBASTAT | STMSTAT | OBASTAT |
|---|---|---|---|---|---|---|---|---|---|
| 376 | | 0X0000 | 0X0000 | 0X0000 | 0X0000 | 0xFF | 0x00 | 0X00 | 0X00 |
| 377 | PRIME INNER LINES #2 | PL | 0X0000 | 0X0000 | 0X0000 | 0X22 | 0x00 | 0X00 | 0X00 |
| 378 | | 0X0000 | 0X0000 | 0X0000 | 0X0000 | 0xFF | 0x00 | 0X00 | 0X00 |
| 379 | PRIME ASPIRATION LINE | TR | PA | 0X0000 | 0X0000 | 0X00 | 0x26 | 0X00 | 0X00 |
| 380 | | 0X0000 | 0X0000 | 0X0000 | 0X0000 | 0x00 | 0xFF | 0X00 | 0X00 |
| 381 | | 0X0000 | 0X0000 | 0X0000 | 0X0000 | 0xFF | 0x00 | 0X00 | 0X00 |
| 382 | DEBUBBLE | 0X0000 | DE | 0X0000 | 0X0000 | 0X00 | 0x30 | 0X00 | 0X00 |
| 383 | | 0X0000 | 0X0000 | 0X0000 | 0X0000 | 0x00 | 0xFF | 0X00 | 0X00 |
| 384 | TURN ON RINSE PUMP AND RINSE PIPETTER | TR | RP | 0X0000 | 0X0000 | 0X00 | 0x25 | 0X00 | 0X00 |
| 385 | | 0X0000 | 0X0000 | 0X0000 | 0X0000 | 0xFF | 0x00 | 0X00 | 0X00 |
| 386 | | 0X0000 | 0X0000 | 0X0000 | 0X0000 | 0x00 | 0xFF | 0X00 | 0X00 |
| 387 | CLEAR PIPETTER | CP | HC | 0X0000 | 0X0000 | 0X16 | 0x00 | 0X00 | 0X00 |
| 388 | | 0X0000 | 0X0000 | 0X0000 | 0X0000 | 0xFF | 0x00 | 0X00 | 0X00 |
| 389 | | 0X0000 | 0X0000 | 0X0000 | 0X0000 | 0x00 | 0xFF | 0X00 | 0X00 |
| 390 | MOVE TO NEXT TUBE POSITION | 0X0000 | 0X0000 | MN | 0X0000 | 0X00 | 0X00 | 0X32 | 0X00 |
| 391 | BRANCH TO '16' (GO RESUME) | 0X0000 | 0X0000 | 0X0000 | 0X0000 | 0X00 | 0X00 | 0X00 | 0X00 |
| 392 | END WA (WASH) | 0X0000 | 0X0000 | 0X0000 | 0X0000 | 0X00 | 0X00 | 0X00 | 0X00 |
| 393 | START ZZ (SLEEP) | 0X0000 | 0X0000 | 0X0000 | 0X0000 | 0x00 | 0x00 | 0X00 | 0X00 |
| 394 | END ZZ (SLEEP) | 0X0000 | 0X0000 | 0X0000 | 0X0000 | 0x00 | 0x00 | 0X00 | 0X00 |
| 395 | START SS: RESET HLCS | RE | RE | RE | RE | 0XFF | 0XFF | 0XFF | 0XFF |
| 396 | MAKE SURE OUTPUT IS CLEAR (STM:IC RETURNS 'T' OR 'F') | 0X0000 | 0X0000 | IC | 0X0000 | 0X00 | 0X00 | 0X00 | 0X00 |
| 397 | GOT 'T'? IF SO, BRANCH TO SETFRONTPANELLIGHTSSS1 | 0X0000 | 0X0000 | 0X0000 | 0X0000 | 0X00 | 0X00 | 0x54 | 0X00 |
| 398 | GOT 'F'? IF SO, BRANCH TO END OF GO SEQUENCE | 0X0000 | 0X0000 | 0X0000 | 0X0000 | 0X00 | 0X00 | 0x46 | 0X00 |
| 399 | LOOP BACK TO LOOKINGFORT1 | 0X0000 | 0X0000 | 0X0000 | 0X0000 | 0X00 | 0X00 | 0X00 | 0X00 |
| 400 | SET FRONT PANEL LIGHTS (BUTTON GREEN, LED BLUE) | 0X0000 | 0X0000 | 0X0000 | 0X0000 | 0X00 | 0X00 | 0XFF | 0X00 |
| 401 | TELL STM TO FIND RACK | PH | 0X0000 | M1 | 0X0000 | 0X00 | 0X00 | 0X00 | 0X00 |
| 402 | IF 31 FROM STM GOTO WAITUNTILSTMATIDLE_SS | 0X0000 | 0X0000 | 0X0000 | 0X0000 | 0X00 | 0X00 | 0X31 | 0X00 |
| 403 | NO RACK -- ENDSSBRANCHTARGET | 0X0000 | 0X0000 | 0X0000 | 0X0000 | 0X00 | 0X00 | 0X39 | 0X00 |
| 404 | LOOP BACK | 0X0000 | 0X0000 | 0X0000 | 0X0000 | 0X00 | 0X00 | 0X00 | 0X00 |
| 405 | WAITUNTILSTMATIDLE_SS (WAIT FOR SPA IDLE AS WELL) | 0X0000 | 0X0000 | 0X0000 | 0X0000 | 0xFF | 0X00 | 0XFF | 0X00 |
| 406 | MOVE TO NEXT TUBE POSITION (FIRST TUBE ASPIRATE POSITION) | 0X0000 | 0X0000 | MN | 0X0000 | 0X00 | 0X00 | 0X32 | 0X00 |
| 407 | TO TEST TUBE | TT | 0X0000 | 0X0000 | 0X0000 | 0x11 | 0x00 | 0X00 | 0X00 |
| 408 | | 0X0000 | 0X0000 | 0X0000 | 0X0000 | 0xFF | 0x00 | 0X00 | 0X00 |
| 409 | START SHEATH FOR BACKGROUND CAPTURE | SB | 0X0000 | 0X0000 | 0X0000 | 0X31 | 0X00 | 0X00 | 0X00 |
| 410 | WAIT FOR SB COMPLETE | 0X0000 | 0X0000 | 0X0000 | 0X0000 | 0xFF | 0x00 | 0X00 | 0X00 |
| 411 | TIMER DELAY | 0X0000 | 0X0000 | 0X0000 | 0X0000 | 0x00 | 0x00 | 0x00 | 0x00 |
| 412 | TURN OFF EP PUMP ON SPA | EB | 0X0000 | 0X0000 | 0X0000 | 0x34 | 0x00 | 0X00 | 0X00 |
| 413 | WAIT FOR EB COMPLETE | 0X0000 | 0X0000 | 0X0000 | 0X0000 | 0xFF | 0x00 | 0X00 | 0X00 |
| 414 | MOVE PIPETTE DOWN TO ASPIRATE POSITION IN TEST TUBE | TD | 0X0000 | 0X0000 | 0X0000 | 0X13 | 0x00 | 0X00 | 0X00 |
| 415 | WAIT FOR TD COMPLETE | 0X0000 | 0X0000 | 0X0000 | 0X0000 | 0xFF | 0x00 | 0X00 | 0X00 |
| 416 | START ASPIRATION FOR SAMPLE TRANSFER | AS | RC | 0X0000 | 0X0000 | 0x17 | 0x00 | 0X00 | 0X00 |
| 417 | WAIT FOR AS AND RC COMPLETE | 0X0000 | 0X0000 | 0X0000 | 0X0000 | 0xFF | 0xFF | 0X00 | 0X00 |
| 418 | TIMER DELAY | 0X0000 | 0X0000 | 0X0000 | 0X0000 | 0x00 | 0x00 | 0X00 | 0X00 |
| 419 | TURN OFF EP PUMP ON SPA, SP PUMP ON FBA | EB | EB | 0X0000 | 0X0000 | 0x34 | 0x00 | 0X00 | 0X00 |
| 420 | WAIT FOR EB'S COMPLETE (SPA AND FBA) | 0X0000 | 0X0000 | 0X0000 | 0X0000 | 0xFF | 0xFF | 0X00 | 0X00 |
| 421 | TO WASTE WELL | TW | DB | 0X0000 | 0X0000 | 0x15 | 0x00 | 0X00 | 0X00 |
| 422 | | 0X0000 | 0X0000 | 0X0000 | 0X0000 | 0xFF | 0x00 | 0X00 | 0X00 |
| 423 | | 0X0000 | 0X0000 | 0X0000 | 0X0000 | 0x00 | 0xFF | 0X00 | 0X00 |
| 424 | TURN ON RINSE PUMP AND RINSE PIPETTER | TR | RP | 0X0000 | 0X0000 | 0X00 | 0x25 | 0X00 | 0X00 |
| 425 | | 0X0000 | 0X0000 | 0X0000 | 0X0000 | 0xFF | 0x00 | 0X00 | 0X00 |
| 426 | | 0X0000 | 0X0000 | 0X0000 | 0X0000 | 0x00 | 0xFF | 0X00 | 0X00 |
| 427 | CLEAR PIPETTER/HOME CP AND SP/MOVE TO NEXT TUBE | CP | HC | MN | 0X0000 | 0X16 | 0X00 | 0X00 | 0X00 |
| 428 | | 0X0000 | 0X0000 | 0X0000 | 0X0000 | 0XFF | 0x00 | 0X00 | 0X00 |
| 429 | | 0X0000 | 0X0000 | 0X0000 | 0X0000 | 0X00 | 0xFF | 0X00 | 0X00 |
| 430 | | 0X0000 | 0X0000 | 0X0000 | 0X0000 | 0x00 | 0x00 | 0XFF | 0X00 |
| 431 | MAKE SURE SPA AND STM IDLE | 0x0000 | 0X0000 | 0X0000 | 0X0000 | 0xFF | 0X00 | 0XFF | 0X00 |
| 432 | SEND CR TO STM- HOME PIPETTER | PH | 0X0000 | CR | 0X0000 | 0X00 | 0X00 | 0X33 | 0X00 |
| 433 | HOME STM CARRIERS | 0X0000 | 0X0000 | 0x0000 | 0X0000 | 0XFF | 0X00 | 0XFF | 0X00 |
| 434 | END OF SS SEQUENCE | 0X0000 | 0X0000 | 0X0000 | 0X0000 | 0X00 | 0X00 | 0X00 | 0X00 |
| 435 | SW WAKEUP FROM SHORT STANDBY PERIOD - TURN STROBE ON | 0X0000 | 0X0000 | 0X0000 | 0X0000 | 0X00 | 0X00 | 0X00 | 0X00 |

FIG. 8I2

| SMTST | TOSM | TVALUE | TFUNC | SENS | STST | SMSK | END | BRAN | DEST | TRANSLATED PARAMETERS |
|---|---|---|---|---|---|---|---|---|---|---|
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0x36 | 0X0051 | 0x44 | 0X0000 | 0X00 | 0X00 | 0X001F | 0X0000 | 0X0000 | 0X00, 0X00, 0X001F, 0X0000, 0X0000 |
| 0X0000 | 0 | 0X0000 | 0X00 | 0X0000 | 0X00 | 0X00 | 0X0000 | 0X0101 | 0x3136 | 0X00, 0X00, 0X0000, 0X0101, 0x3136 |
| 0X0000 | 0 | 0X0000 | 0X00 | 0X0000 | 0X00 | 0X00 | 0X0000 | 0x0000 | 0x0000 | 0X00, 0X00, 0X0000, 0X0000, 0X0000 |
| 0X0000 | 0xFF | 0X0000 | 0X00 | 0X0000 | 0X00 | 0X00 | 0x0000 | 0x0080 | 0X0000 | 0X00, 0X00, 0x0000, 0x0080, 0X0000 |
| 0X0000 | 0xFF | 0X0000 | 0X00 | 0X0000 | 0X00 | 0X00 | 0x0000 | 0X0000 | 0X0000 | 0X00, 0X00, 0x0000, 0X0000, 0X0000 |
| 0X0000 | 0 | 0X0052 | 0x44 | 0X0000 | 0X00 | 0X00 | 0XCA4A | 0X0000 | 0X0000 | 0X00, 0X00, 0XCA4A, 0X0000, 0X0000 |
| 0X0000 | 0 | 0X0000 | 0X00 | 0X0000 | 0X00 | 0X00 | 0x0101 | 0X0000 | 0X0000 | 0X00, 0X00, 0x0101, 0X0000, 0X0000 |
| 0X0000 | 0 | 0X0000 | 0X00 | 0X0000 | 0X00 | 0X00 | 0x0101 | 0x0008 | 400 | 0X00, 0X00, 0x0101, 0x0008, 400 |
| 0X0000 | 0 | 0X0000 | 0X00 | 0X0000 | 0X00 | 0X00 | 0x0101 | 0x0008 | 434 | 0X00, 0X00, 0x0101, 0x0008, 434 |
| 0X0000 | 0 | 0X0000 | 0X00 | 0x0000 | 0x00 | 0X00 | 0x0000 | 0x0101 | 397 | 0x00, 0X00, 0x0000, 0x0101, 397 |
| 0X0000 | 0 | 0X0000 | 0X00 | 0X6000 | 0X09 | 0X00 | 0X005F | 0X0000 | 0X0000 | 0X09, 0X00, 0X005F, 0X0000, 0X0000 |
| 0X0000 | 0 | 0X0000 | 0X00 | 0X0000 | 0X00 | 0X00 | 0X0101 | 0X0000 | 0X0000 | 0X00, 0X00, 0x0101, 0X0000, 0X0000 |
| 0X0000 | 0 | 0X0000 | 0X00 | 0X0000 | 0X00 | 0X00 | 0X0101 | 0X0008 | 405 | 0X00, 0X00, 0x0101, 0x0008, 405 |
| 0X0000 | 0 | 0X0000 | 0X00 | 0X0000 | 0X00 | 0X00 | 0X0101 | 0X0008 | 434 | 0X00, 0X00, 0x0101, 0x0008, 434 |
| 0X0000 | 0 | 0X0000 | 0X00 | 0X0000 | 0X00 | 0X00 | 0X001F | 0X0101 | 402 | 0X00, 0X00, 0X001F, 0X0101, 402 |
| 0X0000 | 0 | 0X0053 | 0x44 | 0X0000 | 0X00 | 0X00 | 0x8A0A | 0X0000 | 0X0000 | 0X00, 0X00, 0x8A0A, 0X0000, 0X0000 |
| 0X0000 | 0x36 | 0X0054 | 0x44 | 0X0000 | 0X00 | 0X00 | 0X001F | 0X0000 | 0X0000 | 0X00, 0X00, 0X001F, 0X0000, 0X0000 |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0 | 0X0000 | 0X00 | 0X0000 | 0X00 | 0X00 | 0x001F | 0X0000 | 0X0000 | 0X00, 0X00, 0x001F, 0X0000, 0X0000 |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0 | 0x0055 | 0x42 | 0X0000 | 0x00 | 0x00 | 0x0000 | 0x0000 | 0X0000 | 0x00, 0x00, 0x0000, 0x0000, 0X0000 |
| 0X0000 | 0 | 0X0000 | 0X00 | 0X0000 | 0X00 | 0X00 | 0x001F | 0X0000 | 0X0000 | 0X00, 0X00, 0x001F, 0X0000, 0X0000 |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0 | 0X0000 | 0X00 | 0X0000 | 0X00 | 0X00 | 0x8606 | 0X0000 | 0X0000 | 0X00, 0X00, 0x8606, 0X0000, 0X0000 |
| 0X0000 | 0 | 0X0056 | 0x42 | 0X0000 | 0X00 | 0X00 | 0X0010 | 0X0000 | 0X0000 | 0X00, 0X00, 0X0010, 0X0000, 0X0000 |
| 0X0000 | 0 | 0X0000 | 0X00 | 0X0000 | 0X00 | 0X00 | 0x001F | 0X0000 | 0X0000 | 0X00, 0X00, 0x001F, 0X0000, 0X0000 |
| 0X0000 | 0 | 0X0000 | 0X00 | 0X0000 | 0X00 | 0X00 | 0X8606 | 0X0000 | 0X0000 | 0X00, 0X00, 0X8606, 0X0000, 0X0000 |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0x36 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0 | 0X0057 | 0x44 | 0X0000 | 0X00 | 0X00 | 0x8A0A | 0X0000 | 0X0000 | 0X00, 0X00, 0x8A0A, 0X0000, 0X0000 |
| 0X0000 | 0 | 0X0058 | 0x44 | 0X0000 | 0X00 | 0X00 | 0X001F | 0X0000 | 0X0000 | 0X00, 0X00, 0X001F, 0X0000, 0X0000 |
| 0X0000 | 0x2F | 0X0059 | 0x44 | 0X0000 | 0X00 | 0X00 | 0x8A0A | 0X0000 | 0X0000 | 0X00, 0X00, 0x8A0A, 0X0000, 0X0000 |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000 |
| 0X0000 | 0 | 0X0000 | 0X00 | 0X7046 | 0X00 | 0X01 | 0X0101 | 0X0000 | 0X0000 | 0X00, 0X01, 0X0101, 0X0000, 0X0000 |

FIG. 8J1

| STATE INDEX | STATE DESCRIPTION | SPACMD | FBACMD | STMCMD | OBACMD | SPASTAT | FBASTAT | STMSTAT | OBASTAT |
|---|---|---|---|---|---|---|---|---|---|
| 436 | | 0X0000 | 0X0000 | 0X0000 | 0X0000 | 0X00 | 0X00 | 0X00 | 0X00 |
| 437 | | 0X0000 | 0X0000 | 0X0000 | 0X0000 | 0X00 | 0X00 | 0X00 | 0X00 |
| 438 | UNCONDITIONALLY BRANCH TO GO | 0X0000 | 0X0000 | 0X0000 | 0X0000 | 0X00 | 0X00 | 0X00 | 0X00 |
| 439 | END OF SW | 0X0000 | 0X0000 | 0X0000 | 0X0000 | 0X00 | 0X00 | 0X00 | 0X00 |
| 440 | MW WAKEUP FROM INTERMEDIATE STANDBY PERIOD - TURN STROBE | 0X0000 | 0X0000 | 0X0000 | 0X0000 | 0X00 | 0X00 | 0X00 | 0X00 |
| 441 | | 0X0000 | 0X0000 | 0X0000 | 0X0000 | 0X00 | 0X00 | 0X00 | 0X00 |
| 442 | | 0X0000 | 0X0000 | 0X0000 | 0X0000 | 0X00 | 0X00 | 0X00 | 0X00 |
| 443 | UNCONDITIONALLY BRANCH TO GO | 0X0000 | 0X0000 | 0X0000 | 0X0000 | 0X00 | 0X00 | 0X00 | 0X00 |
| 444 | END OF MW | 0X0000 | 0X0000 | 0X0000 | 0X0000 | 0X00 | 0X00 | 0X00 | 0X00 |
| 445 | LW WAKEUP FROM LONG STANDBY PERIOD - TURN STROBE ON | 0X0000 | 0X0000 | 0X0000 | 0X0000 | 0X00 | 0X00 | 0X00 | 0X00 |
| 446 | | 0X0000 | 0X0000 | 0X0000 | 0X0000 | 0X00 | 0X00 | 0X00 | 0X00 |
| 447 | | 0X0000 | 0X0000 | 0X0000 | 0X0000 | 0X00 | 0X00 | 0X00 | 0X00 |
| 448 | UNCONDITIONALLY BRANCH TO GO | 0X0000 | 0X0000 | 0X0000 | 0X0000 | 0X00 | 0X00 | 0X00 | 0X00 |
| 449 | END OF LW | 0X0000 | 0X0000 | 0X0000 | 0X0000 | 0X00 | 0X00 | 0X00 | 0X00 |
| 450 | SD SHUTDOWN - AUTO SHUTDOWN AFTER STANDBY TIMER EXPIRED | 0X0000 | 0X0000 | 0X0000 | 0X0000 | 0X00 | 0X00 | 0X00 | 0X00 |
| 451 | TURN STROBE OFF | 0X0000 | 0X0000 | 0X0000 | 0X0000 | 0X00 | 0X00 | 0X00 | 0X00 |
| 452 | | 0X0000 | 0X0000 | 0X0000 | 0X0000 | 0X00 | 0X00 | 0X00 | 0X00 |
| 453 | END OF SD | 0X0000 | 0X0000 | 0X0000 | 0X0000 | 0X00 | 0X00 | 0X00 | 0X00 |
| 454 | START DL (DILUENT); TO TEST TUBE | TT | 0X0000 | 0X0000 | 0X0000 | 0x11 | 0x00 | 0X00 | 0X00 |
| 455 | | 0X0000 | 0X0000 | 0X0000 | 0X0000 | 0xFF | 0x00 | 0X00 | 0X00 |
| 456 | START SHEATH FOR BACKGROUND CAPTURE | SB | 0X0000 | 0X0000 | 0X0000 | 0x31 | 0X00 | 0X00 | 0X00 |
| 457 | WAIT FOR SB COMPLETE | 0X0000 | 0X0000 | 0X0000 | 0X0000 | 0xFF | 0x00 | 0X00 | 0X00 |
| 458 | TIMER DELAY | 0X0000 | 0X0000 | 0X0000 | 0X0000 | 0x00 | 0x00 | 0x00 | 0x00 |
| 459 | TURN OFF EP PUMP ON SPA | EB | 0X0000 | 0X0000 | 0X0000 | 0x34 | 0x00 | 0X00 | 0X00 |
| 460 | WAIT FOR EB COMPLETE | 0X0000 | 0X0000 | 0X0000 | 0X0000 | 0xFF | 0x00 | 0X00 | 0X00 |
| 461 | MOVE PIPETTE DOWN TO ASPIRATE POSITION IN TEST TUBE | TD | 0X0000 | 0X0000 | 0X0000 | 0X13 | 0x00 | 0X00 | 0X00 |
| 462 | WAIT FOR TD COMPLETE | 0X0000 | 0X0000 | 0X0000 | 0X0000 | 0xFF | 0x00 | 0X00 | 0X00 |
| 463 | START ASPIRATION FOR SAMPLE TRANSFER | AS | RC | 0X0000 | 0X0000 | 0x17 | 0x00 | 0X00 | 0X00 |
| 464 | WAIT FOR AS AND RC COMPLETE | 0X0000 | 0X0000 | 0X0000 | 0X0000 | 0xFF | 0xFF | 0X00 | 0X00 |
| 465 | TIMER DELAY | 0X0000 | 0X0000 | 0X0000 | 0X0000 | 0x00 | 0X00 | 0X00 | 0X00 |
| 466 | TURN OFF EP PUMP ON SPA, SP PUMP ON FBA | EB | EB | 0X0000 | 0X0000 | 0x34 | 0x00 | 0X00 | 0X00 |
| 467 | WAIT FOR EB'S COMPLETE (SPA AND FBA) | 0X0000 | 0X0000 | 0X0000 | 0X0000 | 0xFF | 0xFF | 0X00 | 0X00 |
| 468 | TO WASTE WELL | TW | DB | 0X0000 | 0X0000 | 0x15 | 0x00 | 0X00 | 0X00 |
| 469 | | 0X0000 | 0X0000 | 0X0000 | 0X0000 | 0xFF | 0x00 | 0X00 | 0X00 |
| 470 | | 0X0000 | 0X0000 | 0X0000 | 0X0000 | 0x00 | 0xFF | 0X00 | 0X00 |
| 471 | TURN ON RINSE PUMP AND RINSE PIPETTER | TR | RP | 0X0000 | 0X0000 | 0X00 | 0x25 | 0X00 | 0X00 |
| 472 | | 0X0000 | 0X0000 | 0X0000 | 0X0000 | 0xFF | 0x00 | 0X00 | 0X00 |
| 473 | | 0X0000 | 0X0000 | 0X0000 | 0X0000 | 0x00 | 0xFF | 0X00 | 0X00 |
| 474 | CLEAR PIPETTER/HOME CP AND SP | CP | HC | 0X0000 | 0X0000 | 0X16 | 0X00 | 0X00 | 0X00 |
| 475 | | 0X0000 | 0X0000 | 0X0000 | 0X0000 | 0xFF | 0x00 | 0X00 | 0X00 |
| 476 | | 0X0000 | 0X0000 | 0X0000 | 0X0000 | 0x00 | 0xFF | 0X00 | 0X00 |
| 477 | | 0X0000 | 0X0000 | 0X0000 | 0X0000 | 0x00 | 0x00 | 0xFF | 0X00 |
| 478 | RETRIEVE TUBE NUMBER; BRANCH TO KILL ("KL") IF 10 (0X0A), TERM OTHERWISE | 0X0000 | 0X0000 | 0X0708 | 0X0000 | 0X00 | 0X00 | 0x0A | 0X00 |
| 479 | MOVE TO NEXT TUBE POSITION | 0X0000 | 0X0000 | MN | 0X0000 | 0X00 | 0X00 | 0X32 | 0X00 |
| 480 | BRANCH TO "16" (GO RESUME) | 0X0000 | 0X0000 | 0X0000 | 0X0000 | 0X00 | 0X00 | 0X00 | 0X00 |
| 481 | END OF DL SEQUENCE | 0X0000 | 0X0000 | 0X0000 | 0X0000 | 0X00 | 0X00 | 0X00 | 0X00 |
| 482 | START KL (KILL); SEND CR TO STM; HS TO FBA+C240; HOME PIPETTOR; FLASH STANDBY | PH | HS | CR | 0X0000 | 0x12 | 0x21 | 0X33 | 0X00 |
| 483 | FLASH STANDBY | 0x0000 | 0X0000 | 0X0000 | 0X0000 | 0x00 | 0x00 | 0x00 | 0X00 |
| 484 | SEND SMCSISINSHUTDOWN MESSAGE TO SM; NO EXIT CONDITION! | 0x0000 | 0X0000 | 0X0000 | 0X0000 | 0x00 | 0x00 | 0X00 | 0X00 |
| 485 | END OF KL SEQUENCE | 0X0000 | 0X0000 | 0X0000 | 0X0000 | 0X00 | 0X00 | 0X00 | 0X00 |
| 486 | BX BACKGROUND ERROR EXIT | EB | EB | 0X0000 | 0X0000 | 0X00 | 0X00 | 0X00 | 0X00 |
| 487 | DUMMY | 0X0000 | 0X0000 | 0X0000 | 0X0000 | 0X00 | 0X00 | 0X00 | 0X00 |

FIG. 8J2

| SMTST | TOSM | TVALUE | TFUNC | SENS | STST | SMSK | END | BRAN | DEST | TRANSLATED PARAMETERS |
|---|---|---|---|---|---|---|---|---|---|---|
| 0X0000 | 0 | 0X0000 | 0X00 | 0X0000 | 0X00 | 0X00 | 0X0101 | 0X0000 | 0X0000 | 0X00, 0X00, 0X0101, 0X0000, 0X0000}, |
| 0X0000 | 0 | 0X0000 | 0X00 | 0X0000 | 0X00 | 0X00 | 0X0101 | 0X0000 | 0X0000 | 0X00, 0X00, 0X0101, 0X0000, 0X0000}, |
| 0X0000 | 0 | 0X0000 | 0X00 | 0X0000 | 0X00 | 0X00 | 0x0000 | 0x0101 | 0X474F | 0X00, 0X00, 0x0000, 0X0101, 0X474F}, |
| 0X0000 | 0 | 0X0000 | 0X00 | 0X0000 | 0X00 | 0X00 | 0X0101 | 0X0000 | 0X0000 | 0X00, 0X00, 0X0101, 0X0000, 0X0000}, |
| 0X0000 | 0 | 0X0000 | 0X00 | 0X7046 | 0X00 | 0X01 | 0X0101 | 0X0000 | 0X0000 | 0X00, 0X01, 0X0101, 0X0000, 0X0000}, |
| 0X0000 | 0 | 0X0000 | 0X00 | 0X0000 | 0X00 | 0X00 | 0X0101 | 0X0000 | 0X0000 | 0X00, 0X00, 0X0101, 0X0000, 0X0000}, |
| 0X0000 | 0 | 0X0000 | 0X00 | 0X0000 | 0X00 | 0X00 | 0X0101 | 0X0000 | 0X0000 | 0X00, 0X00, 0X0101, 0X0000, 0X0000}, |
| 0X0000 | 0 | 0X0000 | 0X00 | 0X0000 | 0X00 | 0X00 | 0x0000 | 0x0101 | 0X474F | 0X00, 0X00, 0X0000, 0X0101, 0X474F}, |
| 0X0000 | 0 | 0X0000 | 0X00 | 0X0000 | 0X00 | 0X00 | 0X0101 | 0X0000 | 0X0000 | 0X00, 0X00, 0X0101, 0X0000, 0X0000}, |
| 0X0000 | 0 | 0X0000 | 0X00 | 0X7046 | 0X00 | 0X01 | 0X0101 | 0X0000 | 0X0000 | 0X00, 0X01, 0X0101, 0X0000, 0X0000}, |
| 0X0000 | 0 | 0X0000 | 0X00 | 0X0000 | 0X00 | 0X00 | 0X0101 | 0X0000 | 0X0000 | 0X00, 0X00, 0X0101, 0X0000, 0X0000}, |
| 0X0000 | 0 | 0X0000 | 0X00 | 0X0000 | 0X00 | 0X00 | 0X0101 | 0X0000 | 0X0000 | 0X00, 0X00, 0X0101, 0X0000, 0X0000}, |
| 0X0000 | 0 | 0X0000 | 0X00 | 0X0000 | 0X00 | 0X00 | 0x0000 | 0x0101 | 0X474F | 0X00, 0X00, 0x0000, 0x0101, 0X474F}, |
| 0X0000 | 0 | 0X0000 | 0X00 | 0X0000 | 0X00 | 0X00 | 0X0101 | 0X0000 | 0X0000 | 0X00, 0X00, 0X0101, 0X0000, 0X0000}, |
| 0X0000 | 0 | 0X0000 | 0X00 | 0XB030 | 0x05 | 0x43 | 0x0001 | 0X0101 | 453 | 0x05, 0x43, 0x0001, 0X0101, 453}, |
| 0X0000 | 0 | 0X0000 | 0X00 | 0X7000 | 0X00 | 0X01 | 0X0101 | 0X0000 | 0X0000 | 0X00, 0X01, 0X0101, 0X0000, 0X0000}, |
| 0X0000 | 0 | 0X0000 | 0X00 | 0X0000 | 0X00 | 0X00 | 0X0101 | 0X0000 | 0X0000 | 0X00, 0X00, 0X0101, 0X0000, 0X0000}, |
| 0X0000 | 0 | 0X0000 | 0X00 | 0X0000 | 0X00 | 0X00 | 0X0101 | 0X0000 | 0X0000 | 0X00, 0X00, 0X0101, 0X0000, 0X0000}, |
| 0X0000 | 0x34 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0x001F | 0X0000 | 0X0000 | 0X00, 0X00, 0x001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X005A | 0x42 | 0X0000 | 0x00 | 0x00 | 0x0000 | 0x0000 | 0X0000 | 0x00, 0x00, 0x0000, 0x0000, 0x0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0x8606 | 0X0000 | 0X0000 | 0X00, 0X00, 0x8606, 0X0000, 0X0000}, |
| 0X0000 | 0x32 | 0x0067 | 0x42 | 0X0000 | 0X00 | 0X00 | 0X0010 | 0X0000 | 0X0000 | 0X00, 0X00, 0X0010, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X8606 | 0X0000 | 0X0000 | 0X00, 0X00, 0X8606, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0x32 | 0X005D | 0x44 | 0X0000 | 0X00 | 0X00 | 0X0101 | 0X0008 | 0x4B4C | 0X00, 0X00, 0X0101, 0X0008, 0x4B4C}, |
| 0X0000 | 0x36 | 0X005E | 0x44 | 0X0000 | 0X00 | 0X00 | 0X001F | 0X0000 | 0X0000 | 0X00, 0X00, 0X001F, 0X0000, 0X0000}, |
| 0X0000 | 0x32 | 0X0000 | 0X00 | 0X0000 | 0X00 | 0X00 | 0X0000 | 0X0101 | 0x3136 | 0X00, 0X00, 0X0000, 0X0101, 0x3136}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0X005F | 0x44 | 0x0000 | 0x00 | 0X00 | 0x8E0E | 0X0000 | 0X0000 | 0x00, 0X00, 0x8E0E, 0X0000, 0X0000}, |
| 0X0000 | 0x00 | 0x0000 | 0x00 | 0x6001 | 0x10 | 0X00 | 0X0101 | 0X0000 | 0X0000 | 0x10, 0X00, 0x0101, 0X0000, 0X0000}, |
| 0X0000 | 0x35 | 0x0000 | 0x00 | 0X0000 | 0X00 | 0X00 | 0x0000 | 0X0000 | 0X0000 | 0X00, 0X00, 0x0000, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |
| 0X0000 | 0 | 0x0060 | 0x44 | 0X0000 | 0X00 | 0X00 | 0x0000 | 0X0000 | 0X0000 | 0X00, 0X00, 0x0000, 0X0000, 0X0000}, |
| 0X0000 | 0 | 0X0000 | 0X00 | 0X0000 | 0X00 | 0X00 | 0X001F | 0X0000 | 0X0000 | 0X00, 0X00, 0X001F, 0X0000, 0X0000}, |

| 402 | 404 | 406 | 408 | 410 | 412 | 414 | 416 |

| STATE ORDER | STATE DESCRIPTION | ENERGIZED (VALVES ONLY) | EP | FIRST MOTOR | SECOND MOTOR | SP | SENSOR SELECT |
|---|---|---|---|---|---|---|---|
| 0 | IDLE | | 0 | 80FF | 0 | 80FF | 0000 |
| 1 | "TT" HOME EVACUATION PUMP / ROTATE OUT TO TUBE | J7 AIR CHRG VLV, EBV3, | 80FD | 80FF | 8441 | 80FF | 0000 |
| 2 | PLACE ROLLER ON TUBE (EP -45 DEG) | EBV3, | 860C | 80FF | 0 | 80FF | 0000 |
| 3 | DUMMY | | 80FF | 80FF | 0 | 80FF | 0000 |
| 4 | "PH" - HOME VERTICAL TO LIFT PIPPETTER AND SEND PIPPETER BACK TO BACK SENSOR THEN TO WASTE WELL | | 80FF | 80FE | 80FF | 80FF | 0000 |
| 5 | HOME ROTATIONAL MOTOR TO BACK SENSOR | | 80FF | 80FF | 80FE | 80FF | 0000 |
| 6 | ROTATE OUT -3 DEG TO WASTE WELL | | 80FF | 80FF | 8440 | 80FF | 0000 |
| 7 | CHECKING PRESSURE | J7 AIR CHRG VLV, | 80FF | 80FF | 0 | 80FF | 10B0 |
| 8 | RECHARGE | J7 AIR CHRG VLV, | 80FF | 80FF | 0 | 80FF | 10B0 |
| 9 | DUMMY | | 80FF | 80FF | 0 | 80FF | 0000 |
| 10 | "TD" - DOWN TO TEST TUBE | | 0 | 8643 | 0 | 80FF | 0000 |
| 11 | DUMMY | | 80FF | 80FF | 0 | 80FF | 0000 |
| 12 | "AS" - MIX SAMPLE (BP 1.5 SEC) | J10 BURP VLV, CBV3, EBV3, | 80FF | 80FF | 0 | 80FF | 0000 |
| 13 | DELAY BEFORE ASPIRATE | CBV3, EBV3, | 80FF | 80FF | 0 | 80FF | 0000 |
| 14 | ASPIRATE TO BEGINNING OF FLOW CELL | SI, J7 AIR CHRG VLV, CBV3, PBV3 | 4009 | 80FF | 0 | 80FF | 0000 |
| 15 | ACTIVATE SBV TO FILL FLOW CELL WHILE PULLING EP DURING FAST | SBV3, | 4022 | 80FF | 0 | 80FF | 0000 |
| 16 | ACTIVATE SBV TO FILL FLOW CELL WHILE PULLING EP DURING SLOW PUSH OF CP DURING ANALYSIS | SBV3, | 401D | 80FF | 0 | 80FF | 0000 |
| 17 | DUMMY | SBV3, | 0 | 80FF | 0 | 80FF | 0000 |
| 18 | "TW" LIFT PIPPETTER TO 2/3 OF THE TUBE | | 80FF | D556 | 0 | 80FF | 0000 |
| 19 | LIFT PIPPETER TO THE TOP AND SPIT AIR | J10 BURP VLV, | 80FF | 80FE | 0 | 80FF | 0000 |
| 20 | ROTATE IN TO WASTE WELL | | 80FF | 80FF | 8442 | 80FF | 0000 |
| 21 | DOWN TO WASTE WELL | | 80FF | 8647 | 0 | 80FF | 0000 |
| 22 | DUMMY | | 80FF | 80FF | 0 | 80FF | 0000 |
| 23 | "CP" CLEAN FLOWCELL WINDOW FOR 2 SEC | CBV3, SBV3, | 4019 | 80FF | 0 | 80FF | 0000 |
| 24 | RAISE PIPPETTER | | 80FF | D556 | 0 | 80FF | 0000 |
| 25 | CLEAR PIPPETTER | J10 BURP VLV, | 80FF | 80FF | 0 | 80FF | 0000 |
| 26 | LIFT PIPPETER | | 80FF | 80FE | 0 | 80FF | 0000 |
| 27 | DUMMY | | 80FF | 80FF | 0 | 80FF | 0000 |
| 28 | "PS" PRIME SHEATH SUPPLY LINE | | 80FF | 80FF | 0 | 80FF | 0000 |
| 29 | DUMMY | | 80FF | 80FF | 0 | 80FF | 0000 |

| 418 | 420 | 422 | 424 | 426 | 428 | 430 | 432 | 434 | 436 |
|---|---|---|---|---|---|---|---|---|---|
| SENSOR STATE | SENSOR MASK | MOTOR TEST | SM TEST | TOSM | TVALUE | TFUNC | END CTRL | BRAN CTRL | DEST |
| 0 | 0 | 0 | 0X0000 | 0xFF | 0X0 | 0X0000 | 0x0007 | 0x0000 | 0x0000 |
| 0 | 0 | FB | 0X0000 | 0X11 | 0X0 | 0X0000 | 0x0007 | 0x0000 | 0x0000 |
| 0 | 0 | B3 | 0X0000 | 0X11 | 0X0 | 0X0000 | 0x0007 | 0x0000 | 0x0000 |
| 0 | 0 | F3 | 0X0000 | 0X11 | 0X0 | 0X0000 | 0x0007 | 0x0000 | 0x0000 |
| 0 | 0 | FF | 0X0000 | 0X00 | 0X0 | 0X0000 | 0x0007 | 0x0000 | 0x0000 |
| 0 | 0 | FF | 0X0000 | 0X00 | 0X0 | 0X0000 | 0X0007 | 0X0000 | 0X0000 |
| 0 | 0 | FB | 0X0000 | 0X00 | 0X0 | 0X0000 | 0x0007 | 0x0000 | 0x0000 |
| 6 | 54 | F3 | 0X0000 | 0X00 | 0X0 | 0X0000 | 0x0001 | 0x0101 | 9 |
| 5 | 54 | F3 | 0X0000 | 0X00 | 0X0 | 0X0000 | 0x0001 | 0x0000 | 0x0000 |
| 0 | 0 | F3 | 0X0000 | 0X12 | 0X0 | 0X0000 | 0x0007 | 0x0000 | 0x0000 |
| 0 | 0 | 23 | 0X0000 | 0X13 | 0X0 | 0X0000 | 0x0007 | 0x0000 | 0x0000 |
| 0 | 0 | F3 | 0X0000 | 0X13 | 0X0 | 0X0000 | 0x0007 | 0x0000 | 0x0000 |
| 0 | 0 | F3 | 0X0000 | 0X17 | 0x42 | 0x0004 | 0x0000 | 0x0000 | 0x0000 |
| 0 | 0 | F3 | 0X0000 | 0X17 | 0X42 | 0X0023 | 0X0000 | 0x0000 | 0x0000 |
| 0 | 0 | 33 | 0X0000 | 0X17 | 0x42 | 0X0024 | 0x0000 | 0x0000 | 0x0000 |
| 0 | 0 | 33 | 0X0000 | 0X17 | 0x42 | 0X0025 | 0x0000 | 0x0000 | 0x0000 |
| 0 | 0 | 33 | 0X0000 | 0X17 | 0x00 | 0x0000 | 0x0007 | 0x0000 | 0x0000 |
| 0 | 0 | 33 | 0X0000 | 0X17 | 0X0 | 0X0000 | 0x0007 | 0x0000 | 0x0000 |
| 0 | 0 | E3 | 0X0000 | 0X00 | 0X0 | 0X0000 | 0x0007 | 0x0000 | 0x0000 |
| 0 | 0 | F3 | 0X0000 | 0X00 | 0X0 | 0X0000 | 0x0007 | 0x0000 | 0x0000 |
| 0 | 0 | FB | 0X0000 | 0x00 | 0X0 | 0X0000 | 0x0007 | 0x0000 | 0x0000 |
| 0 | 0 | E3 | 0X0000 | 0X00 | 0X0 | 0X0000 | 0x0007 | 0x0000 | 0x0000 |
| 0 | 0 | F3 | 0X0000 | 0X15 | 0X0 | 0X0000 | 0x0007 | 0x0000 | 0x0000 |
| 0 | 0 | 33 | 0X0000 | 0X00 | 0X42 | 0X0027 | 0x0000 | 0x0000 | 0x0000 |
| 0 | 0 | E3 | 0X0000 | 0x16 | 0X0 | 0X0000 | 0x0007 | 0x0000 | 0x0000 |
| 0 | 0 | F3 | 0X0000 | 0x16 | 0X42 | 0X0005 | 0X0000 | 0x0000 | 0x0000 |
| 0 | 0 | F3 | 0X0000 | 0x16 | 0X0 | 0X0000 | 0x0007 | 0x0000 | 0x0000 |
| 0 | 0 | F3 | 0X0000 | 0X16 | 0X0 | 0X0000 | 0x0007 | 0x0000 | 0x0000 |
| 0 | 0 | F3 | 0X0000 | 0X00 | 0X42 | 0X0028 | 0x0000 | 0x0000 | 0x0000 |
| 0 | 0 | F3 | 0X0000 | 0X20 | 0X0 | 0X0000 | 0x0007 | 0x0000 | 0x0000 |

| STATE ORDER | STATE DESCRIPTION | ENERGIZED (VALVES ONLY) | EP | FIRST MOTOR | SECOND MOTOR | SP | SENSOR SELECT |
|---|---|---|---|---|---|---|---|
| 30 | "PP" PRIME EVACUATION PUMP | EBV3, | D758 | 80FF | 0 | 80FF | 0000 |
| 31 | HOLD EBV3 FOR 3 SEC | EBV3, | 80FF | 80FF | 0 | 80FF | 0000 |
| 32 | DUMMY | | 80FF | 80FF | 0 | 80FF | 0000 |
| 33 | "PL" HOME EP | EBV3, | 80FD | 80FF | 0 | 80FF | 0000 |
| 34 | PRIME INNER LINE #2 | CBV3, SBV3, | DB5C | 80FF | 0 | 80FF | 0000 |
| 35 | DUMMY | | 80FF | 80FF | 0 | 80FF | 0000 |
| 36 | "TR" TURN ON RINSE PUMP FOR 2 SEC | | 80FF | 80FF | 0 | 80FF | 0000 |
| 37 | CHECKING PRESSURE | J7 AIR CHRG | 80FF | 80FF | 0 | 80FF | 10B0 |
| 38 | RECHARGE | J7 AIR CHRG | 80FF | 80FF | 0 | 80FF | 10B0 |
| 39 | FILL SHEATH TANK FOR 2 SEC | VLV, | 80FF | 80FF | 0 | 80FF | 0000 |
| 40 | DUMMY | | 80FF | 80FF | 0 | 80FF | 0000 |
| 41 | "HP" HOME EP | EBV3, | 80FD | 80FF | 0 | 80FF | 0000 |
| 42 | DUMMY | | 80FF | 80FF | 0 | 80FF | 0000 |
| 43 | "SB" TRANSFER SHEATH DURING BACKGROUND | CBV3, SBV3, | 401A | 80FF | 0 | 80FF | 0000 |
| 44 | DUMMY | CBV3, SBV3, | 0 | 80FF | 0 | 80FF | 0000 |
| 45 | "EB" END BACKGROUND (EP OFF) | CBV3, SBV3, | 80FF | 80FF | 0 | 80FF | 0000 |
| 46 | DUMMY | | 80FF | 80FF | 0 | 80FF | 0000 |
| 47 | "DF" DRAIN FLOWCELL | PBV3, | DE5F | 80FF | 0 | 80FF | 0000 |
| 48 | DUMMY | | 80FF | 80FF | 0 | 80FF | 0000 |
| 49 | "IC" HOME EP | EBV3, | 80FD | 80FF | 0 | 80FF | 0000 |
| 50 | PLACE ROLLER ON TUBE (EP -45 DEG) | EBV3, | 860C | 80FF | 0 | 80FF | 0000 |
| 51 | DOWN TO TEST TUBE | PBV3, | 80FF | 8643 | 0 | 80FF | 0000 |
| 52 | WASH FLOW CELL WITH IRISOLVE | PBV3, | E061 | 80FF | 0 | 80FF | 0000 |
| 53 | DUMMY | | 80FF | 80FF | 0 | 80FF | 0000 |
| 54 | START "ZZ" | | 0 | 80FF | 0 | 80FF | 0000 |
| 55 | END "ZZ" | | 0 | 80FF | 0 | 80FF | 0000 |
| 56 | "RV" RESET VALVES (SUBROUTINE TO BE USED ONLY DURING "BD" TO TURN OFF VALVES) | | 80FF | 80FF | 0 | 80FF | 0000 |
| 57 | DUMMY | | 80FF | 80FF | 0 | 80FF | 0000 |
| 58 | "FP" CHECKING PRESSURE | | 80FF | 80FF | 0 | 80FF | 10B0 |
| 59 | RECHARGE | | 80FF | 80FF | 0 | 80FF | 10B0 |
| 60 | DUMMY | | 80FF | 80FF | 0 | 80FF | 0000 |
| 61 | "S1" TURN ON SHEATH FILL PUMP | | 80FF | 80FF | 0 | 80FF | 0000 |
| 62 | DUMMY | | 80FF | 80FF | 0 | 80FF | 0000 |

| SENSOR STATE | SENSOR MASK | MOTOR TEST | SM TEST | TOSM | TVALUE | TFUNC | END CTRL | BRAN CTRL | DEST |
|---|---|---|---|---|---|---|---|---|---|
| 0 | 0 | B3 | 0X0000 | 0X00 | 0X0000 | 0X0 | 0x0007 | 0x0000 | 0x0000 |
| 0 | 0 | F3 | 0X0000 | 0x00 | 0X0029 | 0X42 | 0x0000 | 0x0000 | 0x0000 |
| 0 | 0 | F3 | 0X0000 | 0X21 | 0X0000 | 0X0 | 0x0007 | 0x0000 | 0x0000 |
| 0 | 0 | F3 | 0X0000 | 0X00 | 0X0000 | 0X0 | 0x0007 | 0x0000 | 0x0000 |
| 0 | 0 | B3 | 0X0000 | 0X00 | 0X0000 | 0X0 | 0x0007 | 0x0000 | 0x0000 |
| 0 | 0 | F3 | 0X0000 | 0x22 | 0X0000 | 0X0 | 0x0007 | 0x0000 | 0x0000 |
| 0 | 0 | F3 | 0X0000 | 0x23 | 0X002A | 0X42 | 0x0000 | 0x0000 | 0x0000 |
| 6 | 54 | F3 | 0X0000 | 0x23 | 0X0000 | 0X0 | 0x0001 | 0x0101 | 38 |
| 5 | 54 | F3 | 0X0000 | 0x23 | 0X0000 | 0X0 | 0x0001 | 0x0000 | 0x0000 |
| 0 | 0 | F3 | 0X0000 | 0x23 | 0x0006 | 0x42 | 0x0000 | 0x0000 | 0x0000 |
| 0 | 0 | F3 | 0X0000 | 0x23 | 0X0000 | 0X0 | 0x0007 | 0x0000 | 0x0000 |
| 0 | 0 | F3 | 0X0000 | 0X00 | 0X0000 | 0X0 | 0x0007 | 0x0000 | 0x0000 |
| 0 | 0 | F3 | 0X0000 | 0X24 | 0X0000 | 0X0 | 0x0007 | 0x0000 | 0x0000 |
| 0 | 0 | 33 | 0X0000 | 0X31 | 0x0000 | 0x0 | 0x0101 | 0x0000 | 0x0000 |
| 0 | 0 | 33 | 0X0000 | 0X31 | 0X0000 | 0X0 | 0x0000 | 0x0000 | 0x0000 |
| 0 | 0 | F3 | 0X0000 | 0X34 | 0x0000 | 0x0 | 0x0007 | 0x0000 | 0x0000 |
| 0 | 0 | F3 | 0X0000 | 0X34 | 0X0000 | 0X0 | 0x0007 | 0x0000 | 0x0000 |
| 0 | 0 | B3 | 0X0000 | 0X00 | 0X0000 | 0X0 | 0x0007 | 0x0000 | 0x0000 |
| 0 | 0 | F3 | 0X0000 | 0X26 | 0X0000 | 0X0 | 0x0007 | 0x0000 | 0x0000 |
| 0 | 0 | F3 | 0X0000 | 0X00 | 0X0000 | 0X0 | 0x0007 | 0x0000 | 0x0000 |
| 0 | 0 | B3 | 0X0000 | 0X00 | 0X0000 | 0X0 | 0x0007 | 0x0000 | 0x0000 |
| 0 | 0 | E3 | 0X0000 | 0X00 | 0X0000 | 0X0 | 0x0007 | 0x0000 | 0x0000 |
| 0 | 0 | B3 | 0X0000 | 0X00 | 0x0000 | 0x0 | 0x0007 | 0x0000 | 0x0000 |
| 0 | 0 | F3 | 0X0000 | 0X27 | 0x0000 | 0x0 | 0x0007 | 0x0000 | 0x0000 |
| 0 | 0 | 0 | 0X0000 | 0xFF | 0x0000 | 0x0 | 0x0000 | 0x0080 | 0x0000 |
| 0 | 0 | 0 | 0X0000 | 0xFF | 0x0000 | 0x0 | 0x0000 | 0x0000 | 0x0000 |
| 0 | 0 | F3 | 0X0000 | 0X00 | 0X0000 | 0X0 | 0x0007 | 0x0000 | 0x0000 |
| 0 | 0 | F3 | 0X0000 | 0X26 | 0X0000 | 0X0 | 0x0007 | 0x0000 | 0x0000 |
| 6 | 54 | F3 | 0X0000 | 0X00 | 0X0000 | 0X0 | 0x0001 | 0x0101 | 60 |
| 5 | 54 | F3 | 0X0000 | 0X00 | 0X0000 | 0X0 | 0x0001 | 0x0000 | 0x0000 |
| 0 | 0 | F3 | 0X0000 | 0x30 | 0X0000 | 0X0 | 0x0007 | 0x0000 | 0x0000 |
| 0 | 0 | F3 | 0X0000 | 0X32 | 0x0000 | 0x0 | 0x0101 | 0x0000 | 0x0000 |
| 0 | 0 | F3 | 0X0000 | 0X32 | 0X0000 | 0X0 | 0x0000 | 0x0000 | 0x0000 |

FIG. 9C1

| STATE ORDER | STATE DESCRIPTION | ENERGIZED (VALVES ONLY) | EP | FIRST MOTOR | SECOND MOTOR | SP | SENSOR SELECT |
|---|---|---|---|---|---|---|---|
| 63 | "SO" TURN OFF SHEATH FILL PUMP | | 80FF | 80FF | 0 | 80FF | 0000 |
| 64 | DUMMY | | 80FF | 80FF | 0 | 80FF | 0000 |
| 65 | "TQ" TURN ON RINSE PUMP FOR 2 SEC WITHOUT FILL SHEALTH | | 80FF | 80FF | 0 | 80FF | 0000 |
| 66 | CHECKING PRESSURE | 17 AIR CHRG VLV, | 80FF | 80FF | 0 | 80FF | 10B0 |
| 67 | RECHARGE | 17 AIR CHRG VLV, | 80FF | 80FF | 0 | 80FF | 10B0 |
| 68 | DUMMY | | 80FF | 80FF | 0 | 80FF | 0000 |
| 69 | "HC" INITIALIZE EVACUATION PUMP | 17 AIR CHRG VLV, EBV3, | 80FD | 80FF | 0 | 80FF | 0000 |
| 70 | PLACE ROLLER ON TUBE (EP -45 DEG) | EBV3, | 860C | 80FF | 0 | 80FF | 0000 |
| 71 | DUMMY | | 80FF | 80FF | 0 | 80FF | 0000 |

| SENSOR STATE | SENSOR MASK | MOTOR TEST | SM TEST | TOSM | TVALUE | TFUNC | END CTRL | BRAN CTRL | DEST |
|---|---|---|---|---|---|---|---|---|---|
| 0 | 0 | F3 | 0X0000 | 0X33 | 0X0000 | 0X0 | 0X0101 | 0X0000 | 0X0000 |
| 0 | 0 | F3 | 0X0000 | 0X33 | 0X0000 | 0X0 | 0X0000 | 0X0000 | 0X0000 |
| 0 | 0 | F3 | 0X0000 | 0X23 | 0X002B | 0X42 | 0X0000 | 0X0000 | 0X0000 |
| 6 | 54 | F3 | 0X0000 | 0X23 | 0X0000 | 0X0 | 0X0001 | 0X0101 | 68 |
| 5 | 54 | F3 | 0X0000 | 0X23 | 0X0000 | 0X0 | 0X0001 | 0X0000 | 0X0000 |
| 0 | 0 | F3 | 0X0000 | 0X23 | 0X0000 | 0X0 | 0X0007 | 0X0000 | 0X0000 |
| 0 | 0 | F3 | 0X0000 | 0X27 | 0X0000 | 0X0 | 0X0007 | 0X0000 | 0X0000 |
| 0 | 0 | B3 | 0X0000 | 0X27 | 0X0000 | 0X0 | 0X0007 | 0X0000 | 0X0000 |
| 0 | 0 | F3 | 0X0000 | 0X27 | 0X0000 | 0X0 | 0X0007 | 0X0000 | 0X0000 |

| STATE ORDER | STATE DESCRIPTION | ENERGIZED (VALVES ONLY) | EP | FIRST MOTOR | SECOND MOTOR | SP | SENSOR SELECT |
|---|---|---|---|---|---|---|---|
| 0 | IDLE | | 0 | 80FF | 80FF | 0 | 0000 |
| 1 | "HC" HOME CP AND SP | CBV3, | 80FE | 80FF | 80FF | 80FE | 0000 |
| 2 | PLACE ROLLER ON TUBE (CP 45 DEG) | CBV3, | 8601 | 80FF | 80FF | 80FF | 0000 |
| 3 | DUMMY | | 80FF | 80FF | 80FF | 80FF | 0000 |
| 4 | "PC" PRIME CANNUAL AND SHEATH PUMP | CBV3, | C546 | 80FF | 80FF | CA4B | 0000 |
| 5 | DUMMY | | 80FF | 80FF | 80FF | 80FF | 0000 |
| 6 | "PL" PRIME LINES | DRV3, EBV3, | CC4D | 80FF | 80FF | 80FF | 0000 |
| 7 | DUMMY | | 80FF | 80FF | 80FF | 80FF | 0000 |
| 8 | RINSE PIPETTER -- RP ON | SBV3, PBV3, EBV3, | 80FF | 80FF | 80FF | C849 | 0000 |
| 9 | OPEN SBV, PBV, AND EBV TO VENT EXCESS PRESSURE OUT | SBV3, PBV3, EBV3, | 80FF | 80FF | 80FF | 80FF | 0000 |
| 10 | DUMMY | | 80FF | 80FF | 80FF | 80FF | 0000 |
| 11 | "PA" PRIME ASPARATION LINE | SBV3, PBV3, EBV3, | 80FF | 80FF | 80FF | CE4F | 0000 |
| 12 | DUMMY | | 80FF | 80FF | 80FF | 80FF | 0000 |
| 13 | "HP" HOME CP AND SP | CBV3, | 80FE | 80FF | 80FF | 80FE | 0000 |
| 14 | DUMMY | | 80FF | 80FF | 80FF | 80FF | 0000 |
| 15 | "RC" DELAY BEFORE RUNNING CP FAST PUSH | | 80FF | 80FF | 80FF | 80FF | 0000 |
| 16 | FAST PUSH | | 4001 | 80FF | 80FF | 80FF | 0000 |
| 17 | SLOW CP PUSH DURING ANALYSIS | | 4002 | 80FF | 80FF | 80FF | 0000 |
| 18 | DUMMY | | 0 | 80FF | 80FF | 80FF | 0000 |
| 19 | "DB" PLACE SP ROLLER ON HOSE WITH 45 DEG MOVE | | 80FF | 80FF | 80FF | 8601 | 0000 |
| 20 | DEBUBBLE FOR 3 SECS | CBV3, SBV3, DRV3, EBV3, | 80FF | 80FF | 80FF | C344 | 0000 |
| 21 | DUMMY | | 80FF | 80FF | 80FF | 80FF | 0000 |
| 22 | "DE" DEBUBBLE (SP 10 REV.) | CBV3, SBV3, DRV3, EBV3, | 80FF | 80FF | 80FF | D051 | 0000 |
| 23 | DUMMY | | 80FF | 80FF | 80FF | 80FF | 0000 |
| 24 | BEGIN ZZ | | 0 | 80FF | 80FF | 0 | 0000 |
| 25 | END ZZ | | 0 | 80FF | 80FF | 0 | 0000 |
| 26 | "IC" HOME CP | CBV3, | 80FE | 80FF | 80FF | 80FF | 0000 |
| 27 | PLACE ROLLER ON TUBE (CP 45 DEG) | CBV3, | 8601 | 80FF | 80FF | 80FF | 0000 |
| 28 | CLEAN DRAIN | DRV3, EBV3, | D253 | 80FF | 80FF | 80FF | 0000 |
| 29 | DUMMY | | 80FF | 80FF | 80FF | 80FF | 0000 |

FIG.10A2

| SENSOR STATE | SENSOR MASK | MOTOR TEST | SM TEST | TOSM | TVALUE | TFUNC | END CTRL | BRAN CTRL | DEST |
|---|---|---|---|---|---|---|---|---|---|
| 0 | 0 | 0 | 0X0000 | 0xFF | 0X0000 | 0X0 | 0x0007 | 0x0000 | 0x0000 |
| 0 | 0 | FF | 0X0000 | 0x21 | 0X0000 | 0X0 | 0x0007 | 0x0000 | 0x0000 |
| 0 | 0 | BF | 0X0000 | 0x21 | 0X0000 | 0X0 | 0x0007 | 0x0000 | 0x0000 |
| 0 | 0 | FF | 0X0000 | 0X21 | 0X0000 | 0X0 | 0x0007 | 0x0000 | 0x0000 |
| 0 | 0 | BE | 0X0000 | 0x00 | 0X0000 | 0x0 | 0x0007 | 0x0000 | 0x0000 |
| 0 | 0 | FF | 0X0000 | 0x23 | 0X0000 | 0X0 | 0x0007 | 0x0000 | 0x0000 |
| 0 | 0 | BF | 0X0000 | 0x00 | 0X0000 | 0x0 | 0x0007 | 0x0000 | 0x0000 |
| 0 | 0 | FF | 0X0000 | 0x24 | 0X0000 | 0X0 | 0x0007 | 0x0000 | 0x0000 |
| 0 | 0 | FE | 0X0000 | 0x00 | 0x0000 | 0x0 | 0x0007 | 0x0000 | 0x0000 |
| 0 | 0 | FF | 0X0000 | 0x00 | 0x0014 | 0x42 | 0x0000 | 0x0000 | 0x0000 |
| 0 | 0 | FF | 0X0000 | 0X25 | 0X0000 | 0X0 | 0x0007 | 0x0000 | 0x0000 |
| 0 | 0 | FE | 0X0000 | 0X00 | 0X0000 | 0X0 | 0x0007 | 0x0000 | 0x0000 |
| 0 | 0 | FF | 0X0000 | 0x26 | 0X0000 | 0X0 | 0x0007 | 0x0000 | 0x0000 |
| 0 | 0 | FF | 0X0000 | 0X00 | 0X0000 | 0X0 | 0x0007 | 0x0000 | 0x0000 |
| 0 | 0 | FF | 0X0000 | 0X27 | 0X0000 | 0X0 | 0x0007 | 0x0000 | 0x0000 |
| 0 | 0 | FF | 0X0000 | 0X28 | 0x0015 | 0x42 | 0x0000 | 0x0000 | 0x0000 |
| 0 | 0 | 3F | 0X0000 | 0X28 | 0x0016 | 0x42 | 0x0000 | 0x0000 | 0x0000 |
| 0 | 0 | 3F | 0X0000 | 0X28 | 0X0000 | 0X0 | 0X0007 | 0x0000 | 0x0000 |
| 0 | 0 | 3F | 0X0000 | 0X28 | 0X0000 | 0x0 | 0x0000 | 0x0000 | 0x0000 |
| 0 | 0 | FE | 0X0000 | 0X29 | 0X0000 | 0X0 | 0x0007 | 0x0000 | 0x0000 |
| 0 | 0 | FE | 0X0000 | 0x29 | 0X0000 | 0x0 | 0x0007 | 0x0000 | 0x0000 |
| 0 | 0 | FF | 0X0000 | 0X29 | 0X0000 | 0X0 | 0x0007 | 0x0000 | 0x0000 |
| 0 | 0 | FE | 0X0000 | 0X00 | 0X0000 | 0X0 | 0x0007 | 0x0000 | 0x0000 |
| 0 | 0 | FF | 0X0000 | 0X30 | 0X0000 | 0X0 | 0x0007 | 0x0000 | 0x0000 |
| 0 | 0 | 0 | 0X0000 | 0xFF | 0X0000 | 0X0 | 0x0000 | 0x0080 | 0x0000 |
| 0 | 0 | 0 | 0X0000 | 0xFF | 0X0000 | 0X0 | 0x0000 | 0x0000 | 0x0000 |
| 0 | 0 | FF | 0X0000 | 0X00 | 0X0000 | 0X0 | 0x0007 | 0x0000 | 0x0000 |
| 0 | 0 | BF | 0X0000 | 0X00 | 0X0000 | 0X0 | 0x0007 | 0x0000 | 0x0000 |
| 0 | 0 | BF | 0X0000 | 0X00 | 0X0000 | 0X0 | 0x0007 | 0x0000 | 0x0000 |
| 0 | 0 | FF | 0X0000 | 0X31 | 0X0000 | 0X0 | 0x0007 | 0x0000 | 0x0000 |

FIG.10B1

| STATE ORDER | STATE DESCRIPTION | ENERGIZED (VALVES ONLY) | EP | FIRST MOTOR | SECOND MOTOR | SP | SENSOR SELECT |
|---|---|---|---|---|---|---|---|
| 30 | "RV" RESET VALVES TO OFF (USED INSTEAD OF "RE" DURING "BD" IN HYPERTERMINAL) | | 80FF | 80FF | 80FF | 80FF | 0000 |
| 31 | DUMMY | | 80FF | 80FF | 80FF | 80FF | 0000 |
| 32 | "HS" STANDBY POSITION FOR CP AND SP | CBV3, | 80FE | 80FF | 80FF | 80FE | 0000 |
| 33 | PLACE ROLLER ON TUBE (CP AND SP 45 DEG) | CBV3, | 8601 | 80FF | 80FF | 8601 | 0000 |
| 34 | DUMMY | | 80FF | 80FF | 80FF | 80FF | 0000 |
| 35 | "EB" END CONSTANT VELOCITY SP MOVE | | 80FF | 80FF | 80FF | 80FF | 0000 |
| 36 | DUMMY | | 80FF | 80FF | 80FF | 80FF | 0000 |

500

10B2

FIG.10B2
| SENSOR STATE | SENSOR MASK | MOTOR TEST | SM TEST | TOSM | TVALUE | TFUNC | END CTRL | BRAN CTRL | DEST |
|---|---|---|---|---|---|---|---|---|---|
| 0 | 0 | FF | 0X0000 | 0X00 | 0X0000 | 0X0 | 0X0007 | 0X0000 | 0X0000 |
| 0 | 0 | FF | 0X0000 | 0X30 | 0X0000 | 0X0 | 0X0007 | 0X0000 | 0X0000 |
| 0 | 0 | FF | 0X0000 | 0X00 | 0X0000 | 0X0 | 0X0007 | 0X0000 | 0X0000 |
| 0 | 0 | BE | 0X0000 | 0X00 | 0X0000 | 0X0 | 0X0007 | 0X0000 | 0X0000 |
| 0 | 0 | FF | 0X0000 | 0X21 | 0X0000 | 0X0 | 0X0007 | 0X0000 | 0X0000 |
| 0 | 0 | FF | 0X0000 | 0X34 | 0X0000 | 0X0 | 0X0007 | 0X0000 | 0X0000 |
| 0 | 0 | FF | 0X0000 | 0X34 | 0X0000 | 0X0 | 0X0007 | 0X0000 | 0X0000 |
10B1

FIG. 11A1

| STATE ORDER | STATE DESCRIPTION | DOR | DAND | SM | CM | CI | CO | RC |
|---|---|---|---|---|---|---|---|---|
| 0 | RESET IN GENERAL | 0X00000000 | 0XFFFFFFFF | 0X80FF | 0X80FF | 0X80FF | 0X80FF | 0X0000 |
| 1 | START M1; START HC | 0X00000000 | 0XFFFFFFFF | 0X80FD | 0X0000 | 0X80FF | 0X80FF | 0X0000 |
| 2 | END HC | 0X00000000 | 0XFFFFFFFF | 0X80FF | 0X0000 | 0X80FF | 0X80FF | 0X0000 |
| 3 | START HR | 0X00000000 | 0XFFFFFFFF | 0X80FF | 0X0000 | 0X80FF | 0X80FF | 0X0000 |
| 4 | END HR | 0X00000000 | 0XFFFFFFFF | 0X80FF | 0X0000 | 0X80FF | 0X80FF | 0X0000 |
| 5 | START US; BRANCH IF UPSTREAM NOT READY | 0X00000000 | 0XFFFFFFFF | 0X0000 | 0X0000 | 0X0900 | 0X0000 | 0X0000 |
| 6 | BRANCH IF BUFFER FULL | 0X00000000 | 0XFFFFFFFF | 0X0000 | 0X0000 | 0X0000 | 0X0000 | 0X0000 |
| 7 | SIGNAL OK TO SEND RACK; WAIT FOR COMPLETE SIGNAL (!READY) | 0X00000010 | 0XFFFFFFFF | 0X0000 | 0X0000 | 0X80FF | 0X0000 | 0X0000 |
| 8 | DELAY 200 MS | 0X00000000 | 0XFFFFFFFF | 0X0000 | 0X0000 | 0X0000 | 0X0000 | 0X0000 |
| 9 | UNSIGNAL OK TO SEND RACK; FEED IN 2 SEC | 0X00000000 | 0XFFFFFFFF | 0X0000 | 0X0000 | 0X0900 | 0X0000 | 0X0000 |
| 10 | END US | 0X00000000 | 0XFFFFFFFF | 0X0000 | 0X0000 | 0X80FF | 0X0000 | 0X0000 |
| 11 | WAIT IF NO OTHER RACK | 0X00000000 | 0XFFFFFFFF | 0X0000 | 0X0000 | 0X0000 | 0X0000 | 0X0000 |
| 12 | RUN RACK IN | 0X00000000 | 0XFFFFFFFF | 0X80FF | 0X0000 | 0X0900 | 0X0900 | 0X0000 |
| 13 | EXTRA SECOND TO MAKE FLUSH. READ RACK ID FOR TRANSMISSION | 0X00000000 | 0XFFFFFFFF | 0X80FF | 0X0000 | 0X0900 | 0X0900 | 0X0000 |
| 14 | STOP CONVEYOR; CHECK IF ROOM AT OUTPUT SIDE | 0X00000000 | 0XFFFFFFFF | 0X80FF | 0X0000 | 0X80FF | 0X80FF | 0X0000 |
| 15 | MOVE RACK IN | 0X00000000 | 0XFFFFFFFF | 0X8040 | 0X0000 | 0X80FF | 0X80FF | 0X0000 |
| 16 | GOT RACK | 0X00000000 | 0XFFFFFFFF | 0X0000 | 0X0000 | 0X0000 | 0X0000 | 0X0000 |
| 17 | NO RACK | 0X00000000 | 0XFFFFFFFF | 0X0000 | 0X0000 | 0X0000 | 0X0000 | 0X0000 |
| 18 | END M1; END U2 | 0X00000000 | 0XFFFFFFFF | 0X0000 | 0X0000 | 0X0000 | 0X0000 | 0X0000 |
| 19 | START MN; MOVE TO NEXT TUBE POSITION | 0X00000000 | 0XFFFFFFFF | 0X8000 | 0X0000 | 0X80FF | 0X80FF | 0X0000 |
| 20 | COMPLETE THE MOVE AND GET TUBE NUMBER | 0X00000000 | 0XFFFFFFFF | 0X80FF | 0X0000 | 0X80FF | 0X80FF | 0X0000 |
| 21 | STABILIZE BEFORE READING TUBE DETECTOR | 0X00000000 | 0XFFFFFFFF | 0X80FF | 0X0000 | 0X80FF | 0X80FF | 0X0000 |
| 22 | STORE TUBE DETECTOR VALUE, BRANCH TO SCAN IF TUBE PRESENT | 0X00000000 | 0XFFFFFFFF | 0X80FF | 0X0000 | 0X80FF | 0X80FF | 0X0000 |
| 23 | UNCONDITIONAL BRANCH TO ENDMN | 0X00000000 | 0XFFFFFFFF | 0X80FF | 0X0000 | 0X80FF | 0X80FF | 0X0000 |
| 24 | SCAN BARCODE | 0X00000000 | 0XFFFFFFFF | 0X80FF | 0X0000 | 0X80FF | 0X80FF | 0X0000 |
| 25 | END MN; SEND COMPLETION TO MC | 0X00000000 | 0XFFFFFFFF | 0X80FF | 0X0000 | 0X80FF | 0X80FF | 0X0000 |
| 26 | START ER | 0X00000000 | 0XFFFFFFFF | 0X8041 | 0X0000 | 0X80FF | 0X80FF | 0X0000 |
| 27 |  | 0X00000000 | 0XFFFFFFFF | 0X8004 | 0X0000 | 0X80FF | 0X80FF | 0X0000 |
| 28 |  | 0X00000000 | 0XFFFFFFFF | 0X80FF | 0X0000 | 0X80FF | 0X0900 | 0X0000 |
| 29 |  | 0X00000000 | 0XFFFFFFFF | 0X80FF | 0X0000 | 0X80FF | 0X0900 | 0X0000 |
| 30 | END ER; SEND COMPLETION TO MC | 0X00000000 | 0XFFFFFFFF | 0X80FF | 0X0000 | 0X80FF | 0X80FF | 0X0000 |
| 31 | BEGIN BC | 0X00000000 | 0XFFFFFFFF | 0X0000 | 0X0000 | 0X0000 | 0X0000 | 0X0000 |
| 32 |  | 0X00000000 | 0XFFFFFFFF | 0X0000 | 0X0000 | 0X0000 | 0X0000 | 0X0000 |
| 33 | END BC | 0X00000000 | 0XFFFFFFFF | 0X0000 | 0X0000 | 0X0000 | 0X0000 | 0X0000 |
| 34 | BEGIN CR; RUN INFEED CONVEYOR IN REVERSE | 0X00000000 | 0XFFFFFFFF | 0X80FF | 0X0000 | 0X0100 | 0X80FF | 0X0000 |
| 35 | HOME SAMPLE CARRIER WHILE DISCHARGE RUNS | 0X00000000 | 0XFFFFFFFF | 0X80FD | 0X80FD | 0X80FF | 0X0900 | 0X0000 |
| 36 | MOVE SAMPLE LEVER TO EJECT POSITION | 0X00000000 | 0XFFFFFFFF | 0X8044 | 0X0000 | 0X80FF | 0X0900 | 0X0000 |
| 37 | HOME SAMPLE LEVER | 0X00000000 | 0XFFFFFFFF | 0X80FD | 0X0000 | 0X80FF | 0X0000 | 0X0000 |

FIG. 11A2

| SENSEL | STST | SMSK | MTST | SMTST | TOSM | TVAL | TFNC | ENDCTL | BRNCTL | DEST |
|---|---|---|---|---|---|---|---|---|---|---|
| 0X0000 | 0X00 | 0X00 | 0X00 | 0X0000 | 0XFF | 0X0000 | 0X00 | 0x0000 | 0x0000 | 0x0000 |
| 0X0000 | 0X00 | 0X00 | 0XFF | 0X0000 | 0 | 0X0000 | 0X00 | 0x0007 | 0x0000 | 0x0000 |
| 0X0000 | 0X00 | 0X00 | 0XFF | 0X0000 | 0 | 0X0000 | 0X00 | 0x0007 | 0x0000 | 0x0000 |
| 0X0000 | 0X00 | 0X00 | 0XFF | 0X0000 | 0 | 0X0000 | 0X00 | 0x0007 | 0x0000 | 0x0000 |
| 0X0000 | 0X00 | 0X00 | 0XFF | 0X0000 | 0 | 0X0000 | 0X00 | 0x0007 | 0x0000 | 0x0000 |
| 0x0030 | 0x04 | 0x04 | 0xFF | 0X0000 | 0 | 0X000A | 0X42 | 0X0000 | 0x0101 | 12 |
| 0X0230 | 0X00 | 0x04 | 0XFF | 0X0000 | 0 | 0X0000 | 0X00 | 0X0001 | 0x0101 | 12 |
| 0X0030 | 0X00 | 0X04 | 0XFF | 0X0000 | 0 | 0X0000 | 0X00 | 0X0001 | 0X0000 | 0x0000 |
| 0X0000 | 0X00 | 0X00 | 0XFF | 0X0000 | 0 | 0X000B | 0X42 | 0X0000 | 0X0000 | 0X0000 |
| 0X0000 | 0X00 | 0X00 | 0XFF | 0X0000 | 0 | 0X000C | 0X42 | 0x0000 | 0X0000 | 0X0000 |
| 0X0030 | 0X04 | 0X04 | 0XFF | 0X0000 | 0 | 0X0000 | 0X00 | 0X0006 | 0X0001 | 5 |
| 0X0040 | 0X1F | 0X1F | 0XFF | 0X0000 | 0 | 0X000D | 0X42 | 0x0001 | 0X0000 | 0X0000 |
| 0X0040 | 0X1F | 0X1F | 0X00 | 0X0000 | 0 | 0X000E | 0x43 | 0x0007 | 0X0000 | 17 |
| 0x0040 | 0X00 | 0x1F | 0X00 | 0X0000 | 0 | 0X000F | 0x42 | 0x0006 | 0X0000 | 0x0000 |
| 0X0230 | 0X01 | 0X01 | 0XFF | 0X0000 | 0 | 0x0000 | 0x00 | 0x0006 | 0x0001 | 17 |
| 0X0000 | 0X00 | 0X00 | 0XFF | 0X0000 | 0 | 0X0000 | 0X00 | 0x0007 | 0x0000 | 0x0000 |
| 0X0000 | 0x00 | 0x00 | 0x00 | 0X0000 | 0x31 | 0X0010 | 0X43 | 0x0000 | 0x0101 | 18 |
| 0X0000 | 0X00 | 0X00 | 0XFF | 0X0000 | 0x39 | 0X0011 | 0X42 | 0x0101 | 0X0000 | 0X0000 |
| 0X0000 | 0X00 | 0X00 | 0XFF | 0X0000 | 0 | 0X0000 | 0X00 | 0x0000 | 0X0000 | 0X0000 |
| 0X0000 | 0X00 | 0X00 | 0XFF | 0X0000 | 0 | 0X0000 | 0X00 | 0x0007 | 0X0000 | 0x0000 |
| 0xE000 | 0X00 | 0X1F | 0X00 | 0X0000 | 0 | 0X0000 | 0X00 | 0x0007 | 0X0000 | 0x0000 |
| 0X0000 | 0X00 | 0X00 | 0X00 | 0X0000 | 0 | 0X0012 | 0x42 | 0x0007 | 0X0000 | 0x0000 |
| 0X10A0 | 0x05 | 0X48 | 0X00 | 0X0000 | 0 | 0x0000 | 0X00 | 0x0202 | 0x0001 | 24 |
| 0x0000 | 0X00 | 0x00 | 0X00 | 0X0000 | 0 | 0x0000 | 0X00 | 0x0007 | 0x0202 | 25 |
| 0X4000 | 0X00 | 0X1F | 0X00 | 0X0000 | 0 | 0X0000 | 0X00 | 0x0007 | 0X0000 | 0x0000 |
| 0X0000 | 0X00 | 0X00 | 0XFF | 0X0000 | 0X32 | 0X0000 | 0X00 | 0x0007 | 0X0000 | 0x0000 |
| 0X0000 | 0X00 | 0X00 | 0XFF | 0X0000 | 0 | 0X0000 | 0X00 | 0x0007 | 0X0000 | 0x0000 |
| 0X0000 | 0X00 | 0X00 | 0XFF | 0X0000 | 0 | 0X0000 | 0X00 | 0x0007 | 0X0000 | 0x0000 |
| 0X0230 | 0X02 | 0X02 | 0X00 | 0X0000 | 0 | 0X0013 | 0x43 | 0x0007 | 0X0000 | 30 |
| 0X0000 | 0X00 | 0X00 | 0X00 | 0X0000 | 0 | 0X0014 | 0x42 | 0x0007 | 0X0000 | 0x0000 |
| 0X0000 | 0X00 | 0X00 | 0XFF | 0X0000 | 0X33 | 0X0000 | 0X00 | 0x0007 | 0X0000 | 0x0000 |
| 0X4000 | 0X00 | 0X1F | 0X00 | 0X0000 | 0 | 0X0000 | 0X00 | 0x0007 | 0X0000 | 0x0000 |
| 0X0000 | 0X00 | 0X00 | 0X00 | 0X0000 | 0x44 | 0X0015 | 0X42 | 0x0000 | 0X0000 | 0x0000 |
| 0X0000 | 0X00 | 0X00 | 0X00 | 0X0000 | 0 | 0X0000 | 0X00 | 0x0007 | 0X0000 | 0x0000 |
| 0x0000 | 0X00 | 0x00 | 0x00 | 0X0000 | 0x30 | 0X0016 | 0X02 | 0x0007 | 0x0000 | 0x0000 |
| 0x0000 | 0X00 | 0x00 | 0xFF | 0X0000 | 0 | 0x0000 | 0x00 | 0x0007 | 0x0000 | 0x0000 |
| 0x0000 | 0X00 | 0x00 | 0xFF | 0X0000 | 0 | 0x0000 | 0x00 | 0x0007 | 0x0000 | 0x0000 |
| 0x0000 | 0X00 | 0x00 | 0xFF | 0X0000 | 0 | 0x0000 | 0x00 | 0x0007 | 0x0000 | 0x0000 |

FIG. 11B1

| STATE ORDER | STATE DESCRIPTION | DOR | DAND | SM | CM | CI | CO | RC |
|---|---|---|---|---|---|---|---|---|
| 38 | RUN CARRIER OUTPUT BUFFER MOTOR UNTIL SENSOR NOT BLOCKED OR UNTIL TIME OUT | 0X00000000 | 0XFFFFFFFF | 0X80FF | 0X0000 | 0X80FF | 0X0000 | 0x0000 |
| 39 | RUN CO A LITTLE LONGER | 0X00000000 | 0XFFFFFFFF | 0X80FF | 0X0000 | 0X80FF | 0X0000 | 0x0000 |
| 40 | END CR | 0X00000000 | 0XFFFFFFFF | 0X80FF | 0X0000 | 0X80FF | 0X80FF | 0x0000 |
| 41 | BEGIN IC (IS CLEAR); IF OUTPUT SENSOR NOT BLOCKED BRANCH TO "IS CLEAR = TRUE" | 0X00000000 | 0XFFFFFFFF | 0X80FF | 0X0000 | 0X80FF | 0X80FF | 0x0000 |
| 42 | RUN CARRIER OUTPUT BUFFER MOTOR UNTIL SENSOR NOT BLOCKED OR UNTIL TIME OUT. IF TIMEOUT BRANCH TO "IS CLEAR = FALSE" | 0X00000000 | 0XFFFFFFFF | 0X80FF | 0X0000 | 0X80FF | 0X0900 | 0x0000 |
| 43 | RUN CO A LITTLE LONGER | 0X00000000 | 0XFFFFFFFF | 0X80FF | 0X0000 | 0X80FF | 0X0900 | 0x0000 |
| 44 | IS CLEAR = TRUE; SEND 'T', BRANCH TO END IS | 0X00000000 | 0XFFFFFFFF | 0X80FF | 0X0000 | 0X80FF | 0X80FF | 0x0000 |
| 45 | IS CLEAR = FALSE; SEND 'F' | 0X00000000 | 0XFFFFFFFF | 0X80FF | 0X0000 | 0X80FF | 0X80FF | 0x0000 |
| 46 | END IS | 0X00000000 | 0XFFFFFFFF | 0X80FF | 0X0000 | 0X80FF | 0X80FF | 0x0000 |
| 47 | BEGIN WR | 0X00000000 | 0XFFFFFFFF | 0X0000 | 0X0000 | 0X0000 | 0X0000 | 0x0000 |
| 48 | | 0X00000000 | 0XFFFFFFFF | 0X0000 | 0X0000 | 0X0000 | 0X0000 | 0x0000 |
| 49 | END WR | 0X00000000 | 0XFFFFFFFF | 0X0000 | 0X0000 | 0X0000 | 0X0000 | 0x0000 |
| 50 | BEGIN ZZ | 0X00000000 | 0XFFFFFFFF | 0X0000 | 0X0000 | 0X0000 | 0X0000 | 0x0000 |
| 51 | END ZZ | 0X00000000 | 0XFFFFFFFF | 0X0000 | 0X0000 | 0X0000 | 0X0000 | 0x0000 |

| SENSEL | STST | SMSK | MTST | SMTST | TOSM | TVAL | TFNC | ENDCTL | BRNCTL | DEST |
|---|---|---|---|---|---|---|---|---|---|---|
| 0X0230 | 0X00 | 0X01 | 0X00 | 0X0000 | 0 | 0X0017 | 0X42 | 0X0001 | 0X0000 | 0X0000 |
| 0X0000 | 0X00 | 0X00 | 0X00 | 0X0000 | 0 | 0X0018 | 0X42 | 0X0007 | 0X0000 | 0X0000 |
| 0X0000 | 0X00 | 0X00 | 0X00 | 0X0000 | 0X33 | 0X0000 | 0X00 | 0X0101 | 0X0000 | 0X0000 |
| 0X0230 | 0X00 | 0X01 | 0X00 | 0X0000 | 0X30 | 0X0000 | 0X00 | 0X0101 | 0X0001 | 44 |
| 0X0230 | 0X00 | 0X01 | 0X00 | 0X0000 | 0 | 0X0019 | 0X43 | 0X0001 | 0X0000 | 45 |
| 0X0000 | 0X00 | 0X00 | 0X00 | 0X0000 | 0 | 0X001A | 0X42 | 0X0007 | 0X0000 | 0X0000 |
| 0X0000 | 0X00 | 0X00 | 0X00 | 0X0000 | 0X54 | 0X0000 | 0X00 | 0X0000 | 0X0101 | 46 |
| 0X0000 | 0X00 | 0X00 | 0X00 | 0X0000 | 0X46 | 0X0000 | 0X00 | 0X0101 | 0X0000 | 0X0000 |
| 0X0000 | 0X00 | 0X00 | 0X00 | 0X0000 |  | 0X0000 | 0X00 | 0X0101 | 0X0000 | 0X0000 |
| 0X0030 | 0X04 | 0X04 | 0XFF | 0X0000 | 0 | 0X0000 | 0X00 | 0X0001 | 0X0000 | 0X0000 |
| 0X0000 | 0X00 | 0X00 | 0XFF | 0X0000 | 0X52 | 0X001B | 0X42 | 0X0000 | 0X0000 | 0X0000 |
| 0X0000 | 0X00 | 0X00 | 0XFF | 0X0000 | 0 | 0X0000 | 0X00 | 0X0000 | 0X0000 | 0X0000 |
| 0X0000 | 0X00 | 0X00 | 0X00 | 0X0000 | 0XFF | 0X0000 | 0X00 | 0X0000 | 0X0080 | 0X0000 |
| 0X0000 | 0X00 | 0X00 | 0X00 | 0X0000 | 0XFF | 0X0000 | 0X00 | 0X0000 | 0X0000 | 0X0000 |

MULTI-LEVEL CONTROLLER SYSTEM

RELATED APPLICATIONS

This application claims the benefit, under 35 USC § 119(e), of U.S. Provisional Application No. 60/427,445 and U.S. Provisional Application No. 60/427,527 file date Nov. 18, 2002, which are incorporated by reference herein.

FIELD OF THE INVENTION

The present invention relates generally to a state machine architecture and more specifically to a method and system for analyzing particles in a dilute fluid sample.

BACKGROUND OF THE INVENTION

Most processes consist of several process segments that fit together in a physically and temporally consistent manner. For example, a fluid control and imaging system, such as a urinalysis system, includes process segments for receiving a sample, aspirating the sample, and injecting the sample into a fluidics system where images are taken as the sample flows in a proper manner. To produce meaningful data, the sample receptacle, the aspirator, the valves, the pumps, and the optical components have to be in the proper positions at the proper times, and various fluids have to be released at the right time. Typically, these process segments are controlled on a real time basis by a single processor according to instructions in software or firmware. The instructions usually entail responding to various inputs by considering "hard-coded" branching conditions. This type of "hard-coded" branching takes the form of a "case statement" in which each case corresponds to a state and a relatively complicated "if" statement determines the response to inputs when in the given state.

In this type of real time operation, the process segments do not all happen completely simultaneously. For example, although the sample may be received and aspirated at the same time the flow cell is being flushed with a cleaning solution, the aspiration and the flushing take different lengths of time to complete, and therefore do not start and end at the same time. Furthermore, how long each of these processes will take to complete cannot always be predicted accurately because a process may have a random component (e.g., sample concentration will determine the time required to capture a fixed number of images) or a catastrophic unplanned event, such as the aspiration needle getting stuck or the cleansing fluid not being loaded correctly. Since the success of a process depends on each process segment running smoothly, this type of catastrophic unplanned event not only disrupts a process segment but also turns an entire process run into wasted effort if the event is not handled properly. Further, there is extra inefficiency associated with troubleshooting once it is determined that a run was erroneous because it is difficult to know exactly which process segment was in progress at a certain point in time.

In addition to the above disadvantages with a single-processor hard-coded real time controller, there is an additional source of inefficiency stemming from the need for a process engineer to collaborate with a software engineer to adjust the process parameters. While the process engineer understands the process and knows how the components ought to be set, implementation of the process usually requires a software engineer. Thus, typically, the process engineer has to explain the process and what he wants to accomplish to a programmer, who then revises the code. This process engineer—software engineer communication link not only takes time but also creates more opportunities for error based on miscommunication or misunderstanding.

For the above reasons, a method of controlling a process more efficiently is desired.

SUMMARY OF THE INVENTION

The invention is a system (e.g., a urinalysis system) that includes multiple levels of controllers. The system includes a first control level having at least one level-1 controller that moves through a sequence of first level states, the first control level generating a first level command that is associated with one of the first level states. The system also includes a second control level having at least one level-2 controller that moves through a sequence of second level states in response to the first level command. The level-2 controller sends a status report to the first control level when a level-2 condition that is defined in one of the second level states is fulfilled in the second level states.

The invention also includes a method of executing a process. The method entails identifying a sequence of first level states to be executed, issuing a first level command to a second level that has a level-2 controller, wherein the first level command is associated with one of the first level states, and receiving a second level status report from the level-2 controller. The status report indicates a status of the level-2 controller in response to the first level command.

In another aspect, the invention includes a method of controlling a system that includes controllers and system components. The method entails receiving input parameters in a first language that is not readable by the controllers, wherein the input parameters are instructions for controlling system components, converting the input parameters into translated parameters that are in a second language, wherein the second language is readable by the controllers, and creating a table containing the input parameters and corresponding translated parameters. The input parameters are editable in the table.

In yet another aspect, the invention is a system including a controller, system components, and a process for generating a table that is useful for controlling the controller and the system components. The table has a first set of columns containing instructions in a first language that is not readable by the controller, and a second set of columns containing instructions in a second language that is readable by the controller. The values and instructions in the second set of columns are translated versions of the instructions in the first set of columns.

In another aspect, the invention is a system comprising a level-1 controller that divides a level-1 task into a first level-2 task and a second level-2 task and issues a first level command to a first level-2 controller and a second level-2 controller, respectively, wherein the first level-2 controller executes the first level-2 task and the second level-2 controller executes the second level-2 task in response to the first level command, so that when the first and the second level-2 controllers complete their level-2 tasks, the level-1 controller completes the level-1 task.

The invention is also a multi-layered control system that includes a plurality of controllers in different control levels. Each controller behaves according to a controller table containing a unique set of values. Although the controller tables contain different values, the tables have substantially similar formats. Each controller table is indexed by states and has a first column of commands to issue to a lower level controller, a second column of status reports to send to a higher level controller, a third column of tests for checking whether a predefined condition is fulfilled, and a fourth column defining a course of action if the predefined condition is fulfilled. An interface control level receives commands from the plurality of controllers and controls system components in response to the commands.

BRIEF DESCRIPTION OF THE DRAWINGS AND APPENDICES

Figure 1:
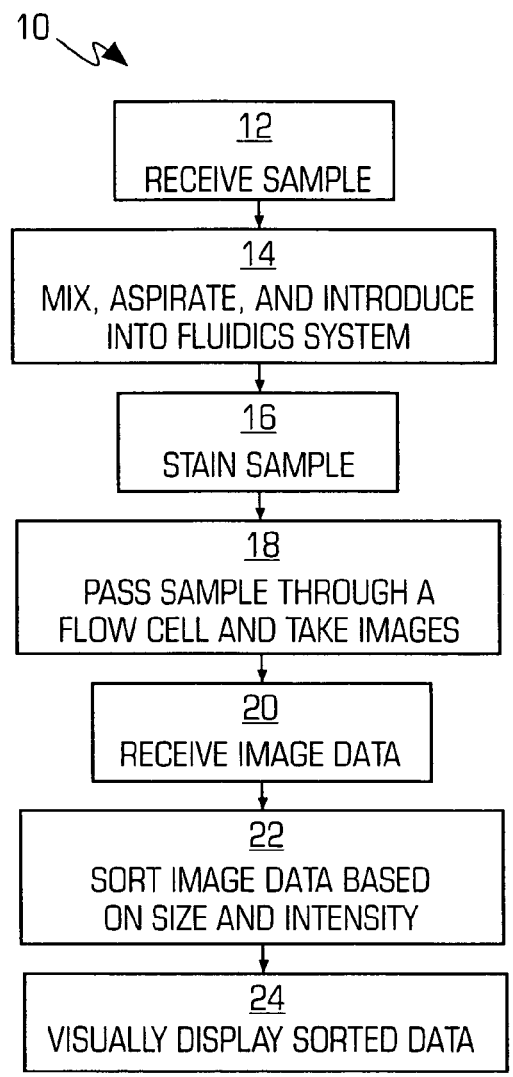
FIG. 1 is a flow chart of an exemplary urinalysis process that may be used with the invention.

FIG. 6 provides an exemplary set of run sequences that the host controller sends to the level-1 controller;

FIG. 7 demonstrates how the level-1 controller executes a run sequence once an activating signal is received from the host controller;

FIGS. 8A-8L (collectively "FIG. 8") depict exemplary tables that may be used for a level-1 controller in a urinalysis process; and FIGS. 9A-9C ("FIG. 9"), 10A and 10B (FIG. 10), and 11A and 11B ("FIG. 11") depict exemplary tables that may be used for level-2 controllers in a urinalysis process.

DETAILED DESCRIPTION OF THE PREFERRED EMBODIMENTS

The invention is particularly applicable to urinalysis processes and it is in this context that the invention will be described. It will be appreciated, however, that the system and method in accordance with the invention has greater utility since the system and method may be used with other types of processes that can be modeled as one or more state machines. The present invention may be incorporated into an in-vitro urinalysis diagnostic device that utilizes the technologies disclosed in U.S. Pat. Nos. 4,338,024 and 4,393,466.

Generally, there are two types of state machines: synchronous state machines and asynchronous state machines. Synchronous state machines carry out segments of a process (or a time-slice of a process) synchronized to the beat of a clock. Thus, if a process were to be divided into a series of one-minute time slices, the pre-assigned tasks for each of those time slices are triggered at each clock signal. An advantage of a synchronous state machine is its stability, which stems from everything being synchronized to the clock. However, this synchronization can be a limitation of a synchronous state machine because synchronization often does not result in the fastest process runs. Furthermore, choosing the right clock speed can be tricky, for some parts of the process might want a faster clock speed than other parts. If the clock speed is too slow, certain events that start and finish between consecutive clock signals can get missed.

Asynchronous state machines provide a faster solution than the synchronous state machines. Asynchronous state machines, which do not operate to the beat of a clock, usually consist of a block of logic elements whose output is fed back as an input through a delay line. Thus, the output and next state of an asynchronous state machine is determined from a combination of the current state and the current input. The fact that the next state is immediately determined once the current state value transits the delay line allows the process to be run fast if the delay is shortened. However, these asynchronous state machines are not without a disadvantage. Since every change in the input test condition is immediately reflected at the output of the combinatorial logic and starts a new state propagating through the delay element, the asynchronous state machines can be unstable. Background information and details about asynchronous and synchronous state machines may be found in Tinder, Richard F., *Engineering Digital Design* (Academic Press, January 2000).

The invention offers a hybrid-type state machine that has the stability of the synchronous state machine and the speed of the asynchronous state machine but does not suffer the disadvantages of either. This hybrid-type state machine is implemented in the form of a multi-level controller system wherein one or more controllers may be present in each level. If there are multiple controllers in one level, the controllers in the same level behave independently of each other. The behavior of each controller is dictated by a state record formalism, which may be implemented in a spreadsheet/table. The spreadsheet has multiple fields, with each row being a "state record." Some fields test certain conditions, and the "next state" is identified based on the test result. The controller then transitions to the next state and carries out the values/commands of the fields in this next state.

Each controller in the multi-level controller system behaves according to its own spreadsheet. For example, for a system that includes one controller at the first control level and three controllers at the second control level, there would be four spreadsheets. The controller at the first control level issues commands to the three controllers at the second control level, the three controllers execute their tasks according to the commands, and send at least one signal back to the controller at the first control level when their tasks are complete. Although the three controllers do not necessarily finish their tasks at the same time, the controller at the first control level waits to hear back from all three controllers (or however many it needs to hear back from) before moving on to the next state in the spreadsheet for the first control level. Thus, while the three controllers at the second control level execute their tasks independently of each other, the controller at the first control level synchronizes the states to a degree by waiting to hear back from the three controllers before proceeding to the next state.

This hybrid-type state machine is like a synchronous state machine in that the controller at the first control level moves from a current state to a next state when a predetermined set of tasks are accomplished or conditions are met. However, this hybrid-type state machine is not restricted to the beat of a clock like a synchronous state machine. Rather, it can execute a process as fast as its components can execute their discrete tasks. By using faster processors, the hybrid-type state machine can be made to execute a process almost as fast as an asynchronous state machine.

The hybrid-type state machine also has characteristics of an asynchronous state machine. For example, it tests conditions to decide the next step, and as soon as these conditions are met it advances to the next state. However, it does not suffer the instability problem like an asynchronous state machine because the first level synchronizes the process segments at certain points in the process (i.e., at the end of each state), and because of the state record formalism all possible states and state transitions are specified. The state record formalism that is implemented in a spreadsheet with fields specifies all the parameters so that certain points of the process are synchronized.

Another advantage of this multi-level controller architecture is that the syntax at every level except the lowest level can be made the same, drastically simplifying the programming process. At each level in this multi-level controller system, the controller only "knows" and cares about what is in its spreadsheet; it does not know about all the details happening at the levels above or below its own level. For example, a three-leveled system may include 1) a high control level that executes run sequences, and 2) a middle control level that executes the states in each of the run sequences and issues commands to 3) a low control level that controls motors, actuators, and valves according to commands in the states. In this system, the high control level only knows to send a run sequence command to the middle control level, and to move to the next run sequence state once it hears back from all the controllers in the middle control level that it needs to hear back from. The high control level is unaware of all the details of the states in the middle control level, the existence of low control levels below the middle level, the function of the low control level and each of the valves and the motors, etc. Likewise, the middle control level only knows to send out certain commands to the low control level in response to a command from the high control level, and to determine the next state when it hears back from the low control level.

A benefit of using the spreadsheet is that if a process engineer's terminology (e.g., motor #2 on/off, test sensor #12, valve #3 on/off) is used in the fields of the spreadsheet, the process engineer can adjust the settings of a process run without getting help from a programmer. By inputting values into the fields of the spreadsheet(s), the process engineer can specify states and run sequences for each level by himself. The spreadsheet allows the process to be broken down into process engineering terminology by receiving the input parameters from the process engineer in the language of his preference, and converting these input parameters into a machine-usable code. The converted code may be resented in a section of the spreadsheet, such as a separate set of column(s).

As used herein, a "state" refers to a process segment that is associated with the controllers and the components of the system being in a certain position/setting or performing a specific task. The "task" can be instructions to do something active, such as opening a valve, or instructions to do something passive, like waiting. A row in the spreadsheets of FIGS. 8, 9, 10, and 11, for example, represents a state. A "state record" is a collection of the field values or parameters in a row of the spreadsheets in FIGS. 8, 9, 10, and 11. "Parameters" refer to values in a table. A state may be indexed by a "state index" or a "state order." The fields in a state record represent/specify the outputs from the controller when in the given state, along with the tests and conditions that these tests must satisfy to end the state. For example, if a level-1 controller is to issue first level commands to three controllers at a second control level, the level-1 controller will obtain the specific command for each of these level-2 controllers from the respective fields in its state record. These first level commands may identify the run sequence to be executed by each level-2 controller. In this case, each level-2 controller executes the second level states in the identified run sequence. As used herein, controllers in the first control level are referred to as "level-1 controllers," controllers in the second control level are referred to as "level-2 controllers," etc. Also, as used herein, "first level commands" refer to commands issued by a level-1 controller, "second level commands" refer to commands issued by a level-2 controller, etc. "Execution" of states means to move through the states in an appropriate order, taking appropriate actions in each state.

Multiple states make up a "run sequence." Typically, a run sequence has a specific set of states arranged in a specific order to achieve a specified function, such as sample aspiration or moving a specimen rack from point A to point B. Often, multiple state run sequences at the second control level corresponds to a single state in the first control level.

"Motors," as used herein, includes both motors that actually move mechanical parts and motors that drive pumps, etc. "Components," as used herein, refer to all physical portions of a system other than a controller. "Commands" are signals traveling from a controller at a higher level to a controller at a lower level, and "status reports" are signals traveling from a controller at a lower level to a controller at a higher level.

Now, the invention will be further described in reference to the Figures.

FIG. 1 is a flow chart of an exemplary urinalysis process 10 that may be implemented with the invention. The analysis process 10 begins when a urine sample is received (stage 12) by a sampling system. The received sample is mixed and aspirated into the system and introduced into a fluidics system (step 14). Elements in the flow microscope stain and mix the sample (step 16), then pass it through a flow cell (step 18) where images are taken. A host controller oversees the taking of the images. An imaging computer receives the data from the flow cell (step 20), processes them as needed (step 22), and displays the data (step 24).

Figure 2:
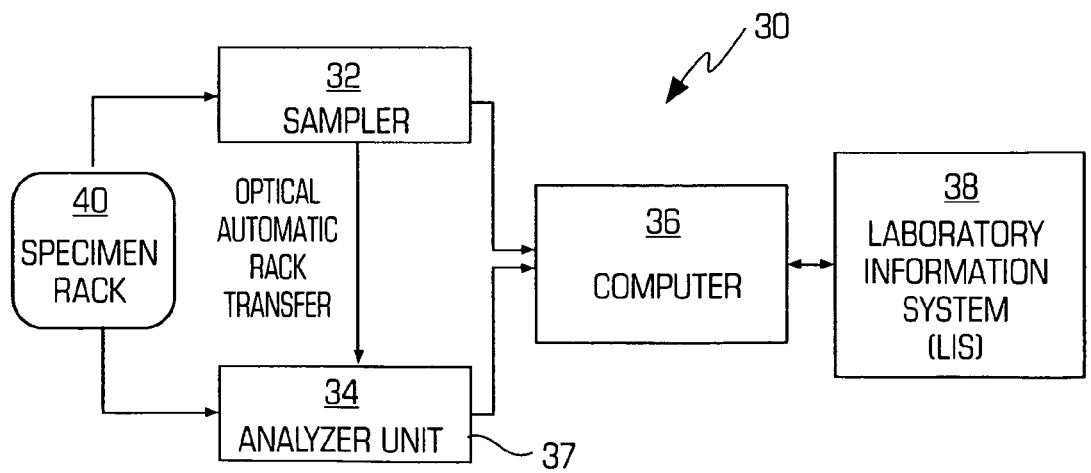
FIG. 2 is a block diagram showing the main components of an exemplary urinalysis system.

FIG. 2 is a block diagram showing the main components of an exemplary urinalysis system 30. The urinalysis system 30 includes a sampler 32 and a microscopy analyzer unit 34, both of which feed information to a computer 36. A communication link 37 connects the microscopy analyzer unit 34 to the computer 36, which is also connected to a Laboratory Information System (LIS) 38. A specimen rack 40 that carries test tubes of samples travels between the sampler 32 and the microscopy analyzer unit 34. In some embodiments, an automatic rack transfer mechanism transfers the specimen rack 40 from the sampler 32 to the microscopy analyzer unit 34. In other embodiments, the transfer is done manually.

Figure 3:
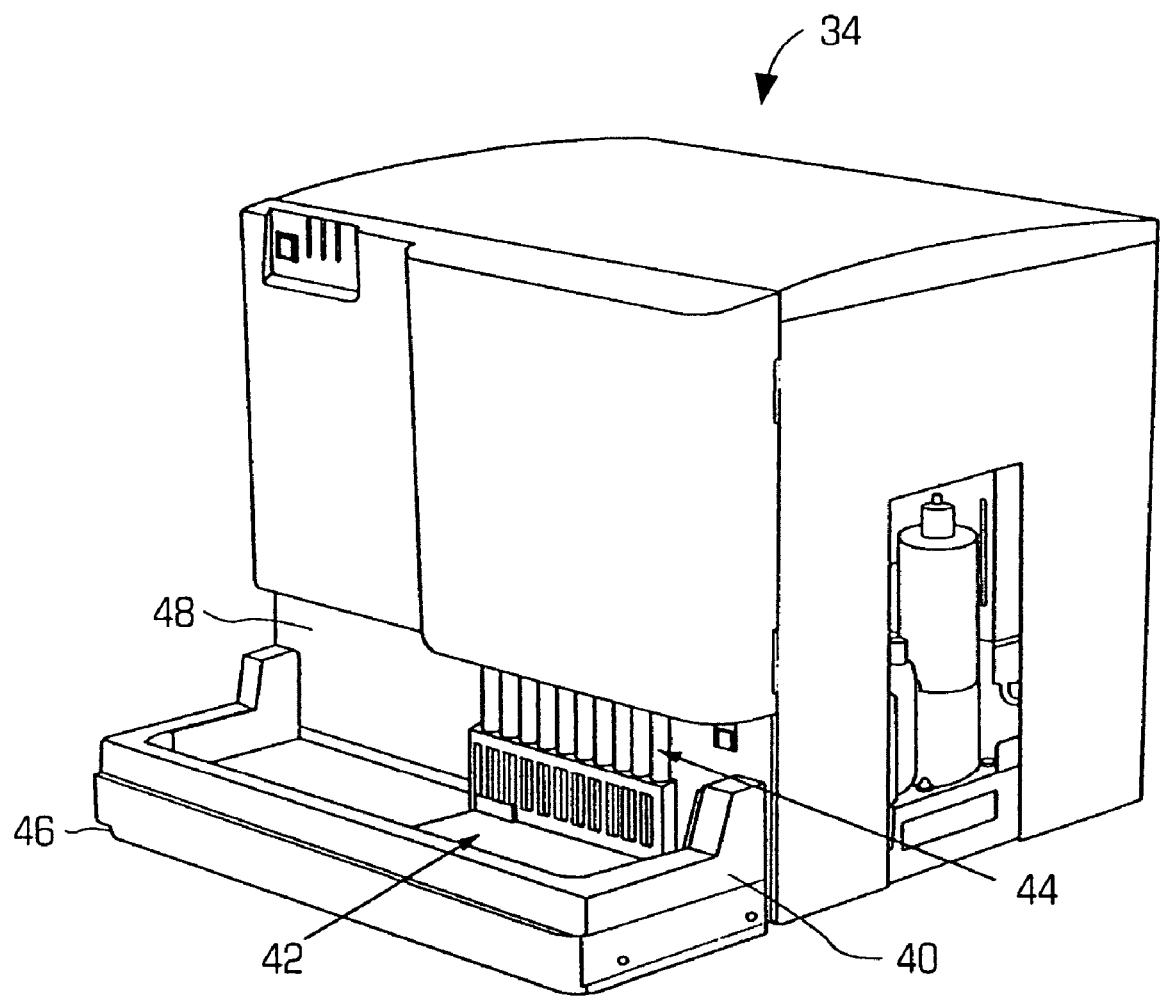
FIG. 3 is a perspective view of an exemplary bench top module analyzer unit that may be used for the invention.

FIG. 3 is a perspective view of an exemplary bench top module microscopy analyzer unit 34 that may be used for the invention. The microscopy analyzer unit 34 aspirates samples, collects images from urine samples using digital image capture of analyte images presented in a flow microscope, and performs image processing to isolate individual particles. The microscopy analyzer unit 34 has its own power supply, processor, and controllers, a barcode reader to identify samples, motors to drive the mechanical components of the system, fluidics systems to pipette samples from the test tubes, and a communication link 37 to the computer 36 (see FIG. 2). On the outside, the microscopy analyzer unit 34 includes a platform 42 onto which the specimen rack 40 is placed, and some buttons, e.g., a start button 44. The specimen rack 40 is loaded on a measurement side 44 of the platform 42. Multiple (e.g., five) racks may be loaded at the same time. An input conveyor (CI) moves the rack away from the user and toward a wall 48, where the samples are aspirated by a pipette system (not shown). As each sample is aspirated, a shifter arm incrementally moves the rack toward a return side 46, placing the next sample test tube under the pipette. When all the test tubes are sampled, an output conveyor (CO) near the return side 46 moves the rack forward, away from the wall 48. Where multiple racks are placed on the platform 42, the rack that was at the very back (i.e., near the wall 48) on the measurement side 44 will end up at the front (i.e., away from the wall 48) on the return side.

Figure 4A:
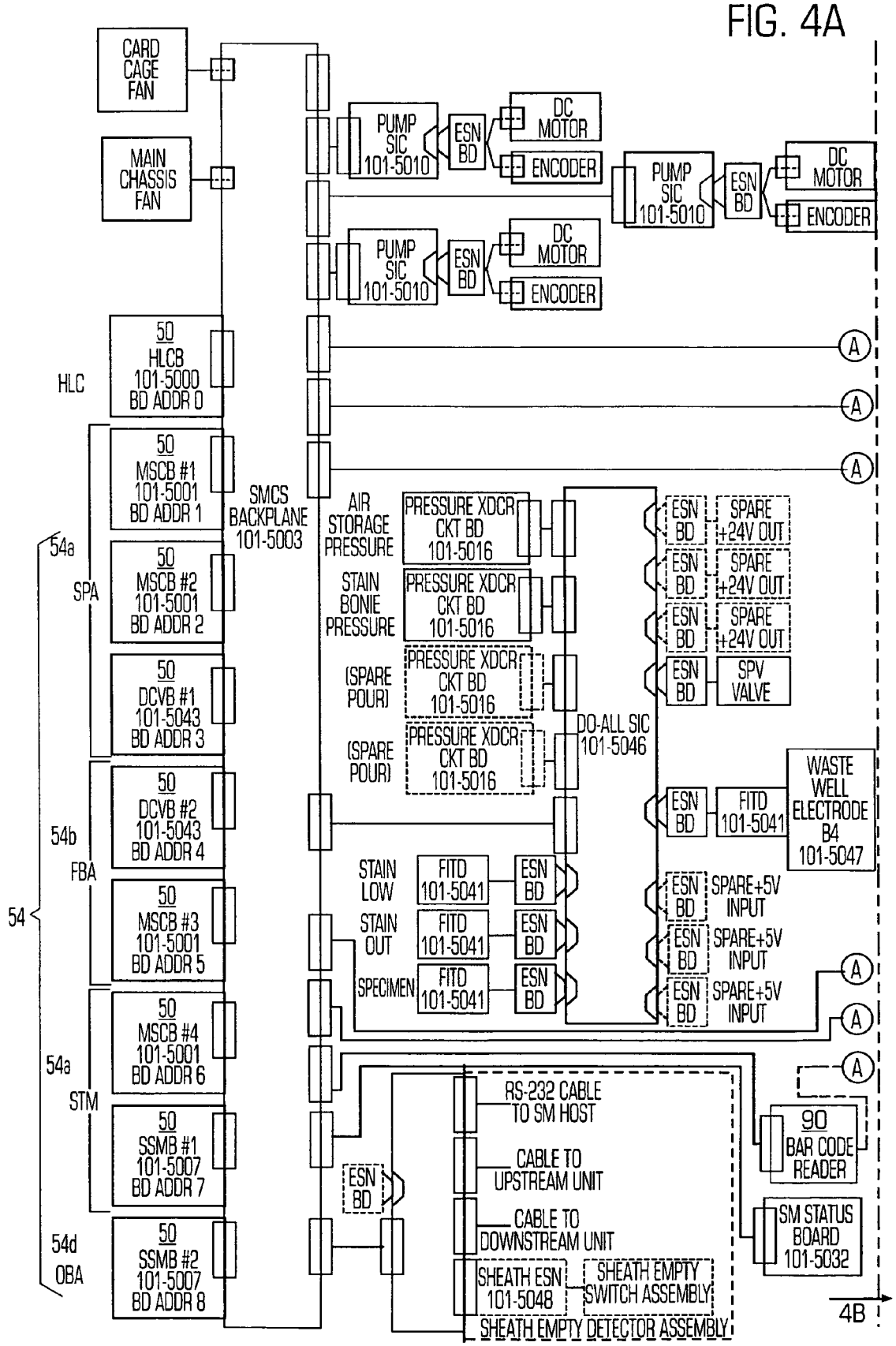
FIG. 4 is a schematic diagram of the analyzer unit.
Figure 4B:
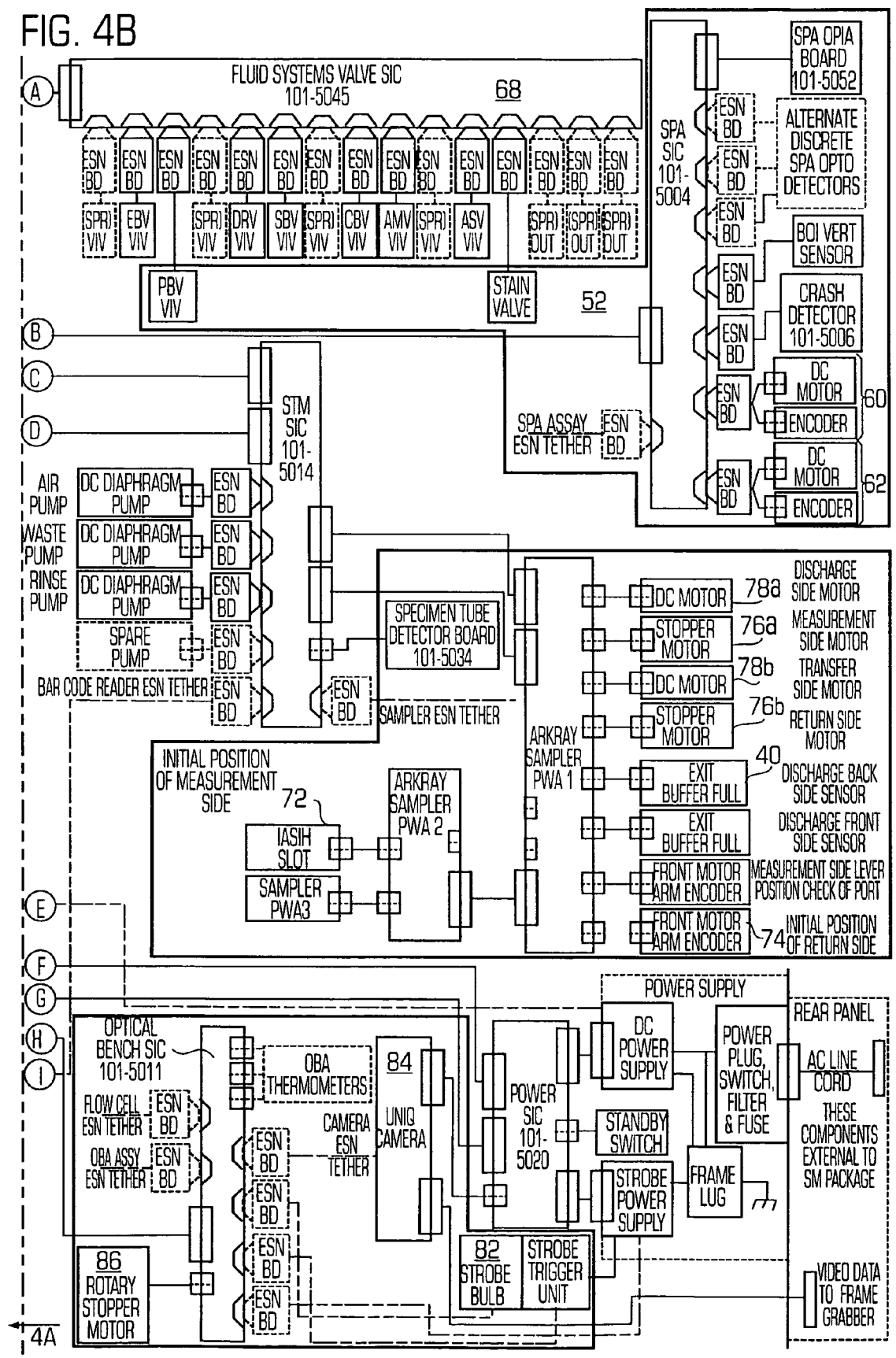

FIG. 4 is a schematic diagram of the microscopy analyzer unit 34. The nine connectors 50 along the left hand side of the figure are connected to a level-1 controller 52 (HLC) and a level-2 controller 54 that is controlled by the level-1 controller. In the embodiment shown in FIG. 4, the level-2 controller includes a first level-2 controller 54a (also called the specimen presentation assembly (SPA) controller), a second level-2 controller 54b (also called the fluid block assembly (FBA) controller), a third level-2 controller 54c (also called the specimen transport mechanism (STM) controller), and a fourth level-2 controller 54d (also called the optical Block Assembly (OBA) controller). Each of the level-2 controllers controls certain system components.

The first level-2 controller 54a controls the aspirator process by sending signals to pipette motors 60, 62, an evacuation pump 64, a sheath pump 67, and some of the valves 68. A pipetting station controlled by the first level-2 controller 54a is located near the front of the microscopy analyzer unit 34. The pipetter, controlled by the pipette motors 60, 62, mixes the sample and aspirates a predetermined amount of the sample. The sample is mixed in its tube, a sampling probe descends to the tube bottom and expels a pulse of air to assure uniform mixing of sediment before being processed by the microscopy analyzer unit 34. After the mixing, the sample is drawn by vacuum into a flowcell through a series of tubes that allow stain to be introduced into and mixed with the urine.

The second level-2 controller 54b controls the flow cell by sending signals to a cannula pump 70, the sheath pump 67, and some of the valves 68. In the particular embodiment, the valves 68 are controlled by both the first and the second level-2 controllers 54a and 54b. The fluidics components are composed of a stain container (not shown), a sheath container (not shown), and three pumps 64, 67, and 70 that aspirate and circulate the sample, the stain, sheath fluid, and a cleaner (e.g., IRISolv) into the fluid block and the flow cell. The pumps 64, 67, and 70 may be peristaltic pumps or displacement pumps.

The third level-2 controller 54c sends signals to components that function to transport the specimen rack 40, by sending signals to various arms that move the rack along a path. More specifically, the third level-2 controller 54c sends signals to a front arm stepper motor 76a, a rear arm stepper motor 76b, one or more DC motors 78, to move the specimen rack 40. Sampling from the tubes on the sample platform 42 (shown in FIG. 3) is performed by a pump-driven fluidic subsystem. Any suitable pump, including a displacement pump of the type described in U.S. Pat. No. 7,150,607, may be used to drive the sampling process.

The third level-2 controller 54c interfaces a barcode reader 90. The barcode reader 90 scans the barcode label on a sample tube and keeps the identification information stored locally. Eventually, the barcode reader 90 sends the scanned identification information to the Laboratory Information System (LIS) 38 via the computer 36.

The fourth level-2 controller 58 controls the optical components of the flow microscope, which may include motorized positioners 86 within a microscope (not shown) to adjust the position of a flow cell. In the embodiments in which the microscopy analyzer unit 34 utilizes the strobe illumination, the strobe flashes at a high speed, synchronized with the CCD camera 84. The CCD camera 84, which is controlled by the host controller, captures the image during the strobe flash. The level-1 controller indirectly controls the strobe bulb 82. The microscope typically includes components such as diffusion filters, lenses, and other optical elements to focus the light in a desired manner. In the embodiment shown, some of these components are controlled by the fourth level-2 controller 54d.

After the images are taken, the waste pump 94 discards the fluids into a waste line that leads to the waste chamber. A waste well liquid level sensor assembly 73 detects the liquid level in the waste chamber.

Figure 5:
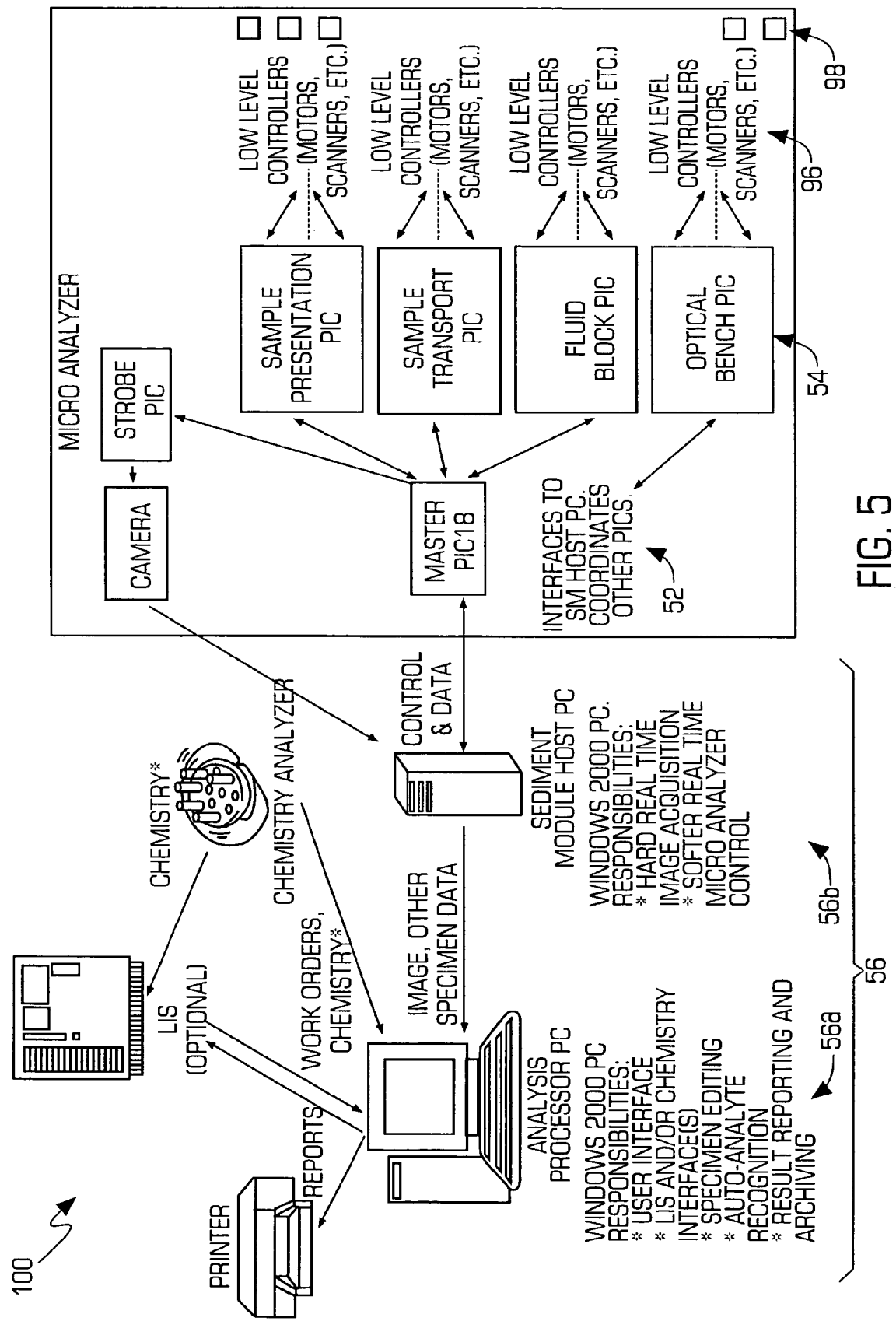
FIG. 5 is a schematic presentation of the leveled system architecture in accordance with the invention.

FIG. 5 is a schematic presentation of the leveled system architecture 100 in accordance with the invention. Unlike in a conventional system, which executes real time operation using a single processor, the leveled system architecture 100 includes multiple levels of processors and/or controllers that control each other and ultimately the system components. For example, the host level controller 56 includes a host processor, the level-1 controller controller 52 includes the master controller, the level-2 controller 54 includes four controllers 54a, 54b, 54c, and 54d, and the level-3 controller includes one or more controllers that interface between the level-2 controllers and the system components. The motors, pumps, and the valves are controlled by the level-3 controllers, which are programmed in C and typically are not changeable like the state records, which a process engineer accesses to control the operations of the second and the level-2 controllers 52, 54.

In the embodiment shown, the host level controller 56 includes an Analysis Processor (AP) 56a and a Sediment Module Host (SMH) 56b. The SMH 56b directly controls the level-1 controller 52. The user interface, however, is implemented in the AP 56a. Thus, from the user's perspective, there are two paths for controlling the system: 1) push buttons on the microscopy analyzer unit 34 (see FIG. 3), or 2) enter commands using the user interface (e.g., a GUI) in the AP 56a. The two paths allow the user to control different aspects of the system. The invention is not limited to the particular configuration of the host level controller 56 shown in FIG. 5.

In this multi-level system architecture 100, the "higher" levels send commands to the "lower levels," which perform certain functions according to the commands and return at least one status report to the "higher" levels that issued the commands. For example, the level-1 controller 56 sends first level commands to the level-2 controller 52, and the level-2 controller 52 sends second level commands to the level-3 controller 54 in accordance with the first level commands from the level-1 controller 56. The level-3 controller 54 performs its functions according to the second level commands from the level-2 controller 52, and returns a status report to the level-2 controller 52 when the functions are completed. The level-2 controller 52 waits to receive all the status reports it expects to receive and, when this happens, sends a status report to the level-1 controller 56 to inform the level-1 controller that the level-2 controller 52 completed its functions. "Completion," as used herein, can mean either a successful completion of the prescribed task(s) or a passage of a prescribed amount of time.

This leveled system architecture 100 may be used with the urinalysis process 10 described above, although its utility is not so limited. Although not shown in FIGS. 8, 9, 10, and 11, each of the spreadsheets contains a column with a header file generated by the spreadsheet for programming the controller. The header file usually takes the form of a hexadecimal file containing the state record information, and becomes loaded into an EEPROM associated with each of the microcontrollers that implement the level-1 controllers 52 and the level-2 controllers 54. In this way, the process engineer, who does not have to be a programmer, can input field values into the spreadsheet(s), which will automatically generate the code interpreted by the controllers. By entering or modifying values in the spreadsheets for the level-1 controller 52 and the level-2 controller 54, the process engineer can modify the process parameters without relying on a programmer.

FIG. 6 provides an exemplary set of run sequences that the host controller 56 sends to the level-1 controller 52. In the embodiment shown, each run sequence is identified by a two-letter code $L_1L_2$ 600. For each run sequence, there is a beginning state 602, an end state 604, and a general description 606 of what is done in the particular run sequence. For example, in run sequence RH, which is carried out in states 1 through 14, the level-2 controllers 54 are reset. In run sequence 16, which is carried out in states 15 through 99, the system resumes running racks. There is no limitation to the order in which the run sequences are executed, and not all the run sequences need to be executed during a process. Also, some states may be executed in multiple run sequences. For example, Run Sequence PI for "Irisolve Clean," which includes states 350-366, is part of Run Sequence WA for "wash with bleach" (states 356-392). The Sediment Module Host PC portion of the host controller 56 will send signals for Run Sequence PI or Run Sequence WA depending on what the process engineer wants done.

FIG. 7 is a state machine record interpreter that demonstrates how the level-1 controller controller 52 and each other level except the lowest level controller executes a run sequence once an activating signal is received from the host controller 56 (or the next higher level controller). Initially, upon activation, the level-1 controller 52 is reset (stage 700) and is in an idle state (stage 702). At this point, the current state is the state identified in the "beginning state" column in FIG. 6. After the functions of the first state are completed, the controller proceeds to the subsequent stage in the sequence and adjusts the state number (stage 704) so that a state that was "the next state" in the previous state is now "the current state." The controller waits for the subsequent stage to be completed (stage 706), then moves on to the next stage as shown by an arrow 708. After repeating stages 704 and 706 until there is no next state in the sequence, at which point the run sequence is completed and the level-1 controller 52 returns to the idle state in stage 702.

FIGS. 8, 9, 10, and 11 depict exemplary tables that may be used to implement the urinalysis process 10. The table in FIG. 8 is a level-1 controller state record table 300, which dictates the behavior of the level-1 controller 52. The tables in FIGS. 8, 9, and 10 are level-2 controller state record tables that dictate the behavior of the level-2 controller 54. The tables are arranged so that a state is represented by each row and a signal is represented by each column. In the tables, "SM" refers to the controller or processor at an adjacent higher level. For example, SM from the perspective of a level-1 controller 52 would be the host controller 56, and SM from the perspective of a level-2 controller 54 would be the level-1 controller 52.

FIG. 8 is an exemplary level-1 controller state record table 300. The state record table 300 is in the form of a spreadsheet with columns indicating different fields and rows indicating different states. The level-1 controller 52 moves from a current state to a next state until the run sequence has been completed. A state index 302 shows a numerical designation for a state that is described in a description column 304. For each state, there are commands 306 that the level-1 controller 52 issues to the level-2 controller 54. In response to the commands 306*a*, 306*b*, 306*c*, and 306*d*, the level-2 controllers 54*a*, 54*b*, 54*c*, and 54*d* perform certain functions and return status reports 308*a*, 308*b*, 308*c*, and 308*d* to the level-1 controller controller 52. The level-2 controllers 54 execute their functions independently and asynchronously with respect to one another. Since the level-2 controllers 54 may take different lengths of time to complete their respective functions, they will each return their respective status reports to the level-1 controller 52 at different points in time. The level-1 controller 52 does not send a command to execute the next state until all the expected status reports have been returned. There is no restriction to the number of status reports that the level-1 controller 52 needs to receive before moving on to the next state. Values in the status report fields 308 can be changed by a process engineer, and in table 300, "0X00" means no status report is needed.

In addition to the fields 306, 308 that pertain to communicating with the level-2 controllers 54, the level-1 controller state record table 300 contains field parameters pertaining to communicating with the host controller 56. SMTest 310 refers to a signal that the level-1 controller 52 receives from the host controller 56. A particular value of the SMTest 310 stands for a two-letter code, which is interpreted differently depending on the state of the level-1 controller at the time the two-letter code is received. For example, if the level-1 controller is idle at the time a particular code is received, the level-1 controller will interpret the code as a run sequence shown in FIG. 6. Thus, it will execute the run sequence after accessing the table of FIG. 6 to identify the run sequence. It also sends a signal ToSM 312 to the host controller to inform the host controller that the run sequence is in progress. Some time later, the host controller will issue another two-letter code to stop the run sequence, for example because all the necessary data have been collected. This time, since the level-1 controller is running at the time the two-letter code is received, the level-1 controller checks to see if the received two-letter code matches the value in the SMTest 310 field. If the value matches the value in the SMTest 310, the level-1 controller will end the state. The level-1 controller will then send a signal ToSM 312 to indicate that the run sequence has ended.

Tvalue 314 and Tfunc 316 together determine how long a state lasts. More specifically, Tvalue 314 indicates a time frame in some predetermined temporal unit and Tfunc 316 indicates how the time frame indicated in the Tvalue 314 is to be used (e.g., as the maximum run time). If a state is not completed within the time frame defined by Tvalue 314 and Tfunc 316, an error message may be generated to alert the user that an unexpected event happened in this state.

Sens 318, STst 320, and SMsk 322 pertain to determining the sensor state. There are a number of sensors in the microscopy analyzer unit 34 for measuring or detecting a parameter, and Sens 318 identifies the sensor that is relevant to a particular state. STst 320 identifies the status of the sensor (e.g., on or off). SMsk 322 provides a reference value that is compared against the STst value to determine a course of action. The STst value having a certain relationship with respect to the reference value is herein referred to as a "condition" for taking the subsequent step toward completion.

The signal from the host controller (SMTest 310), the statuses 308 of the third level controllers, and the status of the sensor (STst 320) relative to Smsk 322 determine the next state. If these values indicate that no branching is to occur, the current state ends and the next consecutivenumbered state index in the current run sequence becomes activated. If the current state ends at the end of a run sequence, a ToSM 312 signal is sent to the host controller 56 to indicate that a run sequence has been completed. The level-1 controller 52 will then remain idle until the host controller 56 issues another SMTest signal, activating a new run sequence. If SMTest 310, the level-2 controller statuses 308, and the sensor status STst 320 indicate that the current state is to branch, thereby satisfying the "predefined condition" for branching, Dest 328 points to the state to branch to and Bran 326 triggers the branching.

As mentioned above, a process engineer is able to adjust at least some of the parameter values in table 300 because they are parameters that make sense when the system is considered from the perspective of a process engineer. For example, the process engineer may adjust the Tvalue 314 so that a state waits for a longer or shorter period of time before generating an error signal, or adjust values in commands 306 so that a certain valve is open, not closed. The system includes a user interface through which the process engineer can adjust "calibration" values in separate tables (not just the level-1 controller table). These calibration values may be used to control time intervals, motor operation or as threshold settings for sensor readouts.

The controllers in the urinalysis system 30 convert the parameters input by the process engineer to generate the machine-readable values in column 330. Although a programmer is initially needed to program this conversion method, the programmer does not need to be involved each time a parameter is adjusted.

When the level-2 controllers 54a, 54b, 54c, and 54d receive commands 306 from the level-1 controller 52, each of the level-2 controllers 54 starts a function in accordance with the received command. As mentioned above, the spreadsheets for the level-2 controllers 54a, 54b, 54c, and 54d have substantially the same syntax as the spreadsheet for the level-1 controller. This similarity extends not only to the fields in the spreadsheets but also to the mode of communication with the adjacent levels. For example, in the same way that the level-1 controller's interpretation of a code from the adjacent higher level depends on the state of the level-1 controller at the time the code is received, the level-2 controller interprets an input differently depending on whether it is in an idle state or an active state when the code is received.

FIG. 9 illustrates what the first level-2 controller 54a does upon receiving a command from the level-1 controller 52. A first level-2 controller state record table 400 contains the commands to be sent to the valves 68, the pipette motors 60, 62, an evacuation pump 64, and the sheath pump 67 (see FIG. 4) in columns labeled Energized Valves 406, First Motor 410, Second Motor 412, EP 408, and SP 414, respectively. The positions of the valves and pumps are indexed by a state order 402, each of which has a description 404. The "SP" here is a dummy field that is not used in the particular embodiment, as indicated by a constant value in all the states.

The first level-2 controller 54a uses a pressure sensor to measure the pressure inside the air storage. This air is used to mix the specimen, for example by air-blasting. Sensor Select 416 identifies the sensor, Sensor State 418 indicates the status of the selected sensor, and Sensor Mask 420 contains a reference value. MotorTest 422, which detects the status of the motor, is one of the factors considered to determine what to do next. A motor may be in one of a few states, the exact number depending on the motor type. For example, a motor may be 1) running and not where it is supposed to be, 2) running and where it is supposed to be, or 3) stopped where it is supposed to be. The value in the MotorTest 422 indicates which of the three states the motor is in.

Unlike the level-1 controller 52, the first level-2 controller 54a does not test for specific messages from a higher-level controller, which in this case would be the level-1 controller 52. Thus, SM Test 424 is set at a value 0X0000. However, the statuses of the valves and motors are reported to the level-1 controller, as indicated by non-zero values in ToSM 426. Tvalue 428 indicates a time out value associated with each respective state and Tfunc 430 indicates how the time out value is to be used. Based on the value in MotorTest 422 (i.e., whether they satisfy the predefined condition with respect to the reference value), Tvalue 428, and Tfunc 430, the first level-2 controller determines whether the state is to end or not. If the state is to end, the value in the column labeled End Ctrl 432 indicates how the particular state is to end. If the state is to branch, a Bran Ctrl 434 briggers the branching and a Dest 436 points the state or the run sequence to branch to.

FIG. 10 depicts a second level-2 controller table 500 that may be used to direct the second level-2 controller 54b to execute certain functions. The second level-2 controller table 500 is indexed by a state order 502, each of which has a State Description 504. The second level-2 controller table 500 is similar to the first level-2 controller table 400 (see FIG. 4 above) in that it controls valves 68. In addition, it controls the sheath pump 67 and the cannula pump 70. MotorTest 522 detects the status of the sheath pump 67 and the cannula pump 70. Energized Valve 506 identifies the fluid block valves that are to be energized. Command columns 509 include a CP 508, which indicates a signal to be sent to the cannula pump, and an SP 514, which indicates a signal to be sent to the sheath pump. Dummy Motor 510 and Dummy Motor 512 are unused in the embodiment shown, as indicated by a constant value 80FF in both columns. The Dummy Motor fields may be used if more motors are added to the system. Likewise, the columns relating to sensor selection, such as Sensor Select 516, Sensor State 518, and Sensor Mask 520 are unused in the embodiment shown because the second level-2 controller does not use a sensor. The unused fields may be used if a component, such as a sensor, is used with the second level-2 controller 54. The motor states are tested and the status codes are compared to the test value in Motor Test 522. There is a two-way communication from the second level-2 controller 54b, the level-1 controller 52, as shown by the signals in ToSM 526. There is no signal transmitted from the level-1 controller controller 52 to the second level-2 controller 54b, however, as indicated by the constant value 0X0000 in SMTest 524.

Tvalue 528 indicates a time out value associated with each respective state and Tfunc 530 indicates how the time out value is to be used. If the current state does not end because the predefined conditions in EndCtl are not satisfied before the amount of time indicated by the time out value expires, an error signal may be generated. Depending on whther values of Motor Test 522, Tvalue 528, and Tfunc 530 satisfy this predefined condition or not, the state will either end or branch. The value in the column labeled End Ctrl 532 indicates the conditions to be satisfied for the particular state to end. If the state is to branch, a Bran Ctrl 534 indicates a condition or manner of branching and a Dest 536 points the state or the run sequence to branch to. In state 24, Dest=0, indicating that the next state is an idle state (state order 0).

FIG. 11 depicts a third level-2 controller state record table 600 for the third level-2 controller 54c, which controls the specimen rack 42 (see FIG. 3). The third level-2 controller state record table 600 is indexed by state order 602 and a description 604. As described above in FIG. 3, there are at least two conveyors in the system: an input conveyor (CI) and an output conveyor (CO). CI pushes the specimen rack toward the wall 48 of the microscopy analyzer unit 34 (see FIG. 3). The rack then shifts sideways incrementally to allow sampling of the different test tubes. A shifter arm (SM), controlled by the stepper motor 76a in FIG. 4, shifts the specimen rack 40 from the CI to the CO along this path, stopping to allow each tube to be sampled. Then, the CO moves the specimen rack from the position where CI left it and brings the specimen rack to the front, so that CI and the CO together take the specimen rack on a U-shaped path. A repositioning arm (CM) controlled by the stepper motor 76b (in FIG. 4) could be used to send a command 612 to move the rack from the finishing end of the U to the beginning end of the U so that the CI is able to move the specimen rack again. SM 610, CM 612, CI 614, and CO 616 show signals to be sent to the respective arms in each state. In the exemplary table 600, the columns Dor 606 and Dand 608, and RC 618 are dummy columns, as indicated by a constant value. These dummy columns may get used if additional components are incorporated into the system.

A few sensors are used by the third level-2 controller 54c. SenSel 620 identifies a sensor to be tested in each state, Stst 622 indicates the status of the sensor as determined by the test, and SMtst 624 indicates a reference value that is used for testing the status of the sensor. Mtst 626 is the encoded status of motors 76a, b, or 78a, b (see FIG. 4). SMtst 628 is unused, indicating that the level-1 controller 52 is not tested. Signals in ToSM 630 are sent to the level-1 controller 52 when certain conditions are fulfilled.

Tvalue 632 indicates a time out value associated with each respective state index and Tfunc 634 indicates how the time out value is to be used. Depending on whether the values of SM 610, CM 612, CI 614, CO 616, and Mtst 626 satisfy the predefined condition or not, the current state will either end or branch. If the state is to end, the value in the column labeled End Ctrl 636 indicates how the particular state is to end. If the state is to branch, a Bran Ctrl 638 triggers branching and a Dest 640 points the state or the run sequence to branch to.

EXAMPLE

This example illustrates how the multi-level controllers interact with each other to complete a run sequence. Specifically, this example illustrates how the level-1 controller resets the level-2 controllers and has them execute run sequences that prepare the system for processing samples (i.e., execute the first run sequence shown in FIG. 6). As shown in FIG. 6, the run sequence RH entails state indices 1-14 of the level-1 controller state record table 300. During this process, the sheath bottle is filled with a sheath fluid, the pipette position is initialized, and the STM initializes the position of rack motion levers and clears the input and output conveyor. In the first state of this reset process (i.e., FIG. 8, state index=1), the level-1 controller 52 sends a reset signal (RE) to each of the four high level controllers. The four level-2 controllers 54 reset themselves in response to the reset signal, and send back a status report (0XFF). After receiving all four status reports, the level-1 controller 52 sends the signals associated with state index 2. In state index 2, the level-1 controller 52 sends a signal "S1" to the first level-2 controller 54a. The first level-2 controller 54a, which will then start state 61 of the state record table 400, fills the sheath bottle. Since the value "0X0000" indicates that no signal is sent, no signal is sent to the second, third, and fourth level-2 controllers in state index 2. When the sheath bottle starts to get filled, the first level-2 controller 54a returns a completion status "0X32," as shown in the ToSM column of table 400 and the SPAstat column of table 300. The value 0x0002 in the End column 324 indicates that state index 2 will end as soon as the "0x32" status is returned from first level-2 controller 54a.

State index 3, which has a timeout value 314 of 0x0005 and a Tfunc 316 of 0x42, says to stop filling the sheath bottle when the time out value 314 is reached. The Sens 318 value of 0x0033, STst value of 0x01, and SMsk value of 0x01 indicate that if the sensor identified by 0x0033 reaches a state 0x01, the sheath bottle is full. The End column 324 has a value 0x8383, which means that the state is to end when either the sheath bottle is full or the timeout value 314 is reached. When the current state ends, the level-1 controller proceeds to state index 4, whereby an S0 signal is sent to the first level-2 controller 54a to turn off the filling. Upon receiving the signal S0, the first level-2 controller 54a turns off the sheath pump and sends the signal 0X33 to the level-1 controller 52, which then ends the current state.

In state index 5, the level-1 controller 52 waits for the first level-2 controller 54a to send a signal 0XFF indicating that the sheath pump is turned off and it is now idle.

After the sheath pump is filled, the sheath's level is tested in state index 6. The sheath level is tested by identifying the low sensor selected by 0X0032 in column 318, and comparing it against the calibration table value selected by SMsk value 0x80. If the comparison indicates that the sheath level is low, the process branches to state index 8 according to the Bran 32 and the Dest 8. In state index 8, it is tested whether the sheath is empty. If the sheath sensor 0X0032 in column 318 indicates that the sheath is empty when compared against the calibration table value selected by SMsk value of 0x40, the Bran 326 value and the Dest value 328 direct the level-1 controller to branch to state index 10. In state index 10, the level-1 controller sends a message 0x21 to the host processor to let the host processor know that the sheath is empty. Then, the level-1 controller branches to state index 100, which starts the rack clearing process.

Referring back to state index 6, if the sensor selected by 0X0032 does not indicate that the sheath level is low, no branching occurs and the next state would be state index 7. In state index 7, the level-1 controller 52 reports that the sheath level is okay to the host processor by sending a ToSM message 0X1F. Then, the level-1 controller 52 executes state index 11.

In state index 11, the level-1 controller 52 sends the commands PH, HS, and CR to the first level-2 controller 54a, the second level-2 controller 54b, and the third level-2 controller 54c, respectively. No signal is sent to the fourth level-2 controller (the OBA controller) because optical bench initialization is not required in the reset run sequence. The first level-2 controller, upon receiving the PH command, starts to lift the pipetter and send the pipetter to a back sensor and eventually to a waste well by executing states 4-9 in table 400. In states 4 and 5, signals are sent to the horizontal motor to move the pipette arm to the back sensor. In state 6, a signal is sent to the motor to rotate the pipetter out to the waste well. Then, air pressure is checked in state 7 by using a sensor 10B0 to compare against a reference sensor mask value. If the pressure is at an acceptable level already, the SPA controller 36b branches to state 9, where a message 0x12 is sent to the level-1 controller to inform that the pressure level is acceptable. If the pressure is not at an acceptable level, the first level-2 controller 54*a* sets valves and activates the air pump to recharge the pressure to the acceptable level in state 8 before sending the signal to the level-1 controller in state 9.

The second level-2 controller 54*b*, upon receiving the HS command, activates the valve CBV3 and sends the signal 80FE to the cannula pump 70 and the sheath pump 67 (see FIG. 4) to put them in standby positions in state 32. The pump roller is then placed on the tube in state 33. Then, a status report signal 0X21 is sent to the level-1 controller 52 in state 34.

The third level-2 controller 54*c*, upon receiving the CR command, runs the infeed conveyor in reverse by sending a signal 0X80FF to the SM, 0X0100 to the CI, and 0X880FF to the CO. This is done for a time period defined by Tval=0X0016 and Tfnc=0X02. After this predefined time period, a signal 0x30 is sent to the level-1 controller and state 34 ends.

Referring back to table 300, an FBAstat value of 0x21 is received in state 11. A Tvalue of 0x0009 and a Tfunc value of 0x44 set a time frame by which the FBAstat value must be returned. The End value 0x005F indicates that if the FBAstat value of 0x21 is not received by the end of the designated time frame, an error signal is generated; if the FBAstat value is received in time, the level-1 controller moves on to state 12.

In state index 12, the level-1 controller 52 waits to receive a SPAstat value of 0xFF and moves on to state 13 when it does. In state 13, the level-1 controller waits to receive an STMstat value of 0xFF, and moves on to state 14 when it does. In the run sequence Reset High (RH), no signal is exchanged between the level-1 controller and the OBA controller. In state 14, the Reset High run sequence ends.

With the leveled controller architecture 100 (see FIG. 5) of the invention, each level-2 controller 54 operates independently of each other. However, because the level-1 controller 52 does not proceed to the next state until all the expected status reports have been received from the high level controllers, the level-1 controller synchronizes the high level controllers at certain "check points" in the process. If not all the expected status reports are received within a designated time frame (e.g., Tvalue), an error signal is generated and, optionally, the process halts. Having this "check point" system at the end of each state prevents the entire process run from being tainted with an error. Furthermore, the "check point" system facilitates troubleshooting by allowing the process engineer to know exactly in which state the error occurred.

While the foregoing has been with reference to a particular embodiment of the invention, it will be appreciated by those skilled in the art that changes in this embodiment may be made without departing from the principles and spirit of the invention, the scope of which is defined by the appended claims.

For example, it is within the scope of the invention to allow the higher control levels to control a lower control level or the system components "directly" or "indirectly." If the control is "direct," there is no intervening level between the level that is doing the controlling and the level that is being controlled. For example, a level-1 controller usually directly controls a level-2 controller. In contrast, if the control is "indirect," there are one or more intervening levels between the level that is doing the controlling and the level that is being controlled. For example, in a three-level control system, the first control level may be designed so that it is able to control either the second control level or the third control level, depending on the situation.

In the embodiment including multiple lower level controllers, a command issued by a higher level controller is meant for, or "targeted to," one or more of the specific lower level controllers. In some embodiments, the higher level controller sends a command only to the targeted lower level controllers. In these embodiments, the lower level controllers that are not targeted do not receive the command. In other embodiments, the higher level controller "broadcasts" a command to many of the lower level controllers and let recipient lower level controllers determine whether the command applies to them. If a lower level controller determines that the command is not applicable, it will ignore the command.

Depending on the embodiment, controllers in the same control level are allowed limited or full communication with each other. Sometimes, the communication is limited to inter-level communication between a higher level controller and a lower level controller. A person of ordinary skill in the art will appreciate that numerous variations are possible.

What is claimed is:

1. A medical system for analyzing a sample comprising:
a first control level having at least one level-1 controller for moving through a sequence of first level states each associated with a unique first state index number, the first control level generating a first level command associated with one of the first level states; and
a second control level having a level-2 controller for moving through a sequence of second level states each associated with a unique second state index number in response to the first level command and for sending a status report to the first control level when a level-2 condition that is defined in one of the second level states is fulfilled;
wherein at least one of the first controller and the second controller sending or receiving signals to or from components of a medical system in response to the moving through the sequence of the first or second level states for controlling or sensing a status of the components;
wherein the components of the medical system comprise sample aspiration components, flow cell components, transport mechanisms, and image acquisition components for urinalysis, and the second control level comprising:
a first level-2 controller for controlling the sample aspiration components, wherein the first level-2 controller is the level-2 controller;
a second level-2 controller for controlling the flow cell components;
a third level-2 controller for controlling the transport mechanisms associated with sampling; and
a fourth level-2 controller for controlling the image acquisition components.

2. The system of claim 1, wherein the second control level comprises a plurality of level-2 controllers including the level-2 controller, and wherein the first level command is targeted to the level-2 controller.

3. The system of claim 1, wherein the level-1 controller tests a level-1 condition that is defined in one of the first level states, and moves from the one first level state to another of the first level states in response to the status report and the testing.

4. The system of claim 1, wherein at least one of the level-1 controller and the level-2 controller directly controls a system component by issuing the first level command or a second level command, respectively.

5. The system of claim 4 further comprising a third control level interfacing between the second control level and the system component, wherein the third control level is designed for receiving at least one of the first level command and the second level command and translating the received command for the system component.

6. The system of claim 1 further comprising a processor for generating a level-1 controller table containing parameters, wherein the level-1 controller identifies the first level command associated with the one first level state by accessing the parameters in the level-1 controller table.

7. The system of claim 6 further comprising a user interface, wherein the parameters in the level-1 controller table are changeable by adjusting values in the user interface.

8. The system of claim 1, wherein the sequence of first level states comprises a plurality of sequences including the sequence, and wherein the level-1 controller selects, among the plurality of sequences, the sequence of first level states to move through in response to a host level command received from a host control level.

9. The system of claim 1 further comprising a pump, a valve, and a motor, wherein the pump, the valve, and the motor are controlled by the first level-2 controller.

10. The system of claim 1 further comprising a processor for generating a level-2 controller table containing second level commands, wherein the first level-2 controller controls the sample aspiration components according to the level-2 controller table, and wherein the level-2 controller table is indexed by the second state index numbers.

11. The system of claim 10, wherein the level-2 controller table indicates which of the second level states to move through in response to the first level command.

12. The system of claim 10, wherein the level-2 controller table comprises:
rows indexed by the second state index numbers;
a first set of columns indicating the second level commands;
a second set of columns indicating status reports including the status report;
a third set of columns indicating level-2 tests for checking if level-2 conditions including the level-2 condition are fulfilled; and
a fourth set of columns indicating one of the second level states to move to, wherein the one second level state depends on results of the level-2 tests.

13. The system of claim 12 further comprising a processor for generating a level-1 controller table, the level-1 controller table comprising:
rows indexed by the first state index numbers;
a first set of columns indicating first level commands including the first level command;
a second set of columns indicating status reports to be generated by the level-1 controller;
a third set of columns indicating level-1 tests for checking if level-1 conditions are fulfilled; and
a fourth set of columns indicating courses of action according to results of the tests.

14. The system of claim 1, wherein the first level-2 controller controls the sample aspiration components, wherein a subgroup of sample aspiration components are controlled by both the first and the second level-2 controllers.

15. The system of claim 1, wherein the flow cell comprise a valve and a pump for controlling flow of fluids.

16. The system of claim 1 further comprising a specimen rack for holding urinalysis samples, wherein the transport mechanisms comprise at least one of an arm, a motor, and a conveyor belt for transporting the specimen rack.

17. The system of claim 1 further comprising a processor for generating a level-2 controller table containing parameters, wherein the third level-2 controller controls the transport mechanisms according to the parameters in the level-2 controller table.

18. The system of claim 1, wherein the image acquisition components comprise a strobe bulb, a camera, and a motor.

19. The system of claim 1, wherein the level-1 controller, in response to a test result, performs one of the following:
proceeds from one of the first level states to another of the first level states;
proceeds to an idle state; and
generates an error signal depending on a result of a test.

20. The system of claim 19, wherein the test comprises obtaining a sensor reading and comparing the sensor reading to a reference value, and the result comprises relative magnitudes of the sensor reading and the reference value.

21. The system of claim 20 further comprising a nonvolatile memory containing the reference value, wherein the reference value is changeable by reprogramming of the nonvolatile memory.

22. The system of claim 20 further comprising a user interface, wherein the reference value is changeable through the user interface without overwriting a preprogrammed reference value.

23. The system of claim 1, wherein the second control level comprises a plurality of level-2 controllers including the level-2 controller, wherein each of the plurality of level-2 controllers is for moving through a unique sequence of second level states in response to the first level command, wherein the plurality of level-2 controllers move through their respective sequences asynchronously with respect to each other, and wherein the level-1 controller completes a first level state in response to the plurality of level-2 controllers' completion of their respective sequences of second level states.

24. The system of claim 23, wherein the plurality of level-2 controllers directly or indirectly control a system component.

* * * * *